US008829198B2

(12) United States Patent
Esposito et al.

(10) Patent No.: US 8,829,198 B2
(45) Date of Patent: *Sep. 9, 2014

(54) COMPOUNDS, COMPOSITIONS AND METHODS FOR THE TREATMENT OF BETA-AMYLOID DISEASES AND SYNUCLEINOPATHIES

(75) Inventors: Luke A. Esposito, Seattle, WA (US); F. Michael Hudson, Seattle, WA (US); Thomas Lake, Snohomish, WA (US); Joel Cummings, Seattle, WA (US); Manfred Weigele, Cambridge, MA (US); Alan D. Snow, Lynnwood, WA (US); Lesley Larsen, Dunedin (NZ)

(73) Assignee: Proteotech Inc, Kirkland, WA (US)

( * ) Notice: Subject to any disclaimer, the term of this patent is extended or adjusted under 35 U.S.C. 154(b) by 893 days.

This patent is subject to a terminal disclaimer.

(21) Appl. No.: 12/244,968

(22) Filed: Oct. 3, 2008

(65) Prior Publication Data

US 2009/0111863 A1    Apr. 30, 2009

Related U.S. Application Data

(60) Provisional application No. 61/001,441, filed on Oct. 31, 2007.

(51) Int. Cl.
*A61K 31/4196* (2006.01)
*A61K 31/4164* (2006.01)
*A61K 31/18* (2006.01)
*A61K 31/05* (2006.01)
*C07D 249/08* (2006.01)
*C07D 233/54* (2006.01)
*C07C 311/29* (2006.01)
*C07C 39/10* (2006.01)

(52) U.S. Cl.
CPC ............ *C07C 311/29* (2013.01); *C07D 249/08* (2013.01); *C07D 233/54* (2013.01); *C07C 39/10* (2013.01); *A61K 31/4196* (2013.01); *A61K 31/4164* (2013.01); *A61K 31/18* (2013.01); *A61K 31/05* (2013.01)
USPC ....... 548/269.4; 548/343.5; 564/89; 568/719; 514/383; 514/400; 514/604; 514/732

(58) Field of Classification Search
CPC .. C07D 249/08; C07D 233/54; C07C 311/29; C07C 39/10; A61K 31/4196; A61K 31/4164; A61K 31/18; A61K 31/05
USPC ............... 514/383, 400, 604, 732; 548/269.4, 548/343.5; 564/89; 568/719
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni et al. |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,522,811 A | 6/1985 | Eppstein et al. |
| 4,710,384 A | 12/1987 | Rotman |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,387,681 A | 2/1995 | Miller et al. |
| 5,591,767 A | 1/1997 | Mohr et al. |
| 5,639,476 A | 6/1997 | Oshlack et al. |
| 5,674,533 A | 10/1997 | Santus et al. |
| 5,709,874 A | 1/1998 | Hanson et al. |
| 5,733,566 A | 3/1998 | Lewis |
| 5,759,542 A | 6/1998 | Gurevich |
| 5,840,674 A | 11/1998 | Yatvin et al. |
| 5,900,252 A | 5/1999 | Calanchi et al. |
| 5,972,366 A | 10/1999 | Haynes et al. |
| 5,985,307 A | 11/1999 | Hanson et al. |
| 6,004,534 A | 12/1999 | Langer et al. |
| 6,039,975 A | 3/2000 | Shah et al. |
| 6,048,736 A | 4/2000 | Kosak |
| 6,060,082 A | 5/2000 | Chen et al. |
| 6,071,495 A | 6/2000 | Unger et al. |
| 6,120,751 A | 9/2000 | Unger |
| 6,131,570 A | 10/2000 | Schuster et al. |
| 6,139,865 A | 10/2000 | Friend et al. |
| 6,253,872 B1 | 7/2001 | Neumann |
| 6,255,327 B1 | 7/2001 | Brenner et al. |
| 6,271,359 B1 | 8/2001 | Norris et al. |

(Continued)

FOREIGN PATENT DOCUMENTS

WO    WO 2004/033432    *  4/2004 ........... C07D 231/12
WO    WO2006/120133 A2    11/2006

(Continued)

OTHER PUBLICATIONS

Arai et al., "Argyrophilic glial inclusions in the midbrain of patients with Parkinson's disease and diffuse Lewy body ... ", Neuroscience Letters 259:83-86 (1999).
Barner, E.L. and Gray, S.L., "Donepezil use in Alzheimer's disease", The Annals of Pharmacotherapy 32:70-77 (1998).
Bentiss et al., "A Simple One Step Synthesis of New 3,5-Distributed-4-amino-1,2,4-triazoles", J. Heterocyclic Chem. 36:149-152 (1999).
Bentiss et al., "An Improved Procedure for the Deamination of Symmetrical 3,5-Disubstituted 4-Amino-1,2,4-trazoles", J. Heterocyclic Chem. 39:93-96 (2002).
Betarbet et al., "Chronic systemic pesticide exposure reproduces features of Parkinson's disease", Nature Neuroscience 3:1301-1306 (2000).
Castedo et al., "Fremy's Salt Oxidation of Benzylamines. An Oxidative Deamination Reaction", Tetrahedron 38(11):1569-1570 (1982).
Chiti, F. and Dobson, C.M., "Protein Misfolding, Functional Amyloid and Human Disease", Annual Review of Biochemistry 75:333-366 (2006).

(Continued)

*Primary Examiner* — Joseph Kosack
(74) *Attorney, Agent, or Firm* — Rebecca Eagen

(57) ABSTRACT

Dihydroxyaryl compounds and pharmaceutically acceptable esters, their synthesis, pharmaceutical compositions containing them, and their use in the treatment of β-amyloid diseases, such as observed in Alzheimer's disease, and synucleinopathies, such as observed in Parkinson's disease, and the manufacture of medicaments for such treatment.

15 Claims, 31 Drawing Sheets

(56) References Cited

U.S. PATENT DOCUMENTS

| | | | |
|---|---|---|---|
| 6,274,552 | B1 | 8/2001 | Tamarkin et al. |
| 6,288,061 | B1 | 9/2001 | Sueoka |
| 6,316,652 | B1 | 11/2001 | Steliou |
| 6,465,504 | B1 | 10/2002 | Lattmann et al. |
| 6,596,750 | B2 | 7/2003 | Lattmann et al. |
| 6,723,742 | B2 | 4/2004 | Lattmann et al. |
| 7,514,583 | B2* | 4/2009 | Snow et al. ............... 564/179 |
| 7,531,669 | B2 | 5/2009 | Schubert |
| 2004/0127555 | A1* | 7/2004 | Snow et al. ............... 514/464 |
| 2005/0235428 | A1 | 10/2005 | Bachmann et al. |
| 2005/0245573 | A1 | 11/2005 | Neitzel |
| 2005/0288375 | A1 | 12/2005 | Hobden |
| 2007/0276034 | A1 | 11/2007 | Esposito |
| 2008/0187510 | A1 | 8/2008 | Camenisch et al. |
| 2008/0279962 | A1 | 11/2008 | Nick et al. |
| 2012/0035230 | A1* | 2/2012 | Esposito et al. ............ 514/383 |

FOREIGN PATENT DOCUMENTS

| | | |
|---|---|---|
| WO | WO2008/015021 A1 | 2/2008 |
| WO | WO2008/138912 A1 | 11/2008 |
| WO | WO2008/142094 A1 | 11/2008 |
| WO | 2009/111611 A2 | 9/2009 |
| WO | 2010/000372 A2 | 1/2010 |

OTHER PUBLICATIONS

Choshi et al., "Synthesis of Dibenzoylmethane Derivatives and Inhibition of Mutagenicity in *Salmonella typhimurium*", Chem. Pharm. Bull. 40(4):1047-1049 (1992).
Cohen, F. E. and Kelly, J.W., "Therapeutic approaches to protein-misfolding diseases", Nature 426:905-909 (2003).
Conway et al., "Accelerated in vitro fibril formation by a mutant α-synuclein linked to early-onset Parkinson disease", Nature Medicine 4(11):1318-1320 (1998).
Cutler, N.R. and Sramek, J. J., "Tacrine in Alzheimer's disease", The New England Journal of Medicine 328:808-810 (1993).
Dauer, W. and Przedborski, S., "Parkinson's Disease: Mechanisms and Models", Neuron 39:889-909 (2003).
Fink et al., "Novel structural templates for estrogen-receptor ligands and prospects for combinatorial synthesis of estrogens", Chemistry and Biology 6:205-219 (1999).
Fleming et al., "Early and Progressive Sensorimotor Anomalies in Mice Overexpressing Wild-Type Human α-Synuclein", J. Neurosci. 24:9434-9440 (2004).
Fleming et al., "Behavioral effects of dopaminergic agonists in transgenic mice overexpressing human wildtype α-synuclein", Neuroscience 142:1245-1253 (2006).
Flood et al., "An amyloid β-protein fragment, Aβ[12-28], equipotently impairs post-training memory, processing when injected . . . ", Brain Research 663:271-276 (1994).
Flood et al., "Amnestic effects in mice of four synthetic peptides homologous to amyloid β protein from patients with . . . ", Prod. Natl. Acad. Sci. 88:3363-3366 (1991).
Games et al., "Alzheimer-type neuropathology in transgenic mice overexpressing V717F β-amyloid precursor protein", Nature 373:523-527 (1995).
Glenner, G.G. and Wong, C.W., "Alzheimer's Disease: Initial Report of the Purification and Characterisation of a Novel . . . ", Biochem Biophys Res Comm 120(3): 885-890 (1984).
Greenamyre et al., "Complex I and Parkinson's disease", IUMBM Life 52:135-141 (2001).
Grundke-Iqbal et al., "Abnormal phosphorylation of the microtubule-associated protein τ(tau) in Alzheimer . . . ", Procl. Natl. Acad. Sci. USA 83:4913-4917 (1986).
Haass et al., "The Swedish mutation causes early-onset Alzheimer's Disease by β-secretase cleavage within the secretory pathway", Nature Medicine 1(12):1291-1296 (1995).
Hardy J., "Framing β-amyloid", Nature Genetics 1:233-234 (1992).
Harrigan et al., "Beta Amyloid is Neurotoxic in Hippocampal Slice Cultures", Neurobiology of Aging 16(5):779-789 (1995).
Hashimoto et al., "Human recombinant NACP/α-synuclein is aggregated and fibrillated in vitro: Relevance for Lewy body disease", Brain Research 799:301-306 (1998).
Hashimoto et al., "Transgenic models of alpha-synuclein pathology: past, present, and future", Ann. N. Y. Acad. Sci. 991:171-188 (2003).
Hsiao et al., "Correlative memory Deficits, Aβ Elevation, and Amyloid Plaques in Transgenic Mice", Science 274:99-102 (1996).
Husby et al., "Nomenclature of Amyloid and Amyloidosis", Bull. WHO 71 (1):105-108 (1993).
Janus, et al., "Aβ peptide immunization reduces behavioral impairment and plaques in a model of Alzheimer's disease", Nature 408:979-982 (2000).
Kosik et al., "Microtubule-associated protein tau (τ) is a major antigenic component of paired helical filaments in Alzheimer disease", Procl. Natl. Acad. Sci. USA 83:4044-404.
Krüger et al., "Ala30Pro mutation in the gene encoding α-synuclein in Parkinson's disease", Nature Genetics 18:106-108 (1998).
Lee, V., and Trojanowski, J., "Mechanisms of Parkinson's Disease Linked to Pathological α-Synuclein: New Targets for Drug Discovery", Neuron 52:33-38 (2006).
Lee et al., "A-68: A Major Subunit of Paired Helical Filaments and Derivatized Forms of Normal Tau", Science 251:675-678 (1991).
Lee et al., "Efficient α-Halogenation of Carbonyl Compounds by N-Bromosuccinimide and N-Chlorosuccinimide", Korean Chem. Soc. 24(4):407-408 (2003).
LeVine III, H., "Thioflavine T interaction with synthetic Alzheimer's disease β-amyloid peptides: Detection of amyloid aggregation in solution", Protein Sci 2:404-410 (19993).
LeVine III, H., "Thioflavine T interaction with amyloid β-sheet structures", Amyloid: The International Journal of Experimental and Clinical Investigation 2:1-6 (1995).
Lewy, F.H., "Paralysis agitans" in Handbuch der Neurologie, M. Lawandowsky (Ed.), Berlin: Springer-Verlag pp. 920-933 (1912).
Li et al., "An Optimized Process for Formation of 2,4-Disubstituted Imidazoles from Condensation of Amidines and . . . ", Organic Process Research & Development 6:682-683 (2002).
Lockhart et al., "Evidence for the Presence of Three Distinct Binding Sites for the Thioflavin T Class of Alzheimer's Disease PET . . . ", J of Biol Chem 280:7677-7684 (2005).
Lopez et al., "Galiposin: A New β-Hydroxychalcone from *Galipea granulosa*", Planta Med. 64(1):76-77 (1998).
Lu et al., "Adamantyl Cannabinoids: A Novel Class of Cannabinergic Ligands", J. Med. Chem. 48(14):4576-4585 (2005).
Mandybur T., "Cerebral Amyloid Angiopathy: The Vascular Pathology and Complications", Journal of Neuropathology and Experimental Neurology 45(1):79-90 (1986).
Masters et al., "Amyloid plaque core protein in Alzheimer's disease and Down syndrome", Proc. Natl. Sci. USA 82:4245-4249 (1985).
Masuda et al., "Small Molecule Inhibitors of α-Synuclein Filament Assembly", Biochemistry 45:6085-6094 (2006).
Morgan, et al., "Aβ peptide vaccination prevents memory loss in an animal model of Alzheimer's disease", Nature 408:982-985 (2000).
Murray et al., "Synucleinopathies: A Molecular and Pathological Review", Clinical Neuroscience Research 1:445-455 (2001).
Murrell et al., "A Mutation in the Amyloid Precursor Protein Associated with hereditary Alzheimer's Disease", Science 254:97-99 (1991).
Naiki et al., Kinetic Analysis of Amyloid Fibril Polymerization In vitro, Laboratory Investigations 65(1):104-110 (1991).
Narhri et al., "Both Familial Parkinson's Disease Mutations Accelerate α-Synuclein Aggregation", The Journal of Biological Chemistry 274(14):9843-9846 (1999).
Nicklas et al., "Inhibition of NADH-linked oxidation in brain mitochondria by 1-methyl-4-phenyl-pyridine, a metabolite of the neurotoxin . . . ", Life Sci. 36:2503-2508 (1985).
Ono et al., "Potent anti-amyloidogenic and fibril destabilizing effects of polyphenols in vitro: implications for the prevention and . . . ", J. Neurochem. 87:172-181 (2003).
Ostrerova-Golts et al., "The A53T α-Synuclein Mutation Increases Iron-Dependent Aggregation and Toxicity", J. Neurosci. 20:6048-6054 (2000).
Panov et al., "Rotenone Model of Parkinson's Disease. Multiple Brain Mitochondria Dysfunctions After Short Term Systemic Rotenone . . . ", J. Biol. Chem. 280:42026-42035 (2005).

(56) References Cited

OTHER PUBLICATIONS

Papadimitriou et al., "Mutated α-synuclein gene in two Greek kindreds with familial PD: Incomplete penetrance?", Neurology 52:651-654 (1999).
Pardridge et al., "Amyloid Angiopathy of Alzheimer's Disease: Amino Acid Composition and Partial Sequence of a 4,200-Dalton Peptide . . . ", J. Neurochem. 49(5):1394-1401 (1987).
Pike et al., "In vitro aging of β-amyloid protein causes peptide aggregation and neurotoxicity", Brain Research 563:311-314 (1991).
Pike et al., "Structure-Activity Analyses of β-Amyloid Peptides: Contributions of the β25-35 Region to Aggregation and Neurotoxicity", J. Neurochem. 64(1):253-265 (1995).
Pollanen et al. "Pathology and Biology of the Lewy Body", Journal of Neuropathology and Experimental Neurology 52: 183-191 (1993).
Polymeropoulos et al., "Mutation in the α-Synuclein Gene Identified in families with Parkinson's Disease", Science 276:2045-2047 (1997).
Polymeropoulos et al., "Mapping of a Gene for Parkinson's Disease to Chromosome 4q21-q23", Science 274:1197-1199 (1996).
Porat et al., "Inhibition of Amyloid Fibril Formation by Polyphenols: Structural Similarity and Aromatic Interactions as a Common . . . ", Chem Biol Drug Des 67:27-37 (2006).
Reinke, A.A., and Gestwicki, J.E., "Structure-activity Relationships of Amyloid Beta-aggregation Inhibitors based on Curcumin . . . ", Chem Biol Drug Res 70:206-215 (2007).
Rockenstein et al., "Differential neuropathological alterations in transgenic mice expressing alpha-synuclein from the platelet-derived..", J. Neurosci. Res. 68:568-578 (2002).
Rogers, S.L. and Friendhoff, L.T., "Long-term efficacy and safety of donepezil in the treatment of Alzheimer's disease . . . ", Eur. Neuropsych. 8:67-75 (1998).
Schapira et al., "Mitochondrial complex I deficiency in Parkinson's disease", J.Neurochem. 54:823-827 (1990).
Sherer et al., "An in vitro model of Parkinson's disease: linking mitochondrial impairment to altered alpha-synuclein metabolism and . . . ", J. Neurosci. 22:7006-7015 (2002).
Sherer et al., "Mechanism of toxicity in rotenone models of Parkinson's disease", J. Neurosci. 23:10756-10764 (2003).
Shoval, et al., "The molecular mechanisms of the anti-amyloid effects of phenols", Amyloid 14(1):73-87 (2007).
Soto, C., "Protein misfolding and disease; protein refolding and therapy", FEBS Letters 498: 204-207 (2001).
Spillantini et al., "Alpha-Synuclein in filamentous inclusions of Lewy bodies from Parkinson's disease", Proc. Natl. Acad. Sci. USA 95:6469-6473 (1998).
Tanzi et al., "Protease inhibitor domain encoded by an amyloid protein precursor mRNA associated with Alzheimer's disease", Nature 331:528-532 (1988).
Testa et al., "Rotenone induces oxidative stress and dopaminergic neuron damage in organotypic substantia nigra cultures", Mol. Brain Res. 134:109-118 (2005).
Thurkauf et al., "2-Phenyl-4-(aminomethyl) imidazoles as Potential Antipsychotic Agents. Synthesis and Dopamine2 Receptor Binding", J. Med. Chem. 38(12):2251-2255 (1995).
Trojanowski, J.Q. and Lee, V.M., "Parkinson's Disease and Related Synucleinopathies are a New Class of Nervous System Amyloidoses", Neurotoxicology 23:457-460 (2002).
Ueda et al., "Molecular cloning of cDNA encoding an unrecognized component of amyloid in Alzheimer's disease", Proc. Natl. Acad. Sci. USA 90:11282-11286 (1993).
Vallet et al., "A comparative study of histological and immunohistochemical methods for neurofibrillary tangles and senile plaques . . . ", Acta Neuropathol. 83:170-178 (1992).
Van Broeckhoven et al., "Amyloid β Protein Precursor Gene and Hereditary Cerebral Hemorrhage with Amyloidosis (Dutch)", Science 248:1120-1122 (1990).
Ved et al., "Similar patterns of mitochondrial vulnerability and rescue induced by genetic modification of α-synuclein, parkin . . . ", J. Biol. Chem. 280:42655-42668 (2005).
Wakabayashi et al., "Accumulation of α-synuclein/NACP is a cytopathological feature common to Lewy body disease and multiple system atrophy", Acta Neuropath 96:445-452 (1998).
Wood et al., "α-Synuclein Fibrillogenesis Is Nucleation-dependent", The Journal of Biological Chemistry 274(28):19509-19512 (1999).
Ye et al., "Delineation of Positron Emission Tomography Imaging Agent Binding Sites on β-Amyloid Peptide Fibrils", J. Biol. Chem. 280:23599-23604 (2005).

* cited by examiner

A.

B.

A.

B.

A

B

A

B

COMPOUNDS, COMPOSITIONS AND METHODS FOR THE TREATMENT OF BETA-AMYLOID DISEASES AND SYNUCLEINOPATHIES

RELATED APPLICATIONS

This application claims priority under 35 U.S.C. §119(e) to U.S. provisional application Ser. Nos. 61/001,441, entitled "Compounds, Compositions and Methods for the Treatment of β-Amyloid Diseases and Synucleinopathies" to Esposito et al., filed Oct. 31, 2007.

TECHNICAL FIELD

This invention relates to bis-dihydroxyaryl compounds and pharmaceutically acceptable salts, their synthesis, pharmaceutical compositions containing them, and their use in the treatment of Aβ amyloid disease, such as observed in Alzheimer's disease, and synucleinopathies, such as observed in Parkinson's disease, and in the manufacture of medicaments for such treatment.

BACKGROUND OF THE INVENTION

Alzheimer's disease is characterized by the accumulation of a 39-43 amino acid peptide termed the β-amyloid protein or Aβ, in a fibrillar form, existing as extracellular amyloid plaques and as amyloid within the walls of cerebral blood vessels. Fibrillar Aβ amyloid deposition in Alzheimer's disease is believed to be detrimental to the patient and eventually leads to toxicity and neuronal cell death, characteristic hallmarks of Alzheimer's disease. Accumulating evidence implicates amyloid, and more specifically, the formation, deposition, accumulation and/or persistence of Aβ fibrils, as a major causative factor of Alzheimer's disease pathogenesis. In addition, besides Alzheimer's disease, a number of other amyloid diseases involve formation, deposition, accumulation and persistence of Aβ fibrils, including Down's syndrome, disorders involving congophilic angiopathy, such as but not limited to, hereditary cerebral hemorrhage of the Dutch type, and cerebral β-amyloid angiopathy.

Parkinson's disease is another human disorder characterized by the formation, deposition, accumulation and/or persistence of abnormal fibrillar protein deposits that demonstrate many of the characteristics of amyloid. In Parkinson's disease, an accumulation of cytoplasmic Lewy bodies consisting of filaments of α-synuclein are believed important in the pathogenesis and as therapeutic targets. New agents or compounds able to inhibit α-synuclein formation, deposition, accumulation and/or persistence, or disrupt pre-formed α-synuclein fibrils (or portions thereof) are regarded as potential therapeutics for the treatment of Parkinson's and related synucleinopathies. A 35 amino acid fragment of α-synuclein that has the ability to form amyloid-like fibrils either in vitro or as observed in the brains of patients with Parkinson's disease. The fragment of α-synuclein is a relative important therapeutic target as this portion of α-synuclein is believed crucial for formation of Lewy bodies as observed in all patients with Parkinson's disease, synucleinopathies and related disorders. In addition, the α-synuclein protein which forms fibrils, and is Congo red and Thioflavin S positive (specific stains used to detect amyloid fibrillar deposits), is found as part of Lewy bodies in the brains of patients with Parkinson's disease, Lewy body disease (Lewy in *Handbuch der Neurologie*, M. Lewandowski, ed., Springer, Berlin pp. 920-933, 1912; Pollanen et al, *J. Neuropath. Exp. Neurol.* 52:183-191, 1993; Spillantini et al, *Proc. Natl. Acad. Sci. USA* 95:6469-6473, 1998; Arai et al, *Neurosci. Lett.* 259:83-86, 1999), multiple system atrophy (Wakabayashi et al, *Acta Neuropath.* 96:445-452, 1998), dementia with Lewy bodies, and the Lewy body variant of Alzheimer's disease. In Parkinson's disease, fibrils develop in the brains of patients with this disease which are Congo red and Thioflavin S positive, and which contain predominant beta-pleated sheet secondary structure.

Amyloid as a Therapeutic Target for Alzheimer's Disease

Alzheimer's disease also puts a heavy economic burden on society. A recent study estimated that the cost of caring for one Alzheimer's disease patient with severe cognitive impairments at home or in a nursing home, is more than $47,000 per year (*A Guide to Understanding Alzheimer's Disease and Related Disorders*). For a disease that can span from 2 to 20 years, the overall cost of Alzheimer's disease to families and to society is staggering. The annual economic toll of Alzheimer's disease in the United States in terms of health care expenses and lost wages of both patients and their caregivers is estimated at $80 to $100 billion (2003 *Progress Report on Alzheimer's Disease*).

Tacrine hydrochloride ("Cognex"), the first FDA approved drug for Alzheimer's disease, is a acetylcholinesterase inhibitor (Cutler and Sramek, *N. Engl. J. Med.* 328:808 810, 1993). However, this drug has showed limited success in producing cognitive improvement in Alzheimer's disease patients and initially had major side effects such as liver toxicity. The second FDA approved drug, donepezil ("Aricept"), which is also an acetylcholinesterase inhibitor, is more effective than tacrine, by demonstrating slight cognitive improvement in Alzheimer's disease patients (Barner and Gray, *Ann. Pharmacotherapy* 32:70-77, 1998; Rogers and Friedhoff, *Eur. Neuropsych.* 8:67-75, 1998), but is not believed to be a cure. Therefore, it is clear that there is a need for more effective treatments for Alzheimer's disease patients.

Alzheimer's disease is characterized by the deposition and accumulation of a 39-43 amino acid peptide termed the beta-amyloid protein, Aβ or β/A4 (Glenner and Wong, *Biochem. Biophys. Res. Comm.* 120:885-890, 1984; Masters et al., *Proc. Natl. Acad. Sci. USA* 82:4245-4249, 1985; Husby et al., *Bull. WHO* 71:105-108, 1993). Aβ is derived by protease cleavage from larger precursor proteins termed β-amyloid precursor proteins (APPs) of which there are several alternatively spliced variants. The most abundant forms of the APPs include proteins consisting of 695, 751 and 770 amino acids (Tanzi et al., *Nature* 31:528-530, 1988).

The small Aβ peptide is a major component that makes up the amyloid deposits of "plaques" in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grundke-Iqbal et al., *Proc. Natl. Acad. Sci. USA* 83:4913-4917, 1986; Kosik et al., *Proc. Natl. Acad. Sci. USA* 83:4044-4048, 1986; Lee et al., *Science* 251:675-678, 1991). The pathological hallmark of Alzheimer's disease is therefore the presence of "plaques" and "tangles", with β-amyloid being deposited in the central core of the plaques. The other major type of lesion found in the Alzheimer's disease brain is the accumulation of β-amyloid in the walls of blood vessels, both within the brain parenchyma and in the walls of meningeal vessels that lie outside the brain. The β-amyloid deposits localized to the walls of blood vessels are referred to as cerebrovascular amyloid or congophilic angiopathy (Mandybur, *J. Neuropath. Exp. Neurol.* 45:79-90, 1986; Pardridge et al., *J. Neurochem.* 49:1394-1401, 1987)

For many years there has been an ongoing scientific debate as to the importance of "β-amyloid" in Alzheimer's disease, and whether the "plaques" and "tangles" characteristic of this disease were a cause or merely a consequence of the disease. Within the last few years, studies now indicate that β-amyloid is indeed a causative factor for Alzheimer's disease and should not be regarded as merely an innocent bystander. The Alzheimer's Aβ protein in cell culture has been shown to cause degeneration of nerve cells within short periods of time (Pike et al., *Br. Res.* 563:311-314, 1991; *J. Neurochem.* 64:253-265, 1995). Studies suggest that it is the fibrillar structure (consisting of a predominant β-pleated sheet secondary structure), which is responsible for the neurotoxic effects. Aβ has also been found to be neurotoxic in slice cultures of hippocampus (Harrigan et al., *Neurobiol. Aging* 16:779-789, 1995) and induces nerve cell death in transgenic mice (Games et al., *Nature* 373:523-527, 1995; Hsiao et al., *Science* 274: 99-102, 1996). Injection of the Alzheimer's Aβ into rat brain also causes memory impairment and neuronal dysfunction (Flood et al., *Proc. Natl. Acad. Sci. USA* 88:3363-3366, 1991; *Br. Res.* 663:271-276, 1994).

Probably, the most convincing evidence that Aβ amyloid is directly involved in the pathogenesis of Alzheimer's disease comes from genetic studies. It was discovered that the production of Aβ can result from mutations in the gene encoding its precursor, β-amyloid precursor protein (Van Broeckhoven et al., *Science* 248:1120-1122, 1990; Murrell et al., *Science* 254:97-99, 1991; Haass et al., *Nature Med.* 1:1291-1296, 1995). The identification of mutations in the beta-amyloid precursor protein gene that cause early onset familial Alzheimer's disease is the strongest argument that amyloid is central to the pathogenetic process underlying this disease. Four reported disease-causing mutations have been discovered which demonstrate the importance of Aβ in causing familial Alzheimer's disease (reviewed in Hardy, *Nature Genet.* 1:233-234, 1992). All of these studies suggest that providing a drug to reduce, eliminate or prevent fibrillar Aβ formation, deposition, accumulation and/or persistence in the brains of human patients will serve as an effective therapeutic.

Parkinson's Disease and Synucleinopathies

Parkinson's disease is a neurodegenerative disorder that is pathologically characterized by the presence of intracytoplasmic Lewy bodies (Lewy in *Handbuch der Neurologie*, M. Lewandowski, ed., Springer, Berlin, pp. 920-933, 1912; Pollanen et al., *J. Neuropath. Exp. Neurol.* 52:183-191, 1993), the major components of which are filaments consisting of α-synuclein (Spillantini et al., *Proc. Natl. Acad. Sci. USA* 95:6469-6473, 1998; Arai et al., *Neurosci. Lett.* 259:83-86, 1999), an 140-amino acid protein (Ueda et al., *Proc. Natl. Acad. Sci. USA* 90:11282-11286, 1993). Two dominant mutations in α-synuclein causing familial early onset Parkinson's disease have been described suggesting that Lewy bodies contribute mechanistically to the degeneration of neurons in Parkinson's disease and related disorders (Polymeropoulos et al., *Science* 276:2045-2047, 1997; Kruger et al., *Nature Genet.* 18:106-108, 1998). Recently, in vitro studies have demonstrated that recombinant α-synuclein can indeed form Lewy body-like fibrils (Conway et al., *Nature Med.* 4:1318-1320, 1998; Hashimoto et al., *Brain Res.* 799:301-306, 1998; Nahri et al., *J. Biol. Chem.* 274:9843-9846, 1999). Most importantly, both Parkinson's disease-linked α-synuclein mutations accelerate this aggregation process, demonstrating that such in vitro studies may have relevance for Parkinson's disease pathogenesis. Alpha-synuclein aggregation and fibril formation fulfills the criteria of a nucleation-dependent polymerization process (Wood et al., *J. Biol. Chem.* 274:19509-19512, 1999). In this regard α-synuclein fibril formation resembles that of Alzheimer's β-amyloid protein (AβP) fibrils. Alpha-synuclein recombinant protein, and non-Aβ component (known as NAC), which is a 35-amino acid peptide fragment of α-synuclein, both have the ability to form fibrils when incubated at 37° C., and are positive with amyloid stains such as Congo red (demonstrating a red/green birefringence when viewed under polarized light) and Thioflavin S (demonstrating positive fluorescence) (Hashimoto et al., *Brain Res.* 799:301-306, 1998; Ueda et al., *Proc. Natl. Acad. Sci. USA* 90:11282-11286, 1993).

Synucleins are a family of small, presynaptic neuronal proteins composed of α-, β-, and γ-synucleins, of which only α-synuclein aggregates have been associated with several neurological diseases (Ian et al., *Clinical Neurosc. Res.* 1:445-455, 2001; Trojanowski and Lee, *Neurotoxicology* 23:457-460, 2002). The role of synucleins (and in particular, alpha-synuclein) in the etiology of a number of neurodegenerative diseases has developed from several observations. Pathologically, synuclein was identified as a major component of Lewy bodies, the hallmark inclusions of Parkinson's disease, and a fragment thereof was isolated from amyloid plaques of a different neurological disease, Alzheimer's disease. Biochemically, recombinant α-synuclein was shown to form fibrils that recapitulated the ultrastructural features of alpha-synuclein isolated from patients with dementia with Lewy bodies, Parkinson's disease and multiple system atrophy. Additionally, the identification of mutations within the synuclein gene, albeit in rare cases of familial Parkinson's disease, demonstrated an unequivocal link between synuclein pathology and neurodegenerative diseases. The common involvement of α-synuclein in a spectrum of diseases such as Parkinson's disease, dementia with Lewy bodies, multiple system atrophy and the Lewy body variant of Alzheimer's disease has led to the classification of these diseases under the umbrella term of "synucleinopathies".

Parkinson's disease α-synuclein fibrils, and the Aβ fibrils of Alzheimer's disease, both consist of a predominantly β-pleated sheet structure. Compounds found to inhibit Alzheimer's disease Aβ amyloid fibril formation have also been shown to be effective in the inhibition of α-synuclein fibril formation, as illustrated in the Examples of the present invention. These compounds would therefore also serve as therapeutics for Parkinson's disease and other synucleinopathies, in addition to having efficacy as a therapeutic for Alzheimer's disease.

Parkinson's disease and Alzheimer's disease are characterized by the inappropriate accumulation of insoluble aggregates comprised primarily of misfolded proteins that are enriched in β-pleated sheet secondary structure (reviewed in Cohen et al., *Nature* 426:905-909, 2003; Chiti et al., *Annu. Rev. Biochem.*, 75:333-366, 2006). In Parkinson's disease, α-synuclein is the major constituent of these aggregates, as part of Lewy Bodies, and mutations in α-synuclein that increase its propensity to misfold and aggregate are observed in familial Parkinson's disease (Polymeropoulos et al., *Science* 276:1197-1199, 1997; Papadimitriou et al., *Neurology* 52:651-654, 1999).

Mitochondrial dysfunction, specifically as a result of impairment at complex I of the electron transport chain, is also a common feature of Parkinson's disease (Schapira et al., *J. Neurochem.*, 54:823-827, 1990; reviewed in Greenamyre et al., *IUBMB Life*, 52:135-141, 2001). Direct evidence for mitochondrial deficits in the etiology of Parkinson's disease came first from the observation that MPP+ (1-methyl-4-phenyl-2,3-dihydropyridinium), the active metabolite of the parkinsonism toxin N-methyl-4-phenyl-1,2,3,6-tetrahydropyridine (MPTP), inhibits complex I (Nicklas et al., *Life Sci.,*

36:2503-2508, 1985). Subsequently, rotenone, another complex I inhibitor, was shown to be an improved model for α-synuclein aggregation because it reproduces the abovementioned α-synuclein-positive intracytoplasmic aggregates, in addition to the behavioral changes and loss of dopaminergic neurons seen in the MPTP model. Rotenone toxicity of this type is seen in multiple model systems including rats (Betarbet et al., *Nat. Neurosci.*, 3:1301-1306, 2000; Panov et al., *J. Biol. Chem.*, 280:42026-42035, 2005), rat brain slices (Sherer et al., *J. Neurosci.*, 23:10756-10764, 2003; Testa et al., *Mol. Brain. Res.*, 134:109-118, 2005), *C. elegans* (Ved et al., *J. Biol. Chem.*, 280:42655-42668, 2005) and cultured cells (Sherer et al., *J. Neurosci.*, 22:7006-7015, 2002) and has been shown to be a consequence of increased oxidative damage resulting from complex I inhibition.

To better understand the relationship of oxidative damage to mutant α-synuclein pathogenesis, a neuroblastoma cell line (using BE-M17 cells) has been established in the art that overexpresses A53T α-synuclein. In these cells, A53T α-synuclein aggregates in response to a variety of oxidative stress-inducing agents and potentiates mitochondrial dysfunction and cell death (Ostrerova-Golts et al., *J. Neurosci.*, 20:6048-6054, 2000). These cells are amenable to rotenone treatment as an oxidative stress inducer and hence, are particularly useful for testing agents that might inhibit α-synuclein aggregation/fibrillogenesis.

Discovery and identification of new compounds or agents as potential therapeutics to arrest amyloid formation, deposition, accumulation and/or persistence that occurs in Alzheimer's disease, and Parkinson's disease, are desperately sought.

SUMMARY OF THE INVENTION

This invention relates to bis-dihydroxyaryl compounds and pharmaceutically acceptable salts thereof. The compounds are useful in the treatment of β-amyloid diseases and synucleinopathies.

The compounds are:
compounds of the formula:

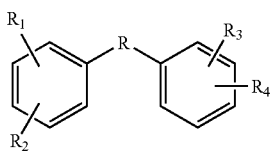

where:
where $R_1$ and $R_2$, and $R_3$ and $R_4$ are hydroxyl groups independently positioned at one of the positions selected from the group consisting of 2,3; 2,4; 2,5; 2,6; 3,5; 3,6; 4,5; 4,6 and 5,6, and R is selected from a sulfonamide, heteroaryl, tricycloalkyl and —C(O)NR' where R' is selected from H or $CH_3$ or pharmaceutically acceptable esters or salts thereof.

Also provided are any pharmaceutically-acceptable derivatives, including salts, esters, enol ethers or esters, acetals, ketals, orthoesters, hemiacetals, hemiketals, solvates, hydrates or prodrugs of the compounds. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine, tris(hydroxymethyl)aminomethane, alkali metal salts, such as but not limited to lithium, potassium and sodium, alkali earth metal salts, such as but not limited to barium, calcium and magnesium, transition metal salts, such as but not limited to zinc and other metal salts, such as but not limited to sodium hydrogen phosphate and disodium phosphate, and also including, but not limited to, salts of mineral acids, such as but not limited to hydrochlorides and sulfates, salts of organic acids, such as but not limited to acetates, lactates, malates, tartrates, citrates, ascorbates, succinates, butyrates, valerates and fumarates.

Pharmaceutical formulations for administration by an appropriate route and means containing effective concentrations of one or more of the compounds provided herein or pharmaceutically acceptable derivatives, such as salts, esters, enol ethers or esters, acetals, ketals, orthoesters, hemiacetals, hemiketals, solvates, hydrates or prodrugs, of the compounds that deliver amounts effective for the treatment of amyloid diseases, are also provided.

The formulations are compositions suitable for administration by any desired route and include solutions, suspensions, emulsions, tablets, dispersible tablets, pills, capsules, powders, dry powders for inhalation, sustained release formulations, aerosols for nasal and respiratory delivery, patches for transdermal delivery and any other suitable route. The compositions should be suitable for oral administration, parenteral administration by injection, including subcutaneously, intramuscularly or intravenously as an injectable aqueous or oily solution or emulsion, transdermal administration and other selected routes.

Methods using such compounds and compositions for disrupting, disaggregating and causing removal, reduction or clearance of β-amyloid or α-synuclein fibrils are provided thereby providing new treatments for β-amyloid diseases and synucleinopathies.

Also provided are methods for treatment, prevention or amelioration of one or more symptoms of amyloid diseases or amyloidoses, including but not limited to diseases associated with the formation, deposition, accumulation, or persistence of β-amyloid fibrils.

Methods for treatment of amyloid diseases, include, but are not limited to Alzheimer's disease, Down's syndrome, hereditary cerebral hemorrhage with amyloidosis of the Dutch type, and cerebral β-amyloid angiopathy.

Also provided are methods for treatment, prevention or amelioration of one or more symptoms of synuclein diseases or synucleinopathies. In one embodiment, the methods inhibit or prevent α-synuclein fibril formation, inhibit or prevent α-synuclein fibril growth, and/or cause disassembly, disruption, and/or disaggregation of preformed α-synuclein fibrils and α-synuclein-associated protein deposits. Synuclein diseases include, but are not limited to Parkinson's disease, familial Parkinson's disease, Lewy body disease, the Lewy body variant of Alzheimer's disease, dementia with Lewy bodies, multiple system atrophy, and the Parkinsonism-dementia complex of Guam.

BRIEF DESCRIPTION OF THE DRAWINGS

FIG. 9A is vehicle alone, FIG. 9B is 1 μM rotenone, FIG. 9C is 5 μM at low magnification, and FIG. 9D is 5 μM at high magnification. FIG. 9E summarizes the quantitative analysis of the Thioflavin S in response to rotenone treatment.

FIG. 10 A is untreated, FIG. 10 B shows 500 ng/mL of positive control compound and FIG. 10 C shows 1 μg/mL positive control compound. FIG. 10D summarizes the quantitative analysis of dose dependent reduction in aggregation.

FIG. 11 A is untreated (rotenone only), and FIGS. 11 B-D, respectively, show 500 ng/mL, 1 μg/mL and 2 μg/mL of compound 1. FIG. 11D summarizes the quantitative analysis of the effects of the compound 1.

FIG. 11E shows graphically the abundance of rotenone-induced aggregates at 1 and 5 μM doses.

FIG. 12 A is untreated (rotenone only), and FIGS. 12 B-D, respectively, show 500 ng/mL, 1 μg/mL and 2 μg/mL of compound 2. FIG. 12E summarizes the quantitative analysis of the anti-aggregation effects of compound 2.

FIG. 13 A is untreated (rotenone only), and FIGS. 13 B-D, respectively, show 500 ng/mL, 1 μg/mL and 2 μg/mL of compound 3. FIG. 13 E summarizes the quantitative analysis of the anti-aggregation effects of compound 3.

FIG. 14 A is untreated (rotenone only), and FIGS. 14 B-D, respectively, show 500 ng/mL, 1 μg/mL and 2 μg/mL of compound 4. FIG. 14 E summarizes the quantitative analysis of the effects of compound 4.

FIG. 15 A is untreated (rotenone only), and FIGS. 15 B-D, respectively, show 500 ng/mL, 1 μg/mL and 2 μg/mL of compound 5. FIG. 15 E summarizes the quantitative analysis of the anti-aggregation effects of compound 5.

FIG. 16 A is untreated (rotenone only), and FIGS. 16 B-D, respectively, show 500 ng/mL, 1 μg/mL and 2 μg/mL of compound 6. FIG. 16 E summarizes the quantitative analysis of the effects of compound 6.

FIG. 17 A is untreated (rotenone only), and FIGS. 17 B-C respectively show 500 ng/mL, and 2 μg/mL of compound 7. FIG. 17 D summarizes the quantitative analysis of the anti-aggregation effects of compound 7.

FIG. 18 A is untreated (rotenone only), and FIGS. 18 B-D, respectively, show 500 ng/mL, 1 μg/mL and 2 μg/mL of compound 8. FIG. 18 E summarizes the quantitative analysis of the anti-aggregation effects of compound 8.

FIG. 19 A is untreated (rotenone only), and FIGS. 19 B-D, respectively, show 500 ng/mL, 1 μg/mL and 2 μg/mL of compound 9. FIG. 19 E summarizes the quantitative analysis of the anti-aggregation effects of compound 9 where * $p<0.05$ relative to 1 μM rotenone only.

FIG. 22 B is a graph showing the ability of compound 1 to protect against rotenone-induced toxicity as measured by the XTT Cytotoxicity assay.

FIG. 23 B is a graph showing the ability of compound 2 to protect against rotenone-induced toxicity as measured by the XTT Cytotoxicity assay.

FIG. 24 B is a graph showing the ability of compound 3 to protect against rotenone-induced toxicity as measured by the XTT Cytotoxicity assay.

FIG. 25 B is a graph showing the ability of compound 4 to protect against rotenone-induced toxicity as measured by the XTT Cytotoxicity assay.

FIG. 26 B is a graph showing the inability of compound 5 to protect against rotenone-induced toxicity as measured by the XTT Cytotoxicity assay.

FIG. 27 B is a graph showing the ability of compound 6 to protect against rotenone-induced toxicity as measured by the XTT Cytotoxicity assay.

FIG. 28 B is a graph showing the ability of compound 7 to protect against rotenone-induced toxicity as measured by the XTT Cytotoxicity assay.

FIG. 29 B is a graph showing the ability of compound 8 to protect against rotenone-induced toxicity as measured by the XTT Cytotoxicity assay.

FIG. 30 B is a graph showing the inability of compound 9 to protect against rotenone-induced toxicity as measured by the XTT Cytotoxicity assay.

DETAILED DESCRIPTION OF THE INVENTION

Definitions

Figure 1:
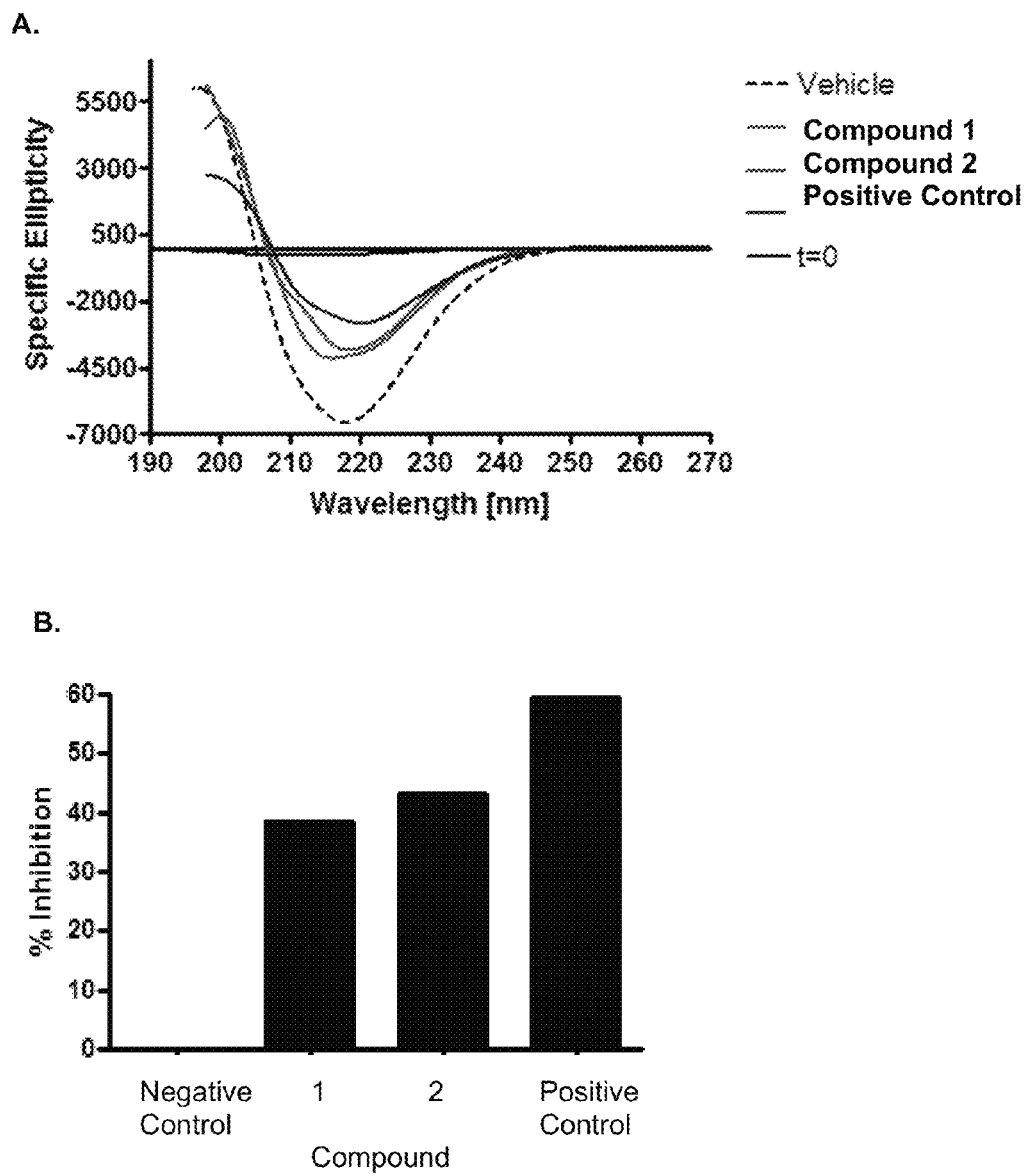
FIG. 1A shows several circular dichroism spectra illustrating that Alzheimer's disease Aβ fibrils are disrupted by the compounds tested at 1:1 wt/wt.
FIG. 1B shows graphically the % inhibition.

In this application, the following terms shall have the following meanings, without regard to whether the terms are used variantly elsewhere in the literature or otherwise in the known art.

As used herein "Amyloid diseases" or "amyloidoses" are diseases associated with the formation, deposition, accumulation, or persistence of Aβ amyloid fibrils. Such diseases include, but are not limited to Alzheimer's disease, Down's syndrome, hereditary cerebral hemorrhage with amyloidosis of the Dutch type, and cerebral β-amyloid angiopathy.

As used herein, "Synuclein diseases" or "synucleinopathies" are diseases associated with the formation, deposition, accumulation, or persistence of α-synuclein fibrils. Such diseases include, but are not limited to Parkinson's disease, familial Parkinson's disease, Lewy body disease, the Lewy body variant of Alzheimer's disease, dementia with Lewy bodies, multiple system atrophy, and the Parkinsonism-dementia complex of Guam.

"Fibrillogenesis" refers to the formation, deposition, accumulation and/or persistence of β-amyloid fibrils, filaments, inclusions, deposits, as well as α-synuclein fibrils, filaments, inclusions, deposits or the like.

"Inhibition of fibrillogenesis" refers to the inhibition of formation, deposition, accumulation and/or persistence of such a β-amyloid fibrils or α-synuclein fibril-like deposits.

"Disruption of fibrils or fibrillogenesis" refers to the disruption of pre-formed β-amyloid or α-synuclein fibrils, that usually exist in a pre-dominant β-pleated sheet secondary structure. Such disruption by compounds provided herein may involve marked reduction or disassembly of amyloid or synuclein fibrils as assessed by various methods such as Thioflavin T fluorometry, Congo red binding, circular dichroism spectra, thioflavin S and cell based assays such as α-synuclein aggregation and XTT cytotoxicity assays and as demonstrated by the Examples presented in this application.

"Neuroprotection" or "neuroprotective" refers to the ability of a compound to protect, reduce, alleviate, ameliorate, and/or attenuate damage to nerve cells (neurodegeneration).

"Mammal" includes both humans and non-human mammals, such as companion animals (cats, dogs, and the like), laboratory animals (such as mice, rats, guinea pigs, and the like) and farm animals (cattle, horses, sheep, goats, swine, and the like).

"Pharmaceutically acceptable excipient" means an excipient that is conventionally useful in preparing a pharmaceutical composition that is generally safe, non-toxic, and desirable, and includes excipients that are acceptable for veterinary use or for human pharmaceutical use. Such excipients may be solid, liquid, semisolid, or, in the case of an aerosol composition, gaseous.

A "therapeutically effective amount" means the amount that, when administered to a subject or animal for treating a disease, is sufficient to affect the desired degree of treatment, prevention or symptom amelioration for the disease. A "therapeutically effective amount" or a "therapeutically effective dosage" in certain embodiments inhibits, reduces, disrupts, disassembles β-amyloid or α-synuclein fibril formation, deposition, accumulation and/or persistence, or treats, prevents, or ameliorates one or more symptoms of a disease associated with these conditions, such as an amyloid disease or a synucleinopathy, in a measurable amount in one embodiment, by at least 20%, in other embodiment, by at least 40%, in other embodiment by at least 60%, and in still other embodiment by at least 80%, relative to an untreated subject. Effective amounts of a compound provided herein or composition thereof for treatment of a mammalian subject are about 0.1 to about 1000 mg/Kg of body weight of the subject/day, such as from about 1 to about 100 mg/Kg/day, in other embodiment, from about 10 to about 500 mg/Kg/day. A broad range of disclosed composition dosages are believed to be both safe and effective.

The term "sustained release component" is defined herein as a compound or compounds, including, but not limited to, polymers, polymer matrices, gels, permeable membranes, liposomes, microspheres, or the like, or a combination thereof, that facilitates the sustained release of the active ingredient.

If the complex is water-soluble, it may be formulated in an appropriate buffer, for example, phosphate buffered saline, or other physiologically compatible solutions. Alternatively, if the resulting complex has poor solubility in aqueous solvents, then it may be formulated with a non-ionic surfactant such as Tween, or polyethylene glycol. Thus, the compounds and their physiological solvents may be formulated for administration by inhalation or insufflation (either through the mouth or the nose) or oral, buccal, parenteral, or rectal administration, as examples.

As used herein, pharmaceutically acceptable derivatives of a compound include salts, esters, enol ethers, enol esters, acetals, ketals, orthoesters, hemiacetals, hemiketals, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment of a disease also includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease), such as by disruption of pre-formed β-amyloid or α-synuclein fibrils.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, inhibition of α-synuclein fibril formation, deposition, accumulation, aggregation, and/or persistence is believed to be effective treatment for a number of diseases involving α-synuclein, such as Parkinson's disease, Lewy body disease and multiple system atrophy.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

Chemical structures for some of the compounds of this invention are shown. The names of the compounds are variously IUPAC names [names derived according to the accepted IUPAC (International Union of Pure and Applied Chemistry) system established by the coalition of the Commission on Nomenclature of Organic Chemistry and the Commission on Physical Organic Chemistry, as can be found at http://www.chem.qmul.ac.uk/iupac], names derived from IUPAC names by addition or substitution (for example, by the use of "3,4-methylenedioxyphenyl" derived from "phenyl" instead of "benzo[1,3]dioxol-5-yl"), and names derived from the names of reactants (for example, by the use of "3,4-dihydroxybenzoic acid 3,4-dihydroxyanilide" instead of "N-(3,4-dihydroxyphenyl)-3,4-dihydroxybenzamide"). However, the names used are explicitly equated to chemical structures, and are believed to be readily understood by a person of ordinary skill in the art.

"A pharmaceutical agent" or "pharmacological agent" or "pharmaceutical composition" refers to a compound or combination of compounds used for treatment, preferably in a pure or near pure form. In the specification, pharmaceutical or pharmacological agents include the compounds of this invention. The compounds are desirably purified to 80% homogeneity, and preferably to 90% homogeneity. Compounds and compositions purified to 99.9% homogeneity are believed to be advantageous. As a test or confirmation, a suitable homogeneous compound on HPLC would yield, what those skilled in the art would identify as a single sharp-peak band.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, alkyl, alkenyl and alkynyl carbon chains, if not specified, contain from 1 to 20 carbons, or 1 or 2 to 16 carbons, and are straight or branched. Alkenyl carbon chains of from 2 to 20 carbons, in certain embodiments, contain 1 to 8 double bonds and alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl). As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "cycloalkyl" refers to a saturated mono- or multi-cyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl. imidazole, triazole and pyrazole.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO— in which R is a haloalkyl group.

As used herein, "sulfinyl" or "thionyl" refers to —S(O)—.
As used herein, "sulfonyl" or "sulfuryl" refers to —S(O)$_2$—.
As used herein, "sulfo" refers to —S(O)$_2$O—.

As used herein, "carboxy" refers to a divalent radical, —C(O)O—.

As used herein, "aminocarbonyl" refers to —C(O)NH$_2$.

As used herein, "alkylaminocarbonyl" refers to —C(O)NHR in which R is alkyl, including lower alkyl.

As used herein, "dialkylaminocarbonyl" refers to —C(O)NR'R in which R' and R are each independently alkyl, including lower alkyl; "carboxamide" refers to groups of formula —NR'COR in which R' and R are each independently alkyl, including lower alkyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O)NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulfur, including S(=O) and S(=O)$_2$ groups, or substituted or unsubstituted nitrogen atoms, including —NR— and —N$^+$RR— groups, where the nitrogen substituent(s) is (are) alkyl, aryl, aralkyl, heteroaryl, heteroaralkyl or COR', where R' is alkyl, aryl, aralkyl, heteroaryl, heteroaralkyl, —OY or —NYY, where Y is hydrogen, alkyl, aryl, heteroaryl, cycloalkyl or heterocyclyl. Alkylene groups include, but are not limited to, methylene (—CH$_2$—), ethylene (—CH$_2$CH$_2$—), propylene (—(CH$_2$)$_3$—), methylenedioxy (—O—CH$_2$—O—) and ethylenedioxy (—O—(CH$_2$)$_2$—O—). The term "lower alkylene" refers to alkylene groups having 1 to 6 carbons. In certain embodiments, alkylene groups are lower alkylene, including alkylene of 1 to 3 carbon atoms.

As used herein, "azaalkylene" refers to —(CRR)$_n$—NR—(CRR)$_m$—, where n and m are each independently an integer from 0 to 4. As used herein, "oxaalkylene" refers to —(CRR)$_n$—O—(CRR)$_m$—, where n and m are each independently an integer from 0 to 4. As used herein, "thiaalkylene"

refers to —(CRR)$_n$—S—(CRR)$_m$—, —(CRR)$_n$—S(=O)—(CRR)$_m$—, and —(CRR)$_n$—S(=O)$_2$—(CRR)$_m$—, where n and m are each independently an integer from 0 to 4.

As used herein, "alkenylene" refers to a straight, branched or cyclic, in one embodiment straight or branched, divalent aliphatic hydrocarbon group, in certain embodiments having from 2 to about 20 carbon atoms and at least one double bond, in other embodiments 1 to 12 carbons. In further embodiments, alkenylene groups include lower alkenylene. There may be optionally inserted along the alkenylene group one or more oxygen, sulfur or substituted or unsubstituted nitrogen atoms, where the nitrogen substituent is alkyl. Alkenylene groups include, but are not limited to, —CH=CH—CH=CH— and —CH=CH—CH$_2$—. The term "lower alkenylene" refers to alkenylene groups having 2 to 6 carbons. In certain embodiments, alkenylene groups are lower alkenylene, including alkenylene of 3 to 4 carbon atoms.

As used herein, "alkynylene" refers to a straight, branched or cyclic, in certain embodiments straight or branched, divalent aliphatic hydrocarbon group, in one embodiment having from 2 to about 20 carbon atoms and at least one triple bond, in another embodiment 1 to 12 carbons. In a further embodiment, alkynylene includes lower alkynylene. There may be optionally inserted along the alkynylene group one or more oxygen, sulfur or substituted or unsubstituted nitrogen atoms, where the nitrogen substituent is alkyl. Alkynylene groups include, but are not limited to, —C≡C—C≡C—, —C≡C— and —C≡C—CH$_2$—. The term "lower alkynylene" refers to alkynylene groups having 2 to 6 carbons. In certain embodiments, alkynylene groups are lower alkynylene, including alkynylene of 3 to 4 carbon atoms.

As used herein, "alk(en)(yn)ylene" refers to a straight, branched or cyclic, in certain embodiments straight or branched, divalent aliphatic hydrocarbon group, in one embodiment having from 2 to about 20 carbon atoms and at least one triple bond, and at least one double bond; in another embodiment 1 to 12 carbons. In further embodiments, alk(en)(yn)ylene includes lower alk(en)(yn)ylene. There may be optionally inserted along the alkynylene group one or more oxygen, sulfur orsubstituted or unsubstituted nitrogen atoms, where the nitrogen substituent is alkyl. Alk(en)(yn)ylene groups include, but are not limited to, —C=C—(CH$_2$)$_n$—C≡C—, where n is 1 or 2. The term "lower alk(en)(yn)ylene" refers to alk(en)(yn)ylene groups having up to 6 carbons. In certain embodiments, alk(en)(yn)ylene groups have about 4 carbon atoms.

As used herein, "cycloalkylene" refers to a divalent saturated mono- or multicyclic ring system, in certain embodiments of 3 to 10 carbon atoms, in other embodiments 3 to 6 carbon atoms; cycloalkenylene and cycloalkynylene refer to divalent mono- or multicyclic ring systems that respectively include at least one double bond and at least one triple bond. Cycloalkenylene and cycloalkynylene groups may, in certain embodiments, contain 3 to 10 carbon atoms, with cycloalkenylene groups in certain embodiments containing 4 to 7 carbon atoms and cycloalkynylene groups in certain embodiments containing 8 to 10 carbon atoms. The ring systems of the cycloalkylene, cycloalkenylene and cycloalkynylene groups may be composed of one ring or two or more rings which may be joined together in a fused, bridged or spiro-connected fashion. "Cycloalk(en)(yn)ylene" refers to a cycloalkylene group containing at least one double bond and at least one triple bond.

As used herein, "arylene" refers to a monocyclic or polycyclic, in certain embodiments monocyclic, divalent aromatic group, in one embodiment having from 5 to about 20 carbon atoms and at least one aromatic ring, in another embodiment 5 to 12 carbons. In further embodiments, arylene includes lower arylene. Arylene groups include, but are not limited to, 1,2-, 1,3- and 1,4-phenylene. The term "lower arylene" refers to arylene groups having 6 carbons.

As used herein, "heteroarylene" refers to a divalent monocyclic or multicyclic aromatic ring system, in one embodiment of about 5 to about 15 atoms in the ring(s), where one or more, in certain embodiments 1 to 3, of the atoms in the ring system is a heteroatom, that is, an element other than carbon, including but not limited to, nitrogen, oxygen or sulfur. The term "lower heteroarylene" refers to heteroarylene groups having 5 or 6 atoms in the ring.

As used herein, "heterocyclylene" refers to a divalent monocyclic or multicyclic non-aromatic ring system, in certain embodiments of 3 to 10 members, in one embodiment 4 to 7 members, in another embodiment 5 to 6 members, where one or more, including 1 to 3, of the atoms in the ring system is a heteroatom, that is, an element other than carbon, including but not limited to, nitrogen, oxygen or sulfur.

As used herein, "substituted alkyl," "substituted alkenyl," "substituted alkynyl," "substituted cycloalkyl," "substituted cycloalkenyl," "substituted cycloalkynyl," "substituted aryl," "substituted heteroaryl," "substituted heterocyclyl," "substituted alkylene," "substituted alkenylene," "substituted alkynylene," "substituted cycloalkylene," "substituted cycloalkenylene," "substituted cycloalkynylene," "substituted arylene," "substituted heteroarylene" and "substituted heterocyclylene" refer to alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene and heterocyclylene groups, respectively, that are substituted with one or more substituents, in certain embodiments one, two, three or four substituents, where the substituents are as defined herein, in one embodiment selected from $Q^1$.

As used herein, "alkylidene" refers to a divalent group, such as =CR'R", which is attached to one atom of another group, forming a double bond. Alkylidene groups include, but are not limited to, methylidene (=CH$_2$) and ethylidene (=CHCH$_3$). As used herein, "arylalkylidene" refers to an alkylidene group in which either R' or R" is an aryl group. "Cycloalkylidene" groups are those where R' and R" are linked to form a carbocyclic ring. "Heterocyclylidene" groups are those where at least one of R' and R" contain a heteroatom in the chain, and R' and R" are linked to form a heterocyclic ring.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —NC(S)NH—.

As used herein, "semicarbazide" refers to —NHC(O)NHNH—. "Carbazate" refers to the divalent group —OC(O)NHNH—. "Isothiocarbazate" refers to the divalent group —SC(O)NHNH—. "Thiocarbazate" refers to the divalent group —OC(S)NHNH—. "Sulfonylhydrazide" refers to the divalent group —SO$_2$NHNH—. "Hydrazide" refers to the divalent group —C(O)NHNH—. "Azo" refers to the divalent group —N=N—. "Hydrazinyl" refers to the divalent group —NH—NH—.

As used herein, "sulfonamide" refers to —RSO$_2$NH$_2$— a sulfone group connected to an amine group.

As used herein, "imidazole" refers to a heterocyclic aromatic organic compound having a general formula of $C_3H_4N_2$.

As used herein, "triazole" refers to either one of a pair of isomeric chemical compounds with molecular formula of $C_2H_3N_3$.

As used herein, "pyrazole" refers to a heterocyclic 5-membered ring composed of three carbons and two nitrogen atoms in adjacent positions.

As used herein, "adamantane" refers to a tricycloalkyl having a general formula of $C_{10}H_{16}$.

Where the number of any given substituent is not specified (e.g., haloalkyl), there may be one or more substituents present. For example, "haloalkyl" may include one or more of the same or different halogens. As another example, "$C_{1-3}$ alkoxyphenyl" may include one or more of the same or different alkoxy groups containing one, two or three carbons.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

Compounds of the Invention

The compounds of this invention are:

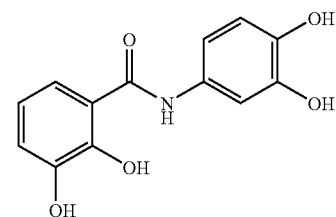 [SMILES: O=C(Nc1ccc(O)c(O)c1)c1cccc(O)c1O]

2,3 dihydroxybenzoic acid 3,4 dihydroxyanilide (Compound 1),

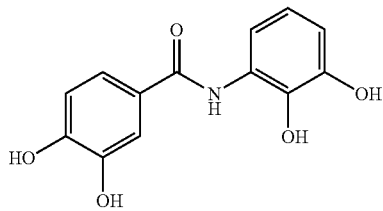 [SMILES: O=C(Nc1cccc(O)c1O)c1ccc(O)c(O)c1]

3,4 dihydroxybenzoic acid 2,3 dihydroxyanilide (Compound 2),

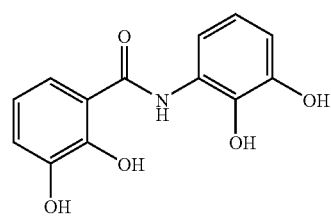 [SMILES: O=C(Nc1cccc(O)c1O)c1cccc(O)c1O]

2,3 dihydroxybenzoic acid 2,3 dihydroxyanilide (Compound 3),

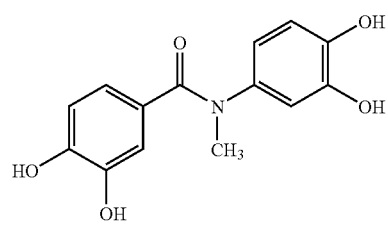 [SMILES: CN(C(=O)c1ccc(O)c(O)c1)c1ccc(O)c(O)c1]

3,4 dihydroxybenzoic acid 3,4 dihydroxy N-methyl anilide (Compound 4),

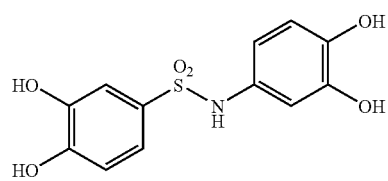 [SMILES: O=S(=O)(Nc1ccc(O)c(O)c1)c1ccc(O)c(O)c1]

3,4 dihydroxybenzenesulfonic acid 3,4 dihydroxyphenylsulfonamide (Compound 5),

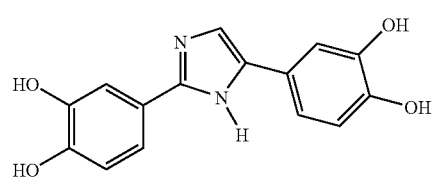 [SMILES: Oc1ccc(-c2cnc(-c3ccc(O)c(O)c3)[nH]2)cc1O]

2,4 bis(3,4 dihydroxyphenyl)imidazole (Compound 6),

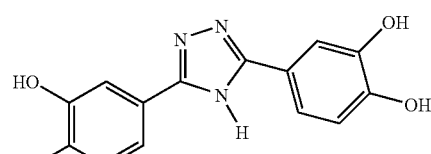

3,5 bis(3,4 dihydroxyphenyl) 1,2,4 triazole (Compound 7),

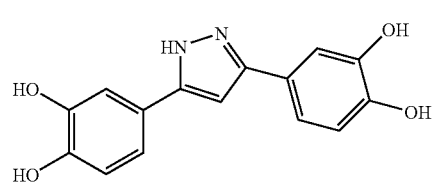 [SMILES: Oc1ccc(-c2cc(-c3ccc(O)c(O)c3)[nH]n2)cc1O]

3,5 bis(3,4 dihydroxyphenyl)pyrazole (Compound 8),

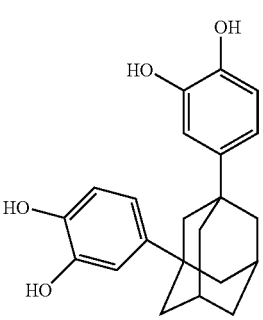 [SMILES: Oc1ccc(C23CC4CC(C2)CC(c2ccc(O)c(O)c2)(C4)C3)cc1O]

1,3 bis(3,4 dihydroxyphenyl)adamantane (Compound 9),

Synthesis of the Compounds of the Invention

The compounds of this invention may be prepared by methods generally known to the person of ordinary skill in the art, having regard to that knowledge and the disclosure of this application including Examples 1-5.

The starting materials and reagents used in preparing these compounds are either available from commercial suppliers such as the Aldrich Chemical Company (Milwaukee, Wis.), Bachem (Torrance, Calif.), Sigma (St. Louis, Mo.), or Lancaster Synthesis Inc. (Windham, N.H.) or are prepared by methods well known to a person of ordinary skill in the art, following procedures described in such references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In most cases, protective groups for the hydroxy groups are introduced and finally removed. Suitable protective groups are described in Greene et al., *Protective Groups in Organic Synthesis*, Second Edition, John Wiley and Sons, New York, 1991. Other starting materials or early intermediates may be prepared by elaboration of the materials listed above, for example, by methods well known to a person of ordinary skill in the art.

The starting materials, intermediates, and compounds of this invention may be isolated and purified using conventional techniques, including precipitation, filtration, distillation, crystallization, chromatography, and the like. The compounds may be characterized using conventional methods, including physical constants and spectroscopic methods.

Pharmacology and Utility

The compounds provided herein can be used as such, be administered in the form of pharmaceutically acceptable salts derived from inorganic or organic acids, or used in combination with one or more pharmaceutically acceptable excipients. The phrase "pharmaceutically acceptable salt" means those salts which are, within the scope of sound medical judgment, suitable for use in contact with the tissues without undue toxicity, irritation, allergic response, and the like, and are commensurate with a reasonable benefit/risk ratio. Pharmaceutically acceptable salts are well known in the art. The salts can be prepared either in situ during the final isolation and purification of the compounds provided herein or separately by reacting the acidic or basic drug substance with a suitable base or acid respectively. Typical salts derived from organic or inorganic acids salts include, but are not limited to hydrochloride, hydrobromide, hydroiodide, acetate, adipate, alginate, citrate, aspartate, benzoate, bisulfate, gluconate, fumarate, hydroiodide, lactate, maleate, oxalate, palmitoate, pectinate, succinate, tartrate, phosphate, glutamate, and bicarbonate. Typical salts derived from organic or inorganic bases include, but are not limited to lithium, sodium, potassium, calcium, magnesium, ammonium, monoalkylammonium such as meglumine, dialkylammonium, trialkylammonium, and tetralkylammonium.

Actual dosage levels of active ingredients and the mode of administration of the pharmaceutical compositions provided herein can be varied in order to achieve the effective therapeutic response for a particular patient. The phrase "therapeutically effective amount" of the compound provided herein means a sufficient amount of the compound to treat disorders, at a reasonable benefit/risk ratio applicable to any medical treatment. It will be understood, however, that the total daily usage of the compounds and compositions of the provided will be decided by the attending physician within the scope of sound medical judgment. The total daily dose of the compounds provided herein may range from about 0.1 to about 1000 mg/kg/day. For purposes of oral administration, doses can be in the range from about 1 to about 500 mg/kg/day. If desired, the effective daily dose can be divided into multiple doses for purposes of administration; consequently, single dose compositions may contain such amounts or submultiples thereof to make up the daily dose. The specific therapeutically effective dose level for any particular patient will depend upon a variety of factors including the disorder being treated and the severity of the disorder; medical history of the patient, activity of the specific compound employed; the specific composition employed, age, body weight, general health, sex and diet of the patient, the time of administration, route of administration, the duration of the treatment, rate of excretion of the specific compound employed, drugs used in combination or coincidental with the specific compound employed; and the like.

The compounds provided can be formulated together with one or more non-toxic pharmaceutically acceptable diluents, carriers, adjuvants, and antibacterial and antifungal agents such as parabens, chlorobutanol, phenol, sorbic acid, and the like. Proper fluidity can be maintained, for example, by the use of coating materials such as lecithin, by the maintenance of the required particle size in the case of dispersions, and by the use of surfactants. In some cases, in order to prolong the effect of the drug, it is desirable to decrease the rate of absorption of the drug from subcutaneous or intramuscular injection. This can be accomplished by suspending crystalline or amorphous drug substance in a vehicle having poor water solubility such as oils. The rate of absorption of the drug then depends upon its rate of dissolution, which, in turn, may depend upon crystal size and crystalline form. Prolonged absorption of an injectable pharmaceutical form can be achieved by the use of absorption delaying agents such as aluminum monostearate or gelatin.

The compound provided herein can be administered enterally or parenterally in solid or liquid forms. Compositions suitable for parenteral injection may comprise physiologically acceptable, isotonic sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar and tragacanth, or mixtures of these substances.

The compounds provided herein can also be administered by injection or infusion, either subcutaneously or intravenously, or intramuscularly, or intrasternally, or intranasally, or by infusion techniques in the form of sterile injectable or oleaginous suspension. The compound may be in the form of a sterile injectable aqueous or oleaginous suspensions. These suspensions may be formulated according to the known art using suitable dispersing of wetting agents and suspending agents that have been described above. The sterile injectable preparation may also be a sterile injectable solution or suspension in a non-toxic parenterally-acceptable diluent or solvent for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oils may be conventionally employed including synthetic mono- or diglycerides. In addition fatty acids such as oleic acid find use in the preparation of injectables. Dosage regimens can be adjusted to provide the optimum therapeutic response. For example, several divided dosages may be administered daily or the dosage may be proportionally reduced as indicated by the exigencies of the therapeutic situation.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or (a) fillers or extenders such as starches, lactose, sucrose, glucose, mannitol and silicic acid; (b) binders such as carboxymethylcellulose, alginates, gelatin, polyvinylpyrrolidone, sucrose and acacia; (c) humectants such as glycerol; (d) disintegrating agents such as agar-agar, calcium carbonate, potato or tapioca starch, alginic acid, certain silicates and sodium carbonate; (e) solution retarding agents such as paraffin; (f) absorption accelerators such as quaternary ammonium compounds; (g) wetting agents such as cetyl alcohol and glycerol monostearate; (h) absorbents such as kaolin and bentonite clay and (i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes. Tablets contain the compound in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, maize starch or alginic acid; binding agents, for example, maize starch, gelatin or acacia, and lubricating agents, for example, magnesium stearate or stearic acid or talc. The tablets may be uncoated or they may be coated by known techniques to delay disintegration and absorption in the gastrointestinal tract and thereby provide a sustained action over a longer period. For example, a time delay material such as glycerol monostearate or glycerol distearate may be employed. Formulations for oral use may also be presented as hard gelatin capsules wherein the compound is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents.

Aqueous suspensions contain the compound in admixture with excipients suitable for the manufacture of aqueous suspensions. Such excipients are suspending agents, for example, sodium carboxymethylcellulose, methylcellulose, hydroxypropylmethyl cellulose, sodium alginate, polyvinylpyrrolidone, gum tragacanth and gum acacia; dispersing or wetting agents may be naturally occurring phosphatides, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids such as hexitol such as polyoxyethylene sorbitol monooleate, or condensation products of ethylene oxide with partial esters from fatty acids and a hexitol anhydrides, for example, polyethylene sorbitan monooleate. The aqueous suspensions may also contain one or more preservatives, for example, ethyl or n-propyl p-hydroxybenzoate, one or more coloring agents, one or more flavoring agents, or one or more sweetening agents, such as sucrose or saccharin.

Oily suspensions may be formulated by suspending the compound in a vegetable oil, for example arachis oil, olive oil, sesame oil, or coconut oil or in a mineral oil such as liquid paraffin. The oily suspensions may contain a thickening agent, for example beeswax, hard paraffin or cetyl alcohol. Sweetening agents, such as those set forth below, and flavoring agents may be added to provide a palatable oral preparation. These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already described above. Additional excipients, for example sweetening, flavoring and agents, may also be present.

The compounds provided herein may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean, lecithin, and occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsion may also contain sweetening and flavoring agents. Syrups and elixirs may be formulated with sweetening agents, for example, glycerol, sorbitol or sucrose. Such formulations may also contain a demulcent, a preservative and flavoring and coloring agents.

In one embodiment, the compounds are formulated in dosage unit form for ease of administration and uniformity of dosage. Dosage unit form as used herein refers to physically discrete units suited as unitary dosages for the subjects to be treated; each containing a therapeutically effective quantity of the compound and at least one pharmaceutical excipient. A drug product will comprise a dosage unit form within a container that is labeled or accompanied by a label indicating the intended method of treatment, such as the treatment of an β-amyloid disease, for example an amyloidosis such as Alzheimer's disease or a disease associated with α-synuclein fibril formation such as Parkinson's disease. Compositions for rectal or vaginal administration are preferably suppositories which can be prepared by mixing the compounds provided herein with suitable non-irritating excipients or carriers such as cocoa butter, polyethylene glycol or a suppository wax which are solid at room temperature but liquid at body temperature and therefore melt in the rectum or vaginal cavity and release the active compound.

Compounds provided herein can also be administered in the form of liposomes. Methods to form liposomes are known in the art (Prescott, Ed., *Methods in Cell Biology* 1976, Volume XIV, Academic Press, New York, N.Y.) As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound provided herein, stabilizers, preservatives, excipients and the like. The preferred lipids are natural and synthetic phospholipids and phosphatidyl cholines (lecithins).

The compounds provided herein can also be administered in the form of a 'prodrug' wherein the active pharmaceutical ingredients, are released in vivo upon contact with hydrolytic enzymes such as esterases and phophatases in the body. The term "pharmaceutically acceptable prodrugs" as used herein represents those prodrugs of the compounds provided herein, which are, within the scope of sound medical judgment, suitable for use in contact with the tissues without undue toxicity, irritation, allergic response, and the like, commensurate with a reasonable benefit/risk ratio, and effective for their intended use. A thorough discussion is provided in T. Higuchi and V. Stella (Higuchi, T. and Stella, V. Pro-drugs as Novel Delivery Systems, V. 14 of the A.C.S. Symposium Series; Edward B. Roche, Ed., *Bioreversible Carriers in Drug Design* 1987, American Pharmaceutical Association and Pergamon Press), which is incorporated herein by reference.

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Sustained Release Formulations

The invention also includes the use of sustained release formulations to deliver the compounds of the present invention to the desired target (i.e. brain or systemic organs) at high circulating levels (between $10^{-9}$ and $10^{-4}$ M) are also disclosed. In a preferred embodiment for the treatment of Alzheimer's or Parkinson's disease, the circulating levels of the compounds is maintained up to $10^{-7}$ M. The levels are either circulating in the patient systemically, or in a preferred embodiment, present in brain tissue, and in a most preferred embodiments, localized to the β-amyloid or α-synuclein fibril deposits in brain or other tissues.

It is understood that the compound levels are maintained over a certain period of time as is desired and can be easily determined by one skilled in the art using this disclosure and compounds of the invention. In a preferred embodiment, the invention includes a unique feature of administration comprising a sustained release formulation so that a constant level of therapeutic compound is maintained between $10^{-8}$ and $10^{-6}$ M between 48 to 96 hours in the sera.

Such sustained and/or timed release formulations may be made by sustained release means of delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556 and 5,733,566, the disclosures of which are each incorporated herein by reference. These pharmaceutical compositions can be used to provide slow or sustained release of one or more of the active compounds using, for example, hydroxypropylmethyl cellulose, other polymer matrices, gels, permeable membranes, osmotic systems, multilayer coatings, microparticles, liposomes, microspheres, or the like. Suitable sustained release formulations known to those skilled in the art, including those described herein, may be readily selected for use with the pharmaceutical compositions of the invention. Thus, single unit dosage forms suitable for oral administration, such as, but not limited to, tablets, capsules, gelcaps, caplets, powders and the like, that are adapted for sustained release are encompassed by the present invention.

In a preferred embodiment, the sustained release formulation contains active compound such as, but not limited to, microcrystalline cellulose, maltodextrin, ethylcellulose, and magnesium stearate. As described above, all known methods for encapsulation which are compatible with properties of the disclosed compounds are encompassed by this invention. The sustained release formulation is encapsulated by coating particles or granules of the pharmaceutical composition of the invention with varying thickness of slowly soluble polymers or by microencapsulation. In a preferred embodiment, the sustained release formulation is encapsulated with a coating material of varying thickness (e.g. about 1 micron to 200 microns) that allow the dissolution of the pharmaceutical composition about 48 hours to about 72 hours after administration to a mammal. In another embodiment, the coating material is a food-approved additive.

In another embodiment, the sustained release formulation is a matrix dissolution device that is prepared by compressing the drug with a slowly soluble polymer carrier into a tablet. In one preferred embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, having a relatively high percentage of plasticizer in the coating in order to permit sufficient flexibility to prevent substantial breakage during compression are disclosed. The specific amount of plasticizer varies depending on the nature of the coating and the particular plasticizer used. The amount may be readily determined empirically by testing the release characteristics of the tablets formed. If the medicament is released too quickly, then more plasticizer is used. Release characteristics are also a function of the thickness of the coating. When substantial amounts of plasticizer are used, the sustained release capacity of the coating diminishes. Thus, the thickness of the coating may be increased slightly to make up for an increase in the amount of plasticizer. Generally, the plasticizer in such an embodiment will be present in an amount of about 15 to 30% of the sustained release material in the coating, preferably 20 to 25%, and the amount of coating will be from 10 to 25% of the weight of the active material, preferably 15 to 20%. Any conventional pharmaceutically acceptable plasticizer may be incorporated into the coating.

The compounds of the invention can be formulated as a sustained and/or timed release formulation. All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: 1) extended activity of the composition, 2) reduced dosage frequency, and 3) increased patient compliance. In addition, sustained release formulations can be used to affect the time of onset of action or other characteristics, such as blood levels of the composition, and thus can affect the occurrence of side effects.

The sustained release formulations of the invention are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds. The term "sustained release component" in the context of the present invention is defined herein as a compound or compounds, including, but not limited to, polymers, polymer matrices, gels, permeable membranes, liposomes, microspheres, or the like, or a combination thereof, that facilitates the sustained release of the active ingredient.

If the complex is water-soluble, it may be formulated in an appropriate buffer, for example, phosphate buffered saline, or other physiologically compatible solutions. Alternatively, if the resulting complex has poor solubility in aqueous solvents, then it may be formulated with a non-ionic surfactant such as Tween, or polyethylene glycol. Thus, the compounds and their physiologically solvents may be formulated for administration by inhalation or insufflation (either through the mouth or the nose) or oral, buccal, parenteral, or rectal administration, as examples.

Preparations for oral administration may be suitably formulated to give controlled release of the active compound. In a preferred embodiment, the compounds of the present invention are formulated as controlled release powders of discrete microparticles that can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33-45 of U.S. Pat. No. 5,354,556, which is incorporated by reference in its entirety. Particularly suitable polymers include those described, but not limited to those described in column 3, line 46-column 4, line 8 of U.S. Pat. No. 5,354,556 which is incorporated by reference in its entirety.

The sustained release compounds of the invention may be formulated for parenteral administration, e.g., by intramuscular injections or implants for subcutaneous tissues and various body cavities and transdermal devices. In one embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil suspensions and solutions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachis, maize, almond, soybean, cottonseed and castor oil.

A highly developed form of drug delivery that imparts sustained release over periods of time ranging from days to years is to implant a drug-bearing polymeric device subcutaneously or in various body cavities. The polymer material used in an implant, which must be biocompatible and non-toxic, include but are not limited to hydrogels, silicones, polyethylenes, ethylene-vinyl acetate copolymers, or biodegradable polymers.

Evaluation of the Activity of the Compounds

The biological activity of the compounds provided herein as disruptors/inhibitors of Alzheimer's disease β-amyloid protein (Aβ) fibrils, and Parkinson's disease α-synuclein fibrils was assessed by determining the efficacy of the compounds to cause a disassembly/disruption of pre-formed amyloid fibrils of Alzheimer's disease (i.e. consisting of Aβ 1-42 fibrils), and Parkinson's disease α-synuclein fibrils. In one study, Thioflavin T fluorometry was used to determine the effects of the compounds, and of EDTA (as a negative control). In this assay Thioflavin T binds specifically to fibrillar amyloid, and this binding produces a fluorescence enhancement at 485 nm that is directly proportional to the amount of fibrils present. The higher the fluorescence, the greater the amount of fibrils present (Naki et al, *Lab. Invest.* 65:104-110, 1991; Levine III, *Protein Sci.* 2:404-410, 1993; *Amyloid: Int. J. Exp. Clin. Invest.* 2:1-6, 1995).

In the Congo red binding assay the ability of a given test compound to alter amyloid (Aβ1-42 fibrils, or α-synuclein fibrils) binding to Congo red was quantified. In this assay, Aβ 1-42 fibrils, or α-synuclein fibrils and test compounds were incubated for 3 days and then vacuum filtered through a 0.2 μm filter. The amount of Aβ 1-42 fibrils, or α-synuclein fibrils retained in the filter was then quantitated following staining of the filter with Congo red. After appropriate washing of the filter, any lowering of the Congo red color on the filter in the presence of the test compound (compared to the Congo red staining of the amyloid protein in the absence of the test compound) was indicative of the test compound's ability to diminish/alter the amount of aggregated and congophilic Aβ 1-42 fibrils, or α-synuclein fibrils.

Combination Therapy

In another embodiment, the compounds may be administered in combination, or sequentially, with another therapeutic agent. Such other therapeutic agents include those known for treatment, prevention, or amelioration of one or more symptoms of amyloidosis and synuclein diseases. Such therapeutic agents include, but are not limited to, donepezil hydrochloride (Aracept), rivastigmine tartrate (Exelon), tacrine hydrochloride (Cognex) and galantamine hydrobromide (Reminyl).

Methods of Use of the Compounds and Compositions

The compounds and compositions provided herein are useful in methods of treatment, prevention, or amelioration of one or more symptoms of β-amyloid diseases or disorders, including but not limited to diseases associated with the formation, deposition, accumulation, or persistence of β-amyloid fibrils. In certain embodiments, the compounds and compositions provided herein are used for treatment, prevention, or amelioration of one or more symptoms of diseases including, but not limited to of Alzheimer's disease. Down's syndrome, hereditary cerebral hemorrhage with amyloidosis of the Dutch type, and cerebral β-amyloid angiopathy.

Also provided are methods to inhibit or prevent α-synuclein fibril formation, methods to inhibit or prevent α-synuclein fibril growth, and methods to cause disassembly, disruption, and/or disaggregation of preformed α-synuclein fibrils and α-synuclein-associated protein deposits.

In certain embodiments, the synuclein diseases or synucleinopathies treated, prevented or whose symptoms are ameliorated by the compounds and compositions provided herein include, but are not limited to diseases associated with the formation, deposition, accumulation, or persistence of synuclein fibrils, including α-synuclein fibrnls. In certain embodiments, such diseases include Parkinson's disease, familial Parkinson's disease, Lewy body disease, the Lewy body variant of Alzheimer's disease, dementia with Lewy bodies, multiple system atrophy, and the Parkinsonism-dementia complex of Guam.

The following non-limiting Examples are given by way of illustration only and are not considered a limitation of this invention, many apparent variations of which are possible without departing from the spirit or scope thereof.

EXAMPLES

General Experimental Procedures

All solvents were distilled before use and were removed by rotary evaporation at temperatures up to 35° C. Merck silica gel 60, 200-400 mesh, 40-63 μm, was used for silica gel flash chromatography. TLC was carried out using Merck DC-plastikfolien Kieselgel 60 F254, first visualised with a UV lamp, and then by dipping in a vanillin solution (1% vanillin, 1% $H_2SO_4$ in EtOH), and heating. Mass spectra were recorded on a Kratos MS-80 instrument. NMR spectra, at 25° C., were recorded at 500 or 300 MHz for $^1H$ and 125 or 75 MHz for $^{13}C$ on Varian INOVA-500 or VXR-300 spectrometers. Chemical shifts are given in ppm on the δ scale referenced to the solvent peaks: $CHCl_3$ at 7.25 and $CDCl_3$ at 77.0 ppm or $(CH_3)_2CO$ at 2.15 and $(CD_3)_2CO$ at 30.5 ppm or $CH_3OD$ at 3.30 and $CD_3OD$ at 39.0 ppm.

HPLC Conditions

Samples were analysed using an Agilent HP1100 instrument, operated with EzChrom Elite software, and fitted with a C18 column (Phenomenex Prodigy 5 μm 100 A, 250×4.6 mm) with a guard column (Phenomenex ODS 4×3 mm, 5 μm) held at 30° C. Peaks were detected at 280 nm. The mobile phase was acetonitrile in water (with 0.1% TFA): $t_0$=11%, $t_{20}$=11%, $t_{30}$=100%, $t_{31}$=11%, $t_{40}$=11%. The flow rate was 1 mL/min and the injection volume of 5 μL.

Example 1

Synthesis of Sulfonamide 2

3,4 dihydroxybenzenesulfonic acid 3,4 dihydroxyphenylsulfonamide (Compound 5)

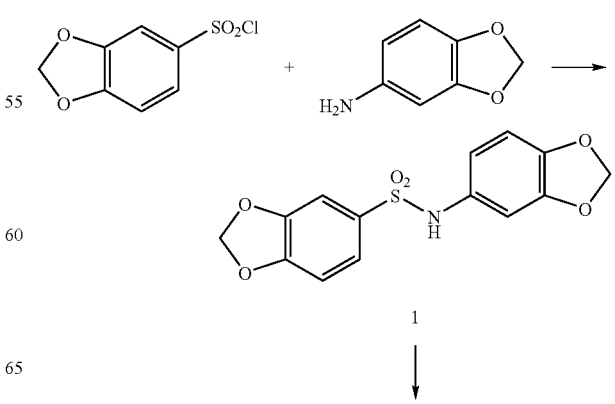

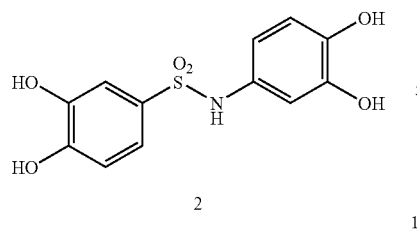

Synthesis of the sulfonamide 2 was accomplished by reaction of 3,4-methylenedioxybenzenesulfonyl chloride (prepared from 1,2-methylenedioxybenene (Tao, E. V. P.; Miller, W. D. U.S. Pat. No. 5,387,681. 1995)) with 3,4-methylenedioxyaniline to give the sulfonamide 1 in good yield. Deprotection with boron tribromide under standard conditions gave the free phenolic sulfonamide in reasonable yield.

To a stirred solution of 1,3-benzodioxole-5-sulfonyl chloride (Tao, E. V. P.; Miller, W. D. U.S. Pat. No. 5,387,681. 1995) (1 g) in dichloromethane (DCM) (10 ml) was added a solution of 3,4-methylenedioxyaniline (0.62 g) in dichloromethane (10 ml) followed by pyridine (1 ml). The mixture was refluxed for 2 hours, cooled, diluted with dichloromethane (150 ml), washed with aqueous HCl (1M, 2×100 ml), dried, then evaporated in vacuo to give the crude product as a brown gum. Purification by column chromatography over silica gel eluting with 5-10% ethyl acetate in dichloromethane gave the pure sulphonamide 1 as a pale brown gum (1.34 g, 92%). Crystallisation from 95% ethanol gave the product as pale brown crystals.

HPLC 29.6 minutes.

$^1$H NMR ((CD$_3$)$_2$CO) 8.75 (1H, s), 7.39 (2H, dd, J 2, 9 Hz), 7.24 (1H, d, J 2 Hz), 7.02 (1H, d, J 9 Hz), 6.86 (1H, d, J 2 Hz), 6.81 (1H, d, J 9 Hz), 6.72 (2H, dd, J 2, 9 Hz), 6.23 (2H, s) and 6.06 (2H, s).

HREIMS Found, 344.0201; MNa$^+$, C$_{14}$H$_{11}$NNaO$_6$S requires 344.0199.

To a solution of the sulphonamide 1 (0.7 g) in dry DCM (50 ml) was added boron tribromide (0.5 ml) and the mixture left at room temperature for 3 hours. Methanol (dropwise then 5 ml) was added carefully then the reaction left at room temperature for 24 hours. The mixture was evaporated in vacuo to 1 ml, then more methanol (20 ml) was added, this was repeated four times, then the solvents were removed by evaporation in vacuo.

Purification by column chromatography over silica gel eluting with 0-20% methanol in chloroform gave the product as a pale brown gum. Further purification over C-18 reverse phase silica eluting with 0-50% acetonitrile in water, followed by freeze drying, gave the pure product 2 as a light brown powder (295 mg, 45%).

HPLC 12.9 minutes 95%

$^1$H NMR (CD$_3$OD) 7.05 (1H, d, J 2 Hz), 7.03 (2H, dd, J 2, 9 Hz), 6.76 (1H, d, J 9 Hz), 6.57 (1H, d, J 2 Hz), 6.56 (1H, d, J 9 Hz) and 6.31 (2H, dd, J 2, 9 Hz).

HREIMS Found, 296.0241, M$^-$, C$_{12}$H$_{10}$NO$_6$S requires, 296.0234.

Example 2

Synthesis of Imidazole 4

2,4 bis(3,4 dihydroxyphenyl)imidazole (Compound 6)

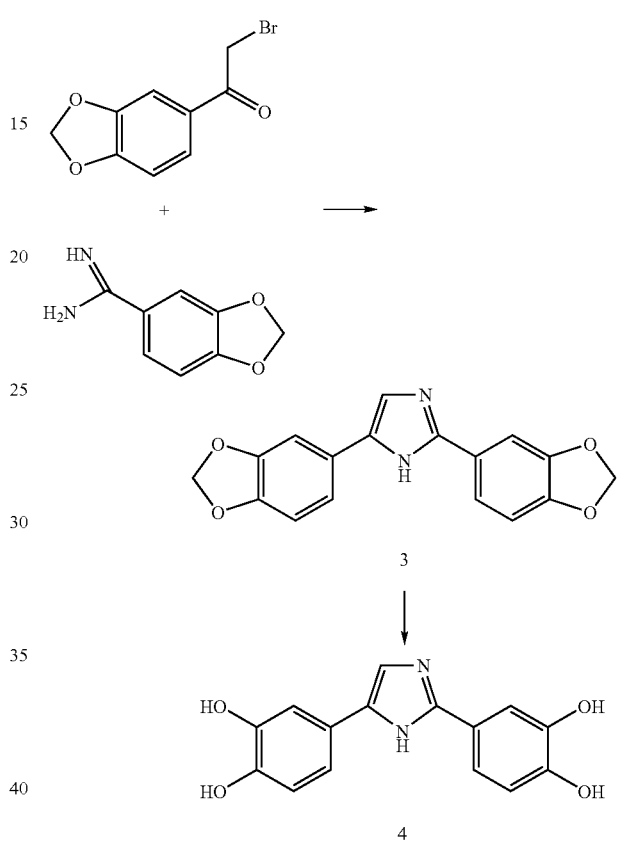

The imidazole ring was formed according to the method described by Li et al. (Li et al. Organic Process Research and Development 2002, 6, 682-3) from the amidinobenzene, formed from piperonylonitrile (Thurkauf et al. J Med. Chem. 1995, 38 (12), 2251-2255) and the bromoketone (Castedo et al. Tetrahedron 1982, 38 (11), 1569-70) formed from 3,4-methylenedioxyacetophenone according to the method described by Lee et al. (Korean Chem. Soc. 2003, 24 (4), 407-408). Deprotection with boron tribromide under standard conditions gave the free phenolic imidazole in good yield.

According to the process described by Li, a mixture of 3-amidinobenzene (Thurkauf et al. J Med. Chem. 1995, 38 (12), 2251-2255) (0.5 g, 3 mmol) and potassium bicarbonate (1.20 g, 12 mmol) in tetrahydrofuran (THF) (16 ml) and water (4 ml) was heated vigorously at reflux. Bromoketone (Castedo et al. Tetrahedron 1982, 38 (11), 1569-70; and Lee et al. Korean Chem. Soc. 2003, 24 (4), 407-408) (0.729 g, 3 mmol) in THF (4 ml) was added over 30 minutes and reflux was maintained for a further 2 hours. The THF was then removed by evaporation in vacuo and the residue extracted into ethyl acetate, dried and evaporated in vacuo to give the crude product as a brown solid. Crystallisation from 95% ethanol gave the pure imidazole 3 as a pale yellow crystalline solid (0.54 g, 58%).

HPLC 27.9 minutes. NMR ((CD$_3$)$_2$CO) 7.45-7.70 (5H, m), 7.02 (1H, d, J 9 Hz), 6.95 (1H, d, J 9 Hz), 6.15 (2H, s) and 6.09 (2H, s) HREIMS Found, 309.0875; MH$^+$, C$_{17}$H$_{12}$N$_2$O$_4$ requires, 309.0870.

To a solution of the imidazole 3 (0.5 g) in dry DCM (50 ml) was added boron tribromide (1.0 ml) and the mixture left at room temperature for 3 hours. Methanol (dropwise then 5 ml) was added carefully then the reaction left at room temperature for 24 hours. The mixture was evaporated in vacuo to 1 ml, then more methanol (30 ml) was added, this was repeated four times, then the solvents were removed by evaporation in vacuo.

Purification by column chromatography over silica gel eluting with 0-20% methanol in chloroform gave the product 4 as a pale brown solid (0.27 g, 58%).

HPLC 16.3 minutes 99%

$^1$H NMR (CD$_3$OD) 7.59 (1H, s), 7.36 (1H, d, J 2 Hz), 7.31 (2H, dd, J 2, 9 Hz), 7.16 (1H, d, J 2 Hz), 7.10 (2H, dd, J 2, 9 Hz), 6.98 (1H, d, J 9 Hz) and 6.88 (1H, d, J 9 Hz).

HREIMS Found, 285.0873; MH$^+$, C$_{15}$H$_{13}$N$_2$O$_4$ requires 285.0870.

Example 3

Synthesis of Triazole 7

3,5 bis(3,4 dihydroxyphenyl) 1,2,4 triazole (Compound 7)

According to the process described by Bentiss (Bentiss et al. J Heterocyclic Chem. 1999, 36, 149-152) a mixture of aromatic nitrile (1 g), hydrazine hydrate (1 g) and hydrazine hydrochloride (0.5 g) in solution in ethylene glycol (5 ml) was heated to 130° C. for 5 hours. The solution was cooled then diluted with water (7 ml), the solid product was filtered, washed with DCM then dried to give the crude product. Recrystalisation from methanol gave the pure 4-aminotriazole 5, as a pale yellow solid (0.65 g, 66%).

HPLC 27.0 minutes.

$^1$H NMR ((CD$_3$)$_2$CO) 7.62 (2H, dd, J 2, 9 Hz), 7.42 (2H, d, J 2 Hz), 6.94 (2H, d, J 9 Hz), 6.15 (2H, s) and 5.93 (4H, s).

HREIMS Found, 325.0937; MH$^+$, C$_{16}$H$_{13}$N$_4$O$_4$ requires 325.0931.

According to the process described by Bentiss (Bentiss et al. J. Heterocyclic Chem. 2002, 39, 93-96) to a stirred solution of amino triazole 5 (0.5 g) in an aqueous solution of hypophosphorus acid (50%, 5 ml) a solution of sodium nitrite (0.6 g) in water (1.5 ml) was added slowly. The mixture was stirred at room temperature for a further hour then the pale orange precipitate was collected, washed with water and dried to give the triazole 6 (0.38, 80%).

HPLC 29.48 minutes.

$^1$H NMR ((CD$_3$)$_2$CO) 7.81 (2H, dd, J 2, 9 Hz), 7.70 (2H, d, J 2 Hz), 7.10 (2H, d, J 9 Hz) and 6.20 (4H, s). HREIMS Found, 310.0818; C$_{16}$H$_{12}$N$_3$O$_4$ requires 310.0822.

To a solution of the triazole 6 (0.5 g) in dry DCM (50 ml) was added boron tribromide (1.0 ml) and the mixture left at room temperature for 3 hours. Methanol (dropwise then 5 ml) was added carefully then the reaction left at room temperature for 24 h. The mixture was evaporated in vacuo to 1 ml, then more methanol (30 ml) was added, this was repeated four

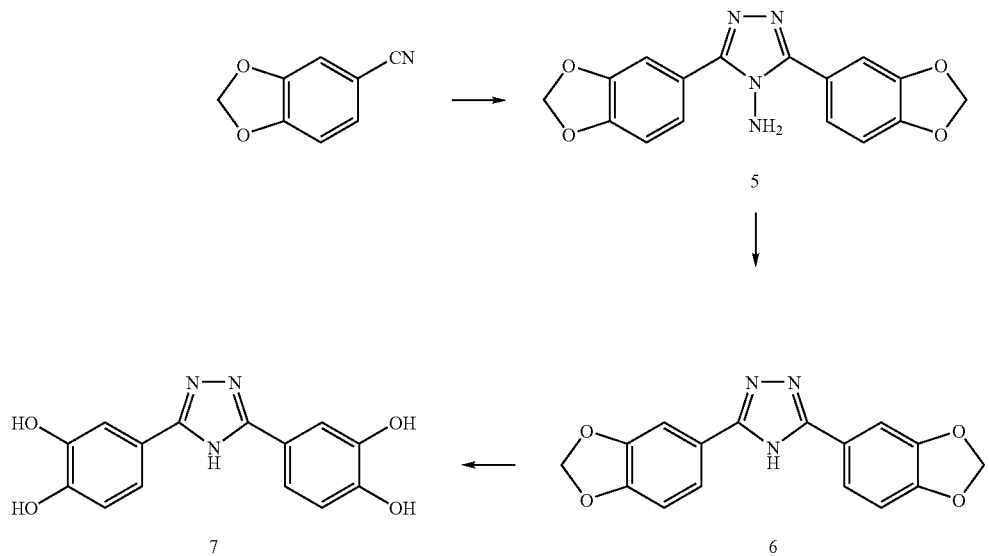

The 4-aminotriazole ring was formed by a dimerization reaction of piperonylonitrile according to the method described by Bentiss (Bentiss et al. J Heterocyclic Chem. 1999, 36, 149-152) and then deamination was carried out according to the method described by Bentiss (Bentiss et al. J. Heterocyclic Chem. 2002, 39, 93-96.) to give the triazole 6 in good yield. Deprotection with boron tribromide under standard conditions gave the free phenolic triazole 7 in good yield.

times, then the solvents were removed by evaporation in vacuo.

Purification by column chromatography over silica gel eluting with 0-20% methanol in chloroform gave the product 7 as a pale brown solid (0.24 g, 52%).

HPLC 16.1 minutes 97%

$^1$H NMR (CD$_3$OD) 7.46 (2H, d, J 2 Hz), 7.41 (2H, dd, J 2, 9 Hz), 7.15 (1H, s) and 6.96 (2H, d, J 9 Hz).

HREIMS Found, 286.0815; MH$^+$, C$_{14}$H$_{12}$N$_3$O$_4$ requires 286.0822.

Example 4

Synthesis of Pyrazole 9

3,5 bis(3,4 dihydroxyphenyl)pyrazole (Compound 8)

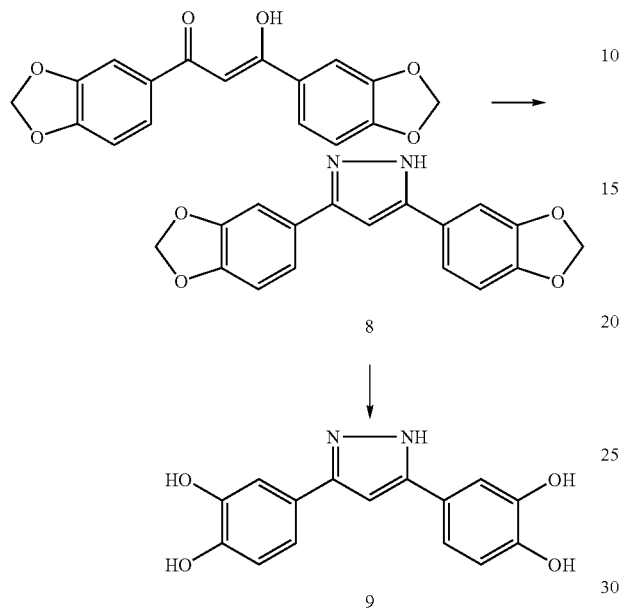

Reaction of the 1,3-diketone (Lopez et al. Planta Med. 1998, 64 (1), 76-77) (prepared according to the method described by Choshi et al. (Chem. Pharm. Bull. 1992, 40 (4), 1047-1049) with hydrazine hydrate according to the method described by Fink et al. (Chemistry and Biology 1999, 6, 205-219) gave the pyrazole 8 in good yield. Deprotection with boron tribromide under standard conditions gave the free phenolic pyrazole 9 in good yield.

According to the method described by Fink et al. (Chemistry and Biology 1999, 6, 205-219) a suspension of the diketone (Choshi et al. Chem. Pharm. Bull. 1992, 40 (4), 1047-1049 and Lopez et al. Planta Med. 1998, 64 (1), 76-77) (1 g) and hydrazine HCl (1 g, 5 equivs) in DMF/THF (3:1, 12 ml) was heated to reflux for 24 h. Water was added and the mixture extracted into dichloromethane, dried and evaporated in vacuo to give the crude product 8 as a yellow solid. Purification by column chromatography over silica gel eluting with 0-20% ethyl acetate in dichloromethane gave the pyrazole 8 as a pale yellow solid (0.49 g, 50%).

HPLC 30.3 minutes $^1$H NMR ((CD$_3$)$_2$CO) 7.47 (2H, dd, J 2, 9 Hz), 7.46 (2H, d, J 2 Hz), 7.04 (1H, s), 7.02 (2H, d, J 9 Hz) and 6.14 (4H, s).

HREIMS Found, 309.0859; MH$^+$, C$_{17}$H13N2O4 requires 309.0870.

To a solution of the pyrazole 8 (0.46 g) in dry DCM (50 ml) was added boron tribromide (0.4 ml) and the mixture left at room temperature for 3 hours. Methanol (dropwise then 5 ml) was added carefully then the reaction left at room temperature for 24 hours. The mixture was evaporated in vacuo to 1 ml, then more methanol (30 ml) was added, this was repeated four times, then the solvents were removed by evaporation in vacuo.

Purification by column chromatography over silica gel eluting with 0-20% methanol in chloroform gave the pyrazole 9 as a pale yellow solid. (0.285 g, 67%).

HPLC 25.9 minutes 98%

$^1$H NMR (CD$_3$OD) 7.26 (2H, d, J 2 Hz), 7.22 (2H, dd, J 2, 9 Hz), 7.15 (1H, s) and 6.93 (2H, d, J 9 Hz).

HREIMS Found, 285.0879; C$_{15}$H$_{13}$N$_2$O$_4$ requires, 285.0870.

Example 5

Synthesis of Adamantane 10

1,3 bis(3,4 dihydroxyphenyl)adamantane (Compound 9)

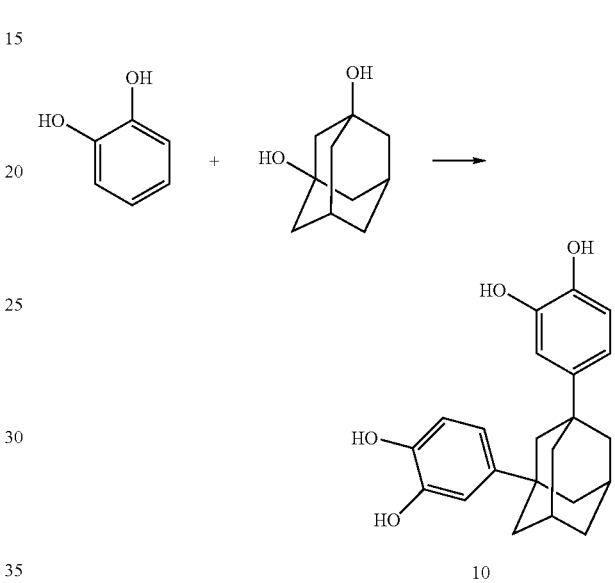

Reaction of catechol with 1,3-adamantane-diol according to the method described by Lu et al (Lu et al. J Med Chem 2005, 48 (14), 4576-4585) gave the adduct 10 in reasonable yield.

According to the method described by Lu a solution of catechol (1.0 g) and adamantane diol (0.5 g) in methanesulfonic acid (2 ml) was heated to 80° C. for 3 hours, then left at room temperature overnight. Water was added and the mixture extracted into 10% methanol in chloroform which was dried and evaporated in vacuo to give a white solid. Purification by column chromatography over silica gel eluting with 0-20% methanol in chloroform gave the product as a white solid. Crystallisation from diethyl ether/40% petroleum ether then gave the pure product 10 as a white crystalline solid (210 mg, 20%).

HPLC 29.8 minutes 98%

$^1$H NMR (CD$_3$OD) 6.82 (2H, t, J 1.5 Hz), 6.68 (4H, d, J 1.5 Hz), 2.22 (2H, bs), 1.87 (8H, m) and 1.77 (2H, bs).

HREIMS Found, 387.1369; MCl$^-$, C$_{22}$H$_{24}$ClO$_4$ requires, 387.1369.

Example 6

Compounds of this Invention are Potent Disrupters of Alzheimer's Aβ 1-42 Fibrils The compounds prepared in the preceding Examples were found to be potent disruptors/inhibitors of Alzheimer's disease β-amyloid protein (Aβ) fibrnls. In a set of studies, the efficacy of the compounds to cause a disassembly/disruption of pre-formed amyloid fibrils of Alzheimer's disease (i.e. consisting of Aβ 1-42 fibrils) was analyzed.

Part A—Thioflavin T fluorometry

In one study, Thioflavin T fluorometry was used to determine the effects of the compounds, and of EDTA (as a negative control). In this assay Thioflavin T binds specifically to fibrillar amyloid, and this binding produces a fluorescence enhancement at 485 nm that is directly proportional to the amount of amyloid fibrils formed. The higher the fluorescence, the greater the amount of amyloid fibrils formed (Naki et al., Lab. Invest. 65:104-110, 1991; Levine III, Protein Sci. 2:404-410, 1993; Amyloid: Int. J. Exp. Clin. Invest. 2:1-6, 1995).

In this study, 30 µL of a 1 mg/mL solution (in distilled water) of pre-fibrillized Aβ 1-42 (rPeptide) was incubated at 37° C. for 3 days either alone, or in the presence of one of the compounds or EDTA (at Aβ:test compound weight ratios of 1:1, 1:0.1, 1:0.01 or 1:0.001). Following 3-days of co-incubation, 50 µl of each incubation mixture was transferred into a 96-well microtiter plate containing 150 µl of distilled water and 50 µl of a Thioflavin T solution (i.e. 500 mM Thioflavin T in 250 mM phosphate buffer, pH 6.8). The emission fluorescence was read at 485 nm (444 nm excitation wavelength) using an ELISA plate fluorometer after subtraction with buffer alone or compound alone, as blank.

Figure 5:
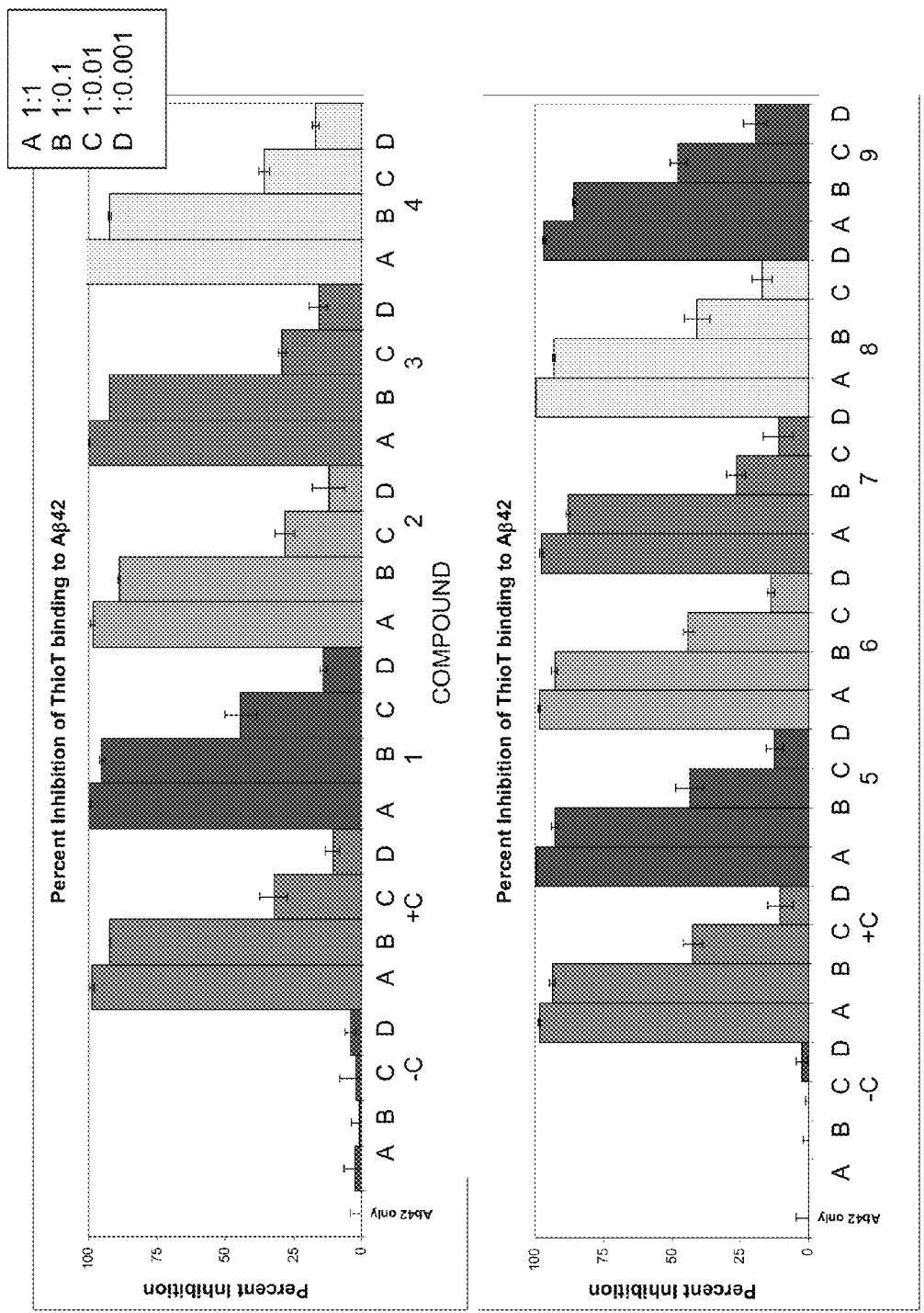
FIG. 5 graphically summarizes the results, as measured by Thio T, of the tested compounds to inhibit Aβ fibril formation.

The results of the 3-day incubations are illustrated graphically in FIG. 5. For example, whereas EDTA ('–C' in FIG. 5) caused no significant inhibition of Aβ 1-42 fibrils at all concentrations tested, the compounds all caused a dose-dependent disruption/disassembly of preformed Aβ 1-42 fibrils. All of the compounds tested were effective in disrupting pre-formed Aβ 1-42 fibrils similar to the results obtained from a positive control compound ('+C' in FIG. 5). For example, all of the compounds caused at least 96% inhibition when used at an Aβ:test compound wt/wt ratio of 1:1 compared to 99% for the control. At an Aβ:test compound wt/wt ratio of 1:0.1 the levels of inhibition ranged from 86 to 95% compared to 92% for the control. This study indicated that the compounds of this invention are potent disruptors/inhibitors of Alzheimer's disease type Aβ fibrils, and usually exert their effects in a dose-dependent manner.

Part B: Congo Red

In the Congo red binding assay the ability of a test compound to alter β-amyloid binding to Congo red is quantified. In this assay, Aβ 1-42 (as prepared for the Thio T assay) and test compounds were incubated for 3 days and then vacuum filtered through a 0.2 µm filter. The amount of Aβ 1-42 retained in the filter was then quantitated following staining of the filter with Congo red. After appropriate washing of the filter, any lowering of the Congo red color on the filter in the presence of the test compound (compared to the Congo red staining of the amyloid protein in the absence of the test compound) was indicative of the test compound's ability to diminish/alter the amount of aggregated and congophilic Aβ.

Figure 6:
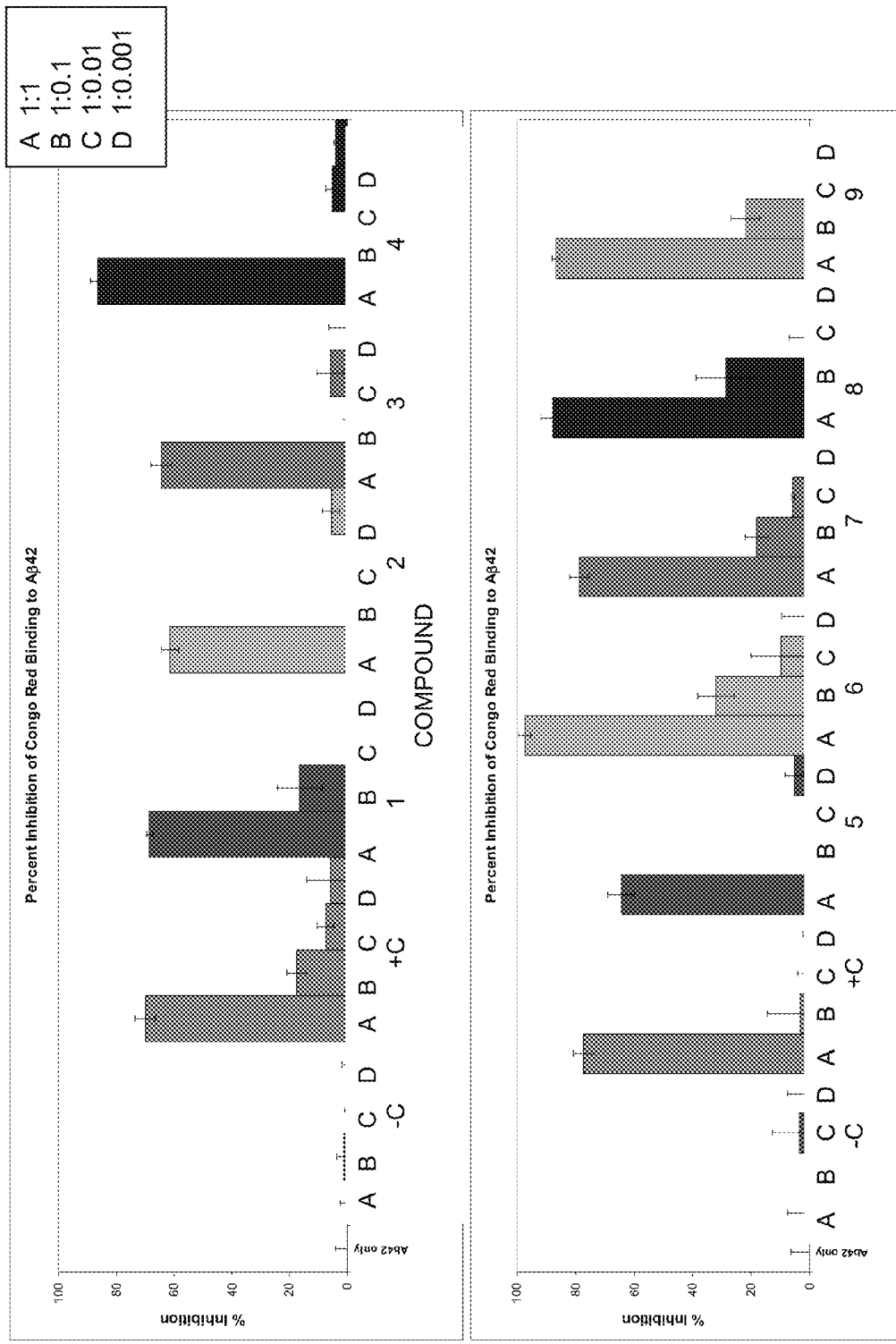
FIG. 6 graphically summarizes the results, as measured by Congo Red, of the tested compounds to inhibit Aβ fibril formation.

In one study, the ability of Aβ fibrils to bind Congo red in the absence or presence of increasing amounts of the compounds or EDTA (at Aβ:test compound weight ratios of 1:1, 1:0.1, 1:0.01 or 1:0.001) was determined. The results of 3-day incubations are illustrated graphically in FIG. 6. Whereas EDTA ('–C' in FIG. 6) caused no significant inhibition of Aβ 1-42 fibril binding to Congo red at all concentrations tested, the compounds caused a dose-dependent inhibition of Aβ binding to Congo red, some exceeding the effects of the positive control compound ('+C' in FIG. 6). For example, the positive control compound caused a significant (p<0.01) 73.5% inhibition of Congo red binding to Aβ 1-42 fibrils when used at an Aβ:test compound wt/wt ratio of 1:1, and a significant (p<0.01) 10.4% inhibition of Congo red binding when used at an Aβ:test compound wt/wt ratio of 1:0.1. Compounds 6, 8 and 9 exceed the results of the positive control compound at both the above noted ratios. Similar to the results for Thio T assay, this study also indicated that compounds of this invention are potent inhibitors of Aβ fibril binding to Congo red, and usually exert their effects in a dose-dependent manner.

Part D—Circular Dichroism Spectroscopy Data

Circular dichroism (CD) spectroscopy is a method that can be used to determine the effects of test compounds on disruption of the secondary structural conformation of amyloid fibrils. In one study, as described in this example, circular dichroism spectroscopy was used to determine the effects of different compounds of the invention on the β-sheet conformation of Aβ$_{1-42}$ fibrils. For this study, Aβ$_{1-42}$ (rPeptide Inc., Bogart, Ga.) was first lyophilized from a 50 mM NaOH solution, the pH being maintained above 10 prior to freezing and lyophilization. The peptide was then reconstituted in 20 mM acetate buffer, pH 4.0, at a concentration of 1 mg/ml. Dilution and addition of test compounds or vehicle was performed such that the final concentration of peptide was 0.5 mg/ml and the Aβ$_{1-42}$:test compound wt/wt ratios were 1:1 and 1:0.1. When no test compounds were added, the amount of vehicle added to the reaction mixture was equal to the amount used to deliver the test compounds. After 5 days of incubation at 37° C. in the presence of compounds or vehicle, CD spectra were recorded on a Jasco 810 spectropolarimeter (Easton, Md.). All CD spectra were collected in 0.05 or 0.1 cm quartz cells. Wavelength traces were scanned from 190-270 nm at 0.1 nm increments with a bandwidth of 2 nm, at a scan speed of 50 nm per minute, a response time of 1 second, and a data pitch of 0.1 nm. The whole system was equilibrated and continuously flushed with nitrogen at 10 L/min. For data processing, 10 replicate spectra of Aβ$_{1-42}$ with vehicle added were acquired before incubation, averaged, and subtracted from 10 averaged spectra of "Aβ$_{1-42}$+test compound" or vehicle after the incubation period. Average spectra were converted from ellipticity in degrees to specific ellipticity using the formula [Ψ]=(Ψ°/d)xc where Ψ° is the ellipticity in degrees, d is the pathlength in mm and c is the concentration in mg/ml. In this manner, the change in the structure of the peptide that occurs between that found at the time of initial dissolution and that found after incubation can be assessed.

FIG. 1A shows some of the CD spectra generated in this study. Aβ$_{1-42}$ alone (vehicle in FIG. 1A) in 20 mM acetate buffer after incubation usually demonstrated the typical CD spectrum of an amyloid protein with significant β-sheet structure, as demonstrated by the minimum observed at 218 nm. However, in the presence of some of the compounds, a marked disruption of the β-sheet structure in Aβ$_{1-42}$ fibrils was evident (with a significant increase in random coil or α-helix) as shown by the reduction in the magnitude of the minimum observed at 218 nm (compare to Aβ$_{1-42}$ alone).

FIG. 1B shows the effects of compounds 1 and 2 on inhibition of the β-sheet structure of Aβ$_{1-42}$ fibril formation when compared to a positive control compound. The CD studies demonstrate that the compounds of this invention have the ability to disrupt/disassemble the β-sheet structure characteristic of Alzheimer's Aβ fibrils. The results of the studies also confirm the previous examples using Thioflavin T fluorometry and Congo red binding type assays.

Example 7

Compounds of this Invention are Potent Disrupters of Parkinson's Disease α-Synuclein Fibrils The tested compounds of this invention were found also to be potent disruptors/inhibitors of Parkinson's disease α-synuclein fibrils. α-synuclein has been demonstrated to form fibrils when incubated at 37° C. for several days. α-synuclein is postulated to play an important role in the pathogenesis of Parkinson's disease and other synucleinopathies. In this set of studies, the efficacy of the compounds to cause a disassembly/ disruption of pre-formed α-synuclein fibrils of Parkinson's disease was analyzed.

Part A—Thioflavin T Fluorometry

In one study, Thioflavin T fluorometry was used to determine the effects of the compounds and EDTA (as a negative control, (−C)). In this assay, Thioflavin T binds specifically to α-synuclein fibrils, and this binding produces a fluorescence enhancement at 485 nm that is directly proportional to the amount of α-synuclein fibrils present. The higher the fluorescence, the greater the amount of α-synuclein fibrils present (Naki et al, *Lab. Invest.* 65:104-110, 1991; Levine III, *Protein Sci.* 2:404-410, 1993; *Amyloid: Int. J. Exp. Clin. Invest.* 2:1-6, 1995).

In this study, 30 μL of a 1 mg/mL solution of α-synuclein (rPeptide) was pre-fibrillized at 37° C. with agitation at 1400 rpm for 4 days and subsequently incubated at 37° C. for 3 days either alone or in the presence of the compounds or EDTA (at α-synuclein:compound weight ratios of 1:1, 1:0.1, 1:0.01 or 1:0.001). Following 3-days of co-incubation, 50 μl of each incubation mixture was transferred into a 96-well microtiter plate containing 150 μl of distilled water and 50 μl of a Thioflavin T solution (i.e. 500 mM Thioflavin T in 250 mM phosphate buffer, pH 6.8). The emission fluorescence was read at 485 nm (444 nm excitation wavelength) using an ELISA plate fluorometer after subtraction with buffer alone or compound alone, as blank.

Figure 7:
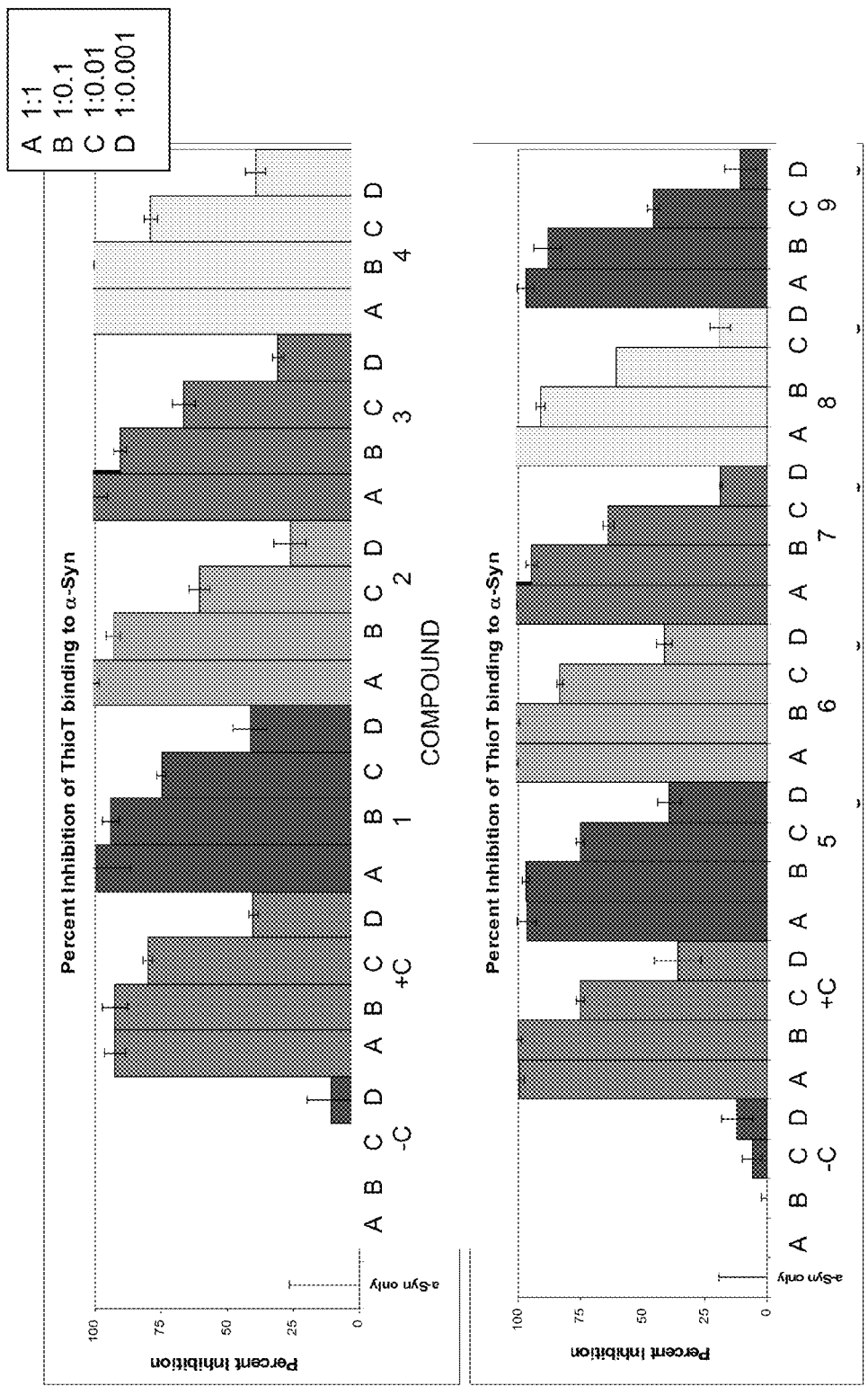
FIG. 7 graphically summarizes the results, as measured by Thio T, of the tested compounds to inhibit α-synuclein fibril formation.

The results of the 3-day incubations are graphically illustrated in FIG. 7. For example, whereas EDTA caused no significant inhibition of α-synuclein fibrils at all concentrations tested, all of the compounds caused a dose-dependent disruption/disassembly of pre-formed α-synuclein fibrils to various extents. For example, at an α-synuclein:compound ratio of 1:0.01 the positive control compound (+C in FIG. 7) caused a significant (p<0.01) 77.4% inhibition whereas the other compounds tested displayed a range from 45 to 83%. Compounds 1, 4, 5 and 6 displayed results very similar to the positive control compound. This study indicated that compounds of this invention are potent disruptors/inhibitors of Parkinson's disease α-synuclein fibrils, and usually exert their effects in a dose-dependent manner.

Part B: Congo Red

In the Congo red binding assay, the ability of a given test compound to alter α-synuclein binding to Congo red is quantified. In this assay, α-synuclein (pre-fibrillized as prepared in the Thio T assay) and compounds were incubated for 3 days and then vacuum filtered through a 0.2 μm filter. The amount of α-synuclein retained in the filter was then quantitated following staining of the filter with Congo red. After appropriate washing of the filter, any lowering of the Congo red color on the filter in the presence of the compound (compared to the Congo red staining of the amyloid protein in the absence of the compound) was indicative of the test compound's ability to diminish/alter the amount of aggregated and congophilic α-synuclein.

Figure 8:
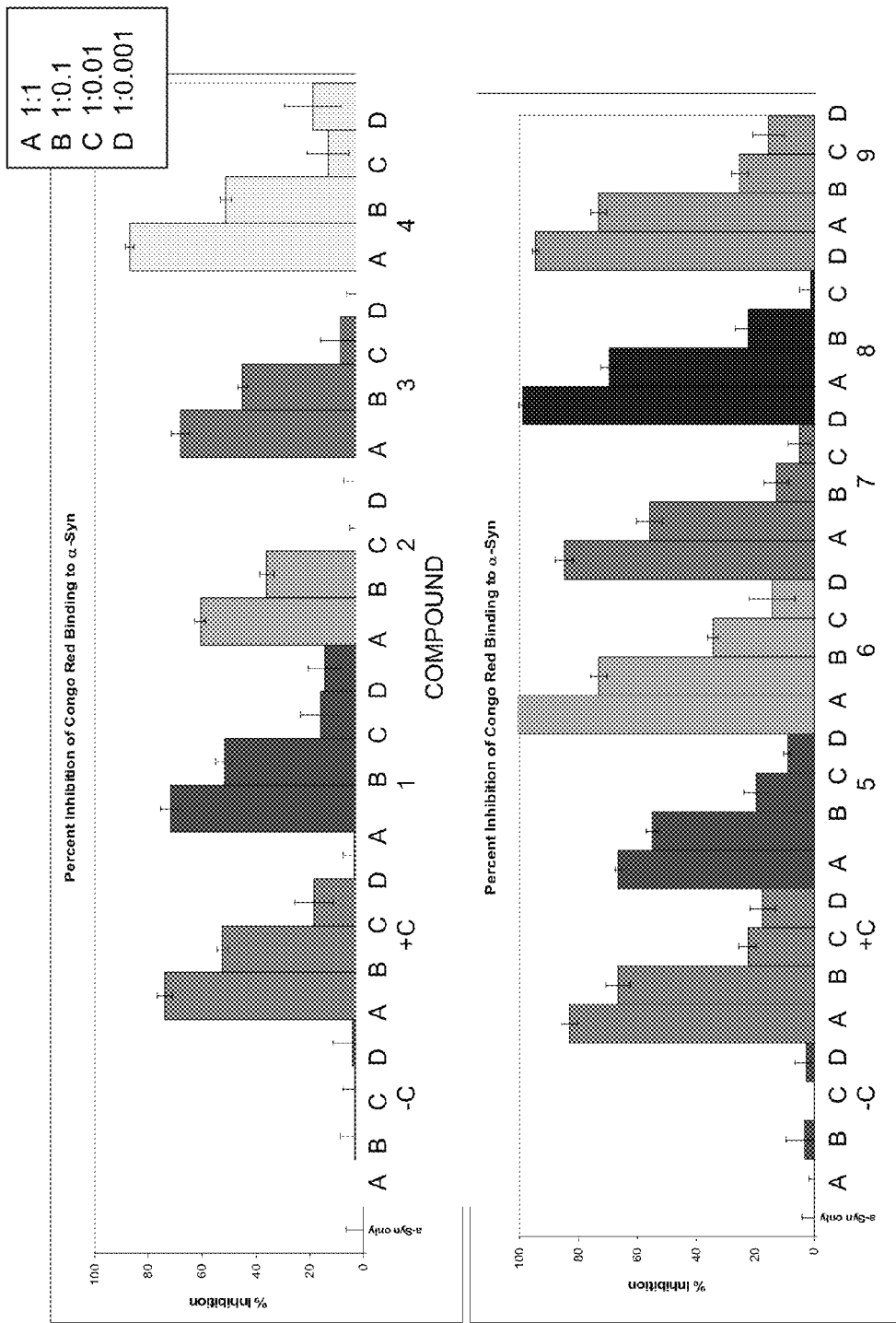
FIG. 8 graphically summarizes the results, as measured by Congo Red, of the tested compounds to inhibit α-synuclein fibril formation.
Figure 9:
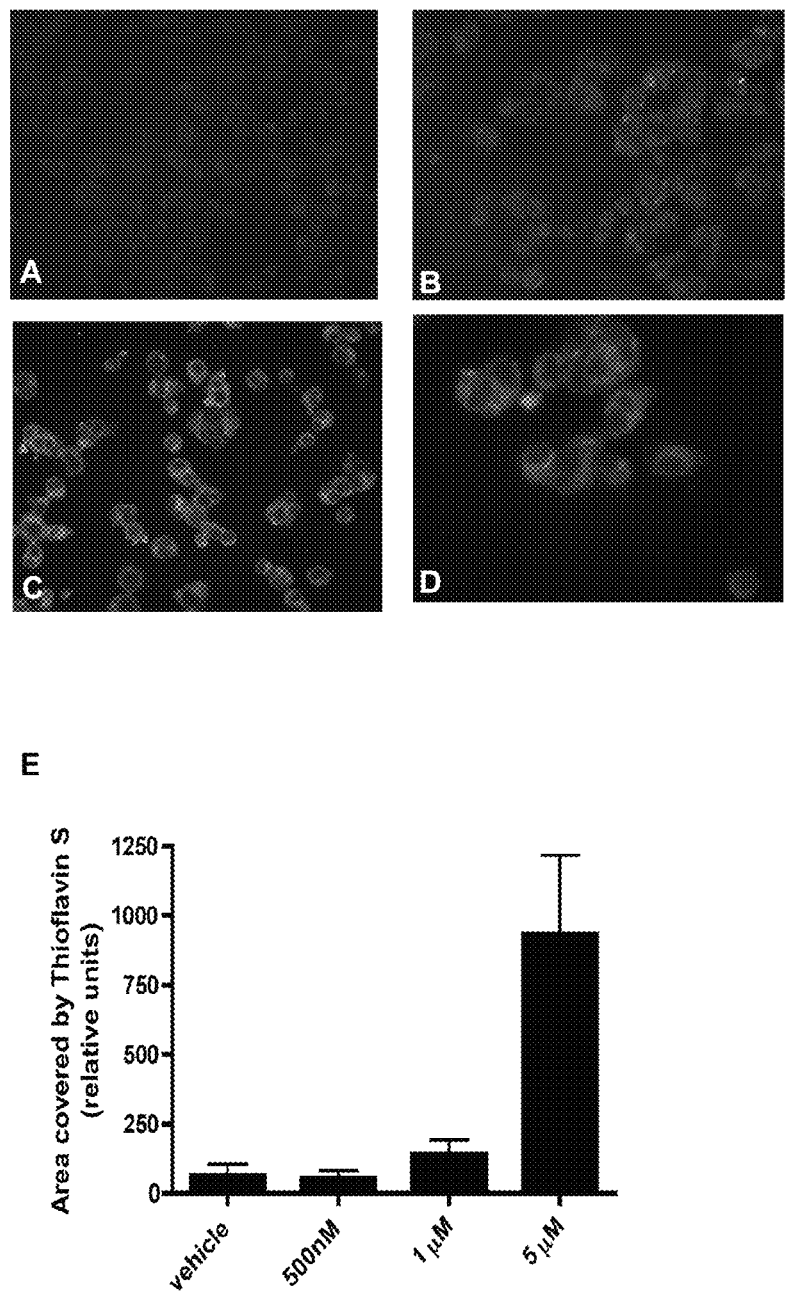
FIGS. 9 A-E are examples of fluorescent photomicrographs demonstrating effects of rotenone on number of thioflavin S-positive aggregates.

In one study, the ability of α-synuclein fibrils to bind Congo red in the absence or presence of increasing amounts of compounds or EDTA (at α-synuclein:compound weight ratios of 1:1, 1:0.1, 1:0.01 or 1:0.001) was determined. The results of 3-day incubations are graphically illustrated in FIG. 8. Whereas EDTA (−C) caused no significant inhibition of α-synuclein fibril binding to Congo red at all concentrations tested, the compounds tested caused a dose-dependent inhibition of α-synuclein binding to Congo red. For example, the positive control compound (+C) caused a significant (p<0.01) 78.5% inhibition of Congo red binding to α-synuclein fibrils at a wt/wt ratio of 1:1. The range of inhibition at the same ratio for the all of the compounds tested was from 60 to 100%. This study indicated that compounds of this invention are also potent inhibitors of Parkinson's disease type α-synuclein fibril binding to Congo red, and usually exert their effects in a dose-dependent manner.

Part C—Circular Dichroism

Circular dichroism (CD) spectroscopy is a method that can be used to determine effects of test compounds on disruption of the secondary structural conformation of α-synuclein fibrils. In one study, as described in this example, circular dichroism spectroscopy was used to determine the effects of different compounds of the invention on the β-sheet conformation of α-synuclein fibrils. For this study, α-synuclein (rPeptide Inc., Bogart, Ga.) was dissolved in 9.5 mM phosphate buffer (PBS) to 1 mg/ml. The resulting stock was diluted in the same buffer and either test compounds or vehicle added such that the final concentration of peptide was 0.25 mg/ml and the α-synuclein:compound wt/wt ratios were 1:1 and 1:0.1. A CD spectrum was recorded of the vehicle treated sample prior to incubation of all samples for 4 days, after which spectra for all α-synuclein/compound or vehicle reactions were acquired. CD spectra were recorded on a Jasco 810 spectropolarimeter (Easton, Md.). All CD spectra were acquired using 0.10 cm quartz cells. Wavelength traces were scanned from 190-270 nm at 0.1 nm increments with a bandwidth of 2 nm, at a scan speed of 50 nm/minute, a response time of 32 seconds, and a data pitch of 0.5 nm. The whole system was equilibrated and continuously flushed with nitrogen at 10 L/min. For data processing, 10 replicate spectra of the buffer with vehicle added were acquired before incubation, averaged, and subtracted from 10 averaged spectra of "α-synuclein+test compound" or vehicle after the incubation period. Average spectra were converted from ellipticity in degrees to specific ellipticity using the formula $[\Psi]=(\Psi°/d)xc$ where $\Psi°$ is the ellipticity in degrees, d is the pathlength in mm and c is the concentration in mg/ml. In this manner, the change in the structure of the peptide that occurs between that found at the time of initial dissolution and that found after incubation can be assessed.

Figure 2:
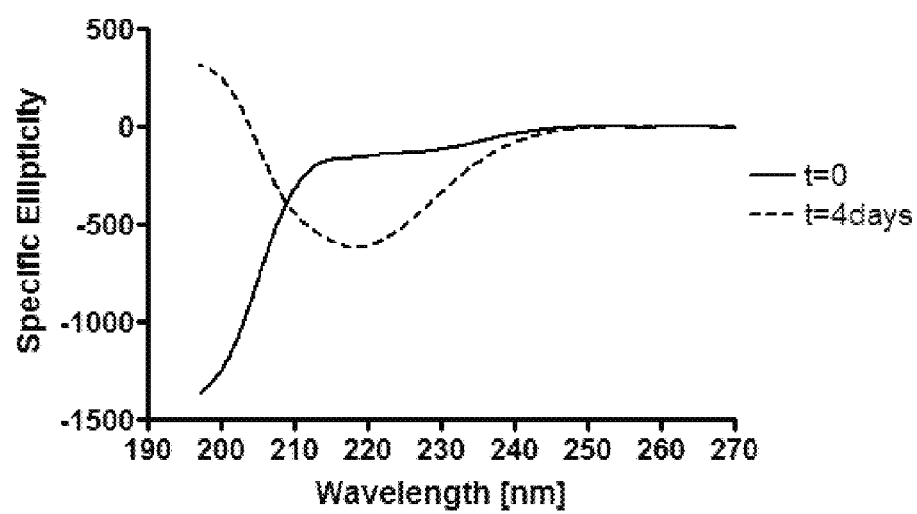
FIG. 2 shows comparative circular dichroism spectra illustrating α-synuclein forms β-sheet rich structure after 4 days of agitation at 37° C.

FIG. 2 shows the CD spectra generated for α-synuclein at time zero and after 4 days of incubation at 37° C. α-synuclein alone in vehicle treated PBS buffer demonstrated the random coil signature at time zero and after 4 days of incubation demonstrated the typical CD spectrum of a protein with significant β-sheet structure, as demonstrated by the minimum observed at 218 nm. However, in the presence of some of the compounds, a marked disruption of the β-sheet structure in α-synuclein fibrils was evident (with a significant increase in random coil or α-helix) as shown by the reduction in the magnitude of the minimum observed at 218 nm (compare to α-synuclein alone).

Figure 3:
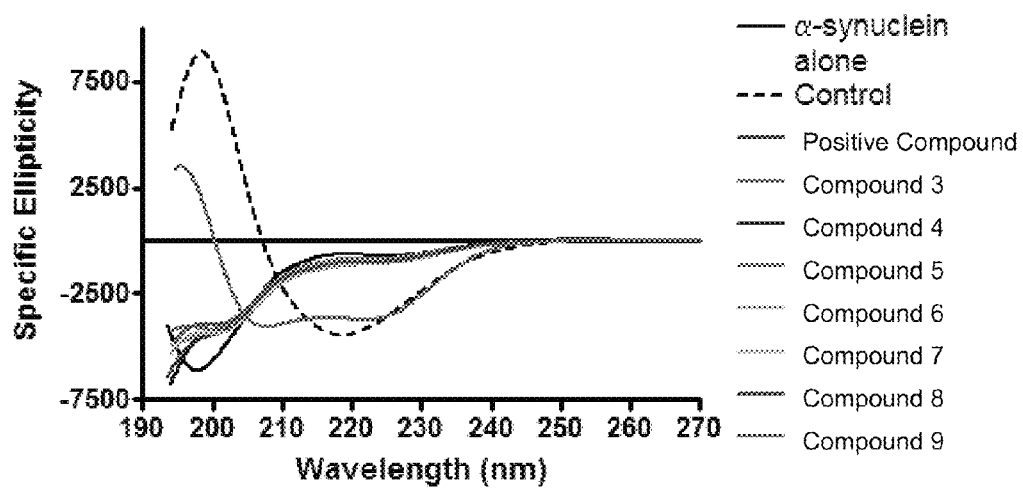
FIG. 3A shows several circular dichroism spectra illustrating that tested compounds inhibit α-synuclein aggregation at 1:1 wt/wt.
FIG. 3B shows graphically the % inhibition.
Figure 3:
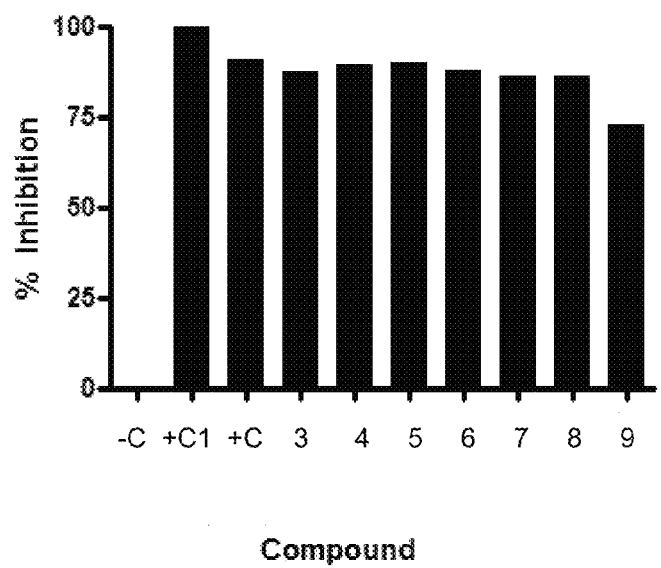

FIG. 3A shows some of the CD spectra generated in this study. α-synuclein at time zero produces the spectrum indicative of a random coil peptide and also provides the 100% inhibition control data. After incubation, the spectrum of α-synuclein is what would be expected for a β-sheet structure, indicating higher order aggregates have formed and is used to provide the 0% inhibition control data. Samples used for the controls are vehicle treated to assure a quantitative relationship between these samples and the test compound treated samples. These two spectra allow for the precise quantitation of the percent inhibition of fibril formation in the test compound treated samples due to their establishing of the positive and negative controls, which are assumed to be 100% and 0% fibrillar respectively. Despite these control percentages being only estimates, there is insufficient uncertainty to make them suspect, ie the lower end may be 0-5% inhibition while the upper end may be 95-100% inhibition. The controls are generated in each batch run, using the same stock solution of α-synuclein which is fractioned into aliquots of equal volume to which the individual test compound or vehicle are added and run in parallel to assure the accuracy of the quantitation. The spectra shown in FIG. 3A were acquired with an α-synuclein/test compound ratio of 1:1 wt/wt. These CD spectra demonstrate that the compounds of this invention have the ability to disrupt/disassemble the β-sheet structure characteristic of Parkinson's disease α-synuclein fibrils.

FIG. 3B shows the effects of compounds on inhibition of the β-sheet structure of α-synuclein when compared to a positive control compound (+C). The positive control (+C1) is, as stated, the time zero vehicle treated spectrum while the negative control (−C) is the 4 day vehicle treated spectrum.

Figure 4:
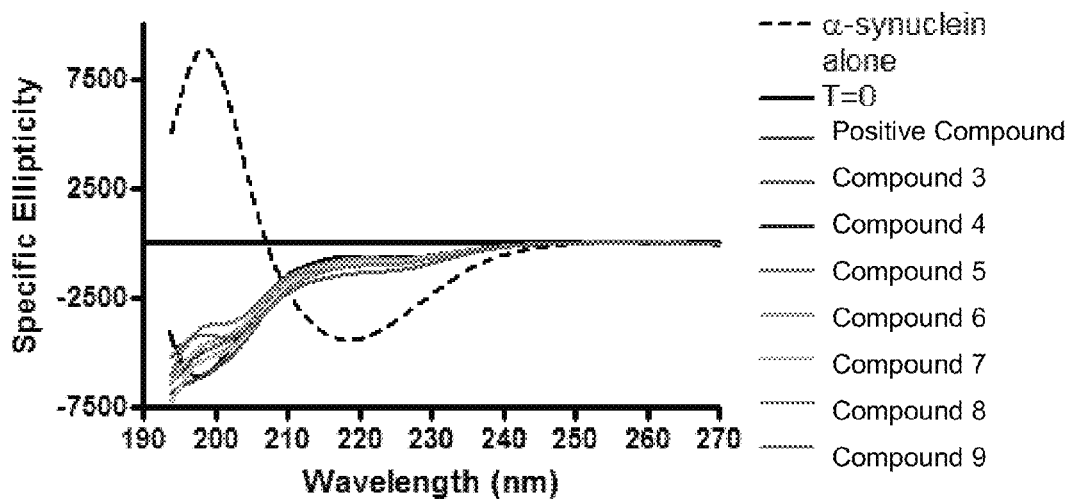
FIG. 4A shows several circular dichroism spectra illustrating that compounds inhibit α-synuclein aggregation at 1:0.1 wt/wt.
FIG. 4B shows graphically the % inhibition.
Figure 4:
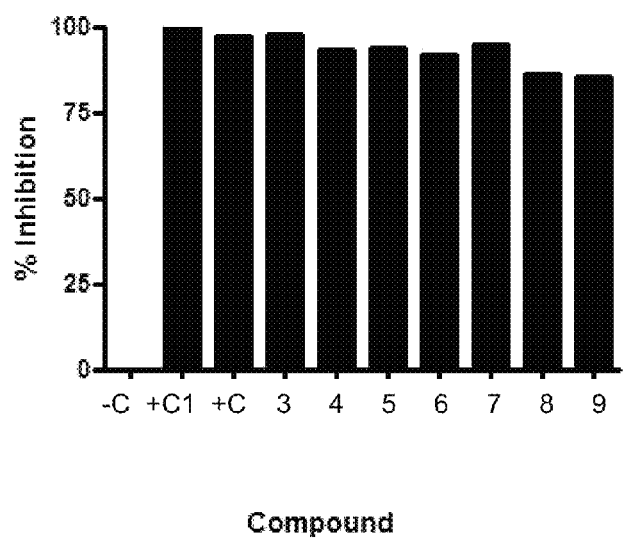

FIG. 4A shows some of the CD spectra that were acquired in this study. These spectra were acquired and processed in the same manner as those presented in FIG. 3A. These spectra also show marked disruption of the β-sheet signature found in the spectrum of the vehicle treated sample.

FIG. 4B shows the effects of compounds on inhibition of the β-sheet structure of α-synuclein when compared to a positive control compound (+C). The positive control (+C1) is, as stated, the time zero vehicle treated spectrum while the negative control (−C) is the 4 day vehicle treated spectrum.

The results of the studies also confirm the previous examples using Thioflavin T fluorometry and Congo red binding type assays, that the compounds of this invention are potent anti-α-synuclein fibrilization agents.

Example 8

Compounds of this Invention are Potent Disruptors/Inhibitors of α-Synuclein Fibrils Associated with Parkinson's Disease Parkinson's Disease is characterized by the accumulation of insoluble intraneuronal aggregates called Lewy Bodies, a major component of which is α-synuclein (reviewed in Dauer et al., *Neuron,* 39:889-909, 2003). Since autosomal dominant mutations in α-synuclein cause a subset of cases of familial Parkinson's disease, and since these mutations increase the likelihood of α-synuclein to aggregate and form Lewy Bodies, aggregated α-synuclein is proposed to be directly involved in the etiology and disease progression (Polymeropoulos et al., *Science* 276:1197-1199, 1997; Papadimitriou et al., *Neurology* 52:651-654, 1999). Structural studies have revealed that intracellular Lewy bodies contain a large proportion of misfolded proteins with a high degree of β-pleated sheet secondary structure. These studies were conducted to determine the efficacy of the test compounds in the inhibition/disruption of α-synuclein fibrils associated with Parkinson's disease.

Therefore, to test the therapeutic potential of the compounds, two cell-based assays were utilized. In both assays, rotenone is used to induce mitochondrial oxidative stress and α-synuclein aggregation. The first assay utilizes the binding of the fluorescent dye thioflavin S to structures with high β-sheet content including α-synuclein fibrils. Therefore, quantitative assessment of the extent of thioflavin S-positive staining of fixed cells is used to test the ability of the compounds to decrease the amount of α-synuclein aggregates. In the second assay, cell viability is assessed using the XTT Cytotoxicity assay, which is dependent on intact, functional mitochondria in live cells. Thus, the XTT Cytotoxicity assay is used to test the ability of the compounds to ameliorate the mitochondrial toxicity and resulting loss of viability associated with the accumulation of α-synuclein aggregates. Phrased another way, the XTT Cytotoxicity assay is used to gauge the compounds neuroprotective efficacy. These studies are presented in the following examples.

To carry out these studies, a cell culture model was used in which human α-synuclein aggregation is experimentally induced. BE-M17 human neuroblastoma cells stably transfected with A53T-mutant human α-synuclein were obtained. Cell culture reagents were obtained from Gibco/Invitrogen, and cells were grown in OPTIMEM supplemented with 10% FBS, Penicillin (100 units/ml), Streptomycin (100 μg/ml) and 500 μg/ml G418 as previously described (Ostrerova-Golts et al., *J. Neurosci.,* 20:6048-6054, 2000).

Thioflavin S is commonly used to detect amyloid-containing structures in situ, including in brain tissue (Vallet et al., *Acta Neuropathol.,* 83:170-178, 1992), and cultured cells (Ostrerova-Golts et al., *J. Neurosci.,* 20:6048-6054, 2000), whereas thioflavin T is often used as an in vitro reagent to analyze the aggregation of soluble amyloid proteins into fibrils enriched in β-pleated sheet structures (LeVine III, *Prot. Sci.,* 2:404-410, 1993). Therefore, Thioflavin S histochemistry was used on cultured cells to detect aggregates containing a high degree of β-pleated structures that formed in response to oxidative stress-inducing agents (in this case rotenone) as previously described, with minor modifications (Ostrerova-Golts et al., *J. Neurosci.,* 20:6048-6054, 2000). Briefly, for these studies, cells were grown on Poly-D-Lysine coated glass slide chambers at approximately $3 \times 10^4$ cells/cm². After 24 hours, cells were treated with 500 nM, 1 μM or 5 μM rotenone (Sigma) or vehicle (0.05% DMSO) as indicated. Immediately after rotenone (or vehicle) addition, compounds were added at the indicated concentration, or cell culture media only (no compound) in the presence of rotenone was added. Identical treatments were repeated after 48 hours. After an additional 48 hours, cells were fixed for 25 minutes in 3% paraformaldehyde. After a PBS wash, the cells were incubated with 0.015% thioflavin S in 50% ethanol for 25 minutes, washed twice for four minutes in 50% ethanol and twice for five minutes in deionized water and then mounted using an aqueous-based mountant designed to protect against photobleaching. Aggregates that bind to thioflavin S were detected with a fluorescent microscope using a High Q FITC filter set (480 to 535 nm bandwidth) and a 20× objective lens unless otherwise indicated. Between 8 and 16 representative images per condition were selected, imaged and processed by an experimenter who was blinded to treatment conditions. To assess the amount of thioflavin S-positive aggregates, the total area per field covered by thioflavin S-positive inclusions was determined. For this purpose, background fluorescence that failed to exceed pre-set size or pixel intensity threshold parameters was eliminated using Q-capture software. Spurious, non-cell associated fluorescence was manually removed. Unless indicated otherwise, data represent group means±SEM. Statistical analyses were performed with GraphPad Prism (GraphPad Inc). Differences between means (two samples) were assessed by the Student's t test. Differences among multiple means were assessed by one-factor ANOVA followed by Tukey's multiple comparison test.

To validate the ability of the assay to quantitatively detect aggregates that bind thioflavin S, staining of BE-M17 cells overexpressing A53T α-synuclein was carried out and the results revealed a rotenone dose-dependent increase in thioflavin S-positive aggregates relative to vehicle-treated control cells (FIG. 9A-D). Higher magnification images obtained with a 40× objective indicated that the thioflavin S-positive aggregates were intracellular and cytoplasmic (FIG. 9D), analogous to the accumulation of intracytoplasmic Lewy bodies which are pathological hallmarks associated with Parkinson's disease. Quantitation of the area covered by thioflavin-S-positive aggregates established that 5 µM of rotenone was sufficient to induce robust aggregation (FIG. 9E) and thus is an effective dose to test the ability of compounds to attenuate the formation of these aggregates.

Using the protocol described above, several compounds were tested for their ability to reduce, prevent or eliminate thioflavin S-positive aggregates in rotenone-treated BE-M17 cells overexpressing A53T α-synuclein. Examples of results obtained from experiments using these compounds are described below.

Figure 10:
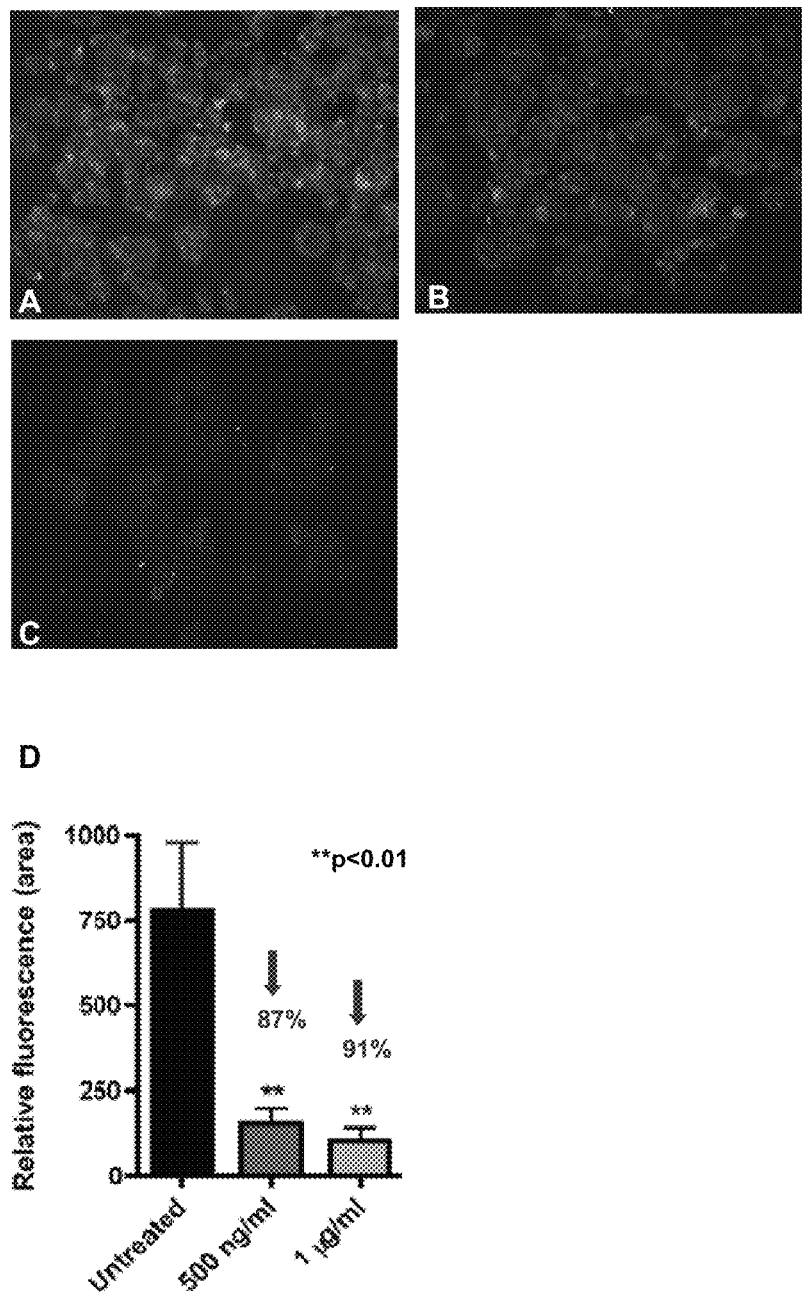
FIGS. 10 A-D are examples of fluorescent photomicrographs demonstrating a reduction in thioflavin S-positive aggregates (green fluorescence) upon application of a positive control compound.

In cells treated with 1 µM rotenone only, there was a robust presence of thioflavin S-positive aggregates (FIG. 10A). Addition of 500 ng/ml (FIG. 10B) or 1 µg/ml (FIG. 10C) of positive control compound markedly reduced the abundance of these rotenone-induced aggregates by 87% and 91% respectively (as shown in FIG. 10D) relative to rotenone only-treated cells. Therefore, the positive control compound is highly effective at the reduction, prevention and/or elimination of thioflavin S-positive aggregates in cells that express human A53T α-synuclein.

Figure 11:
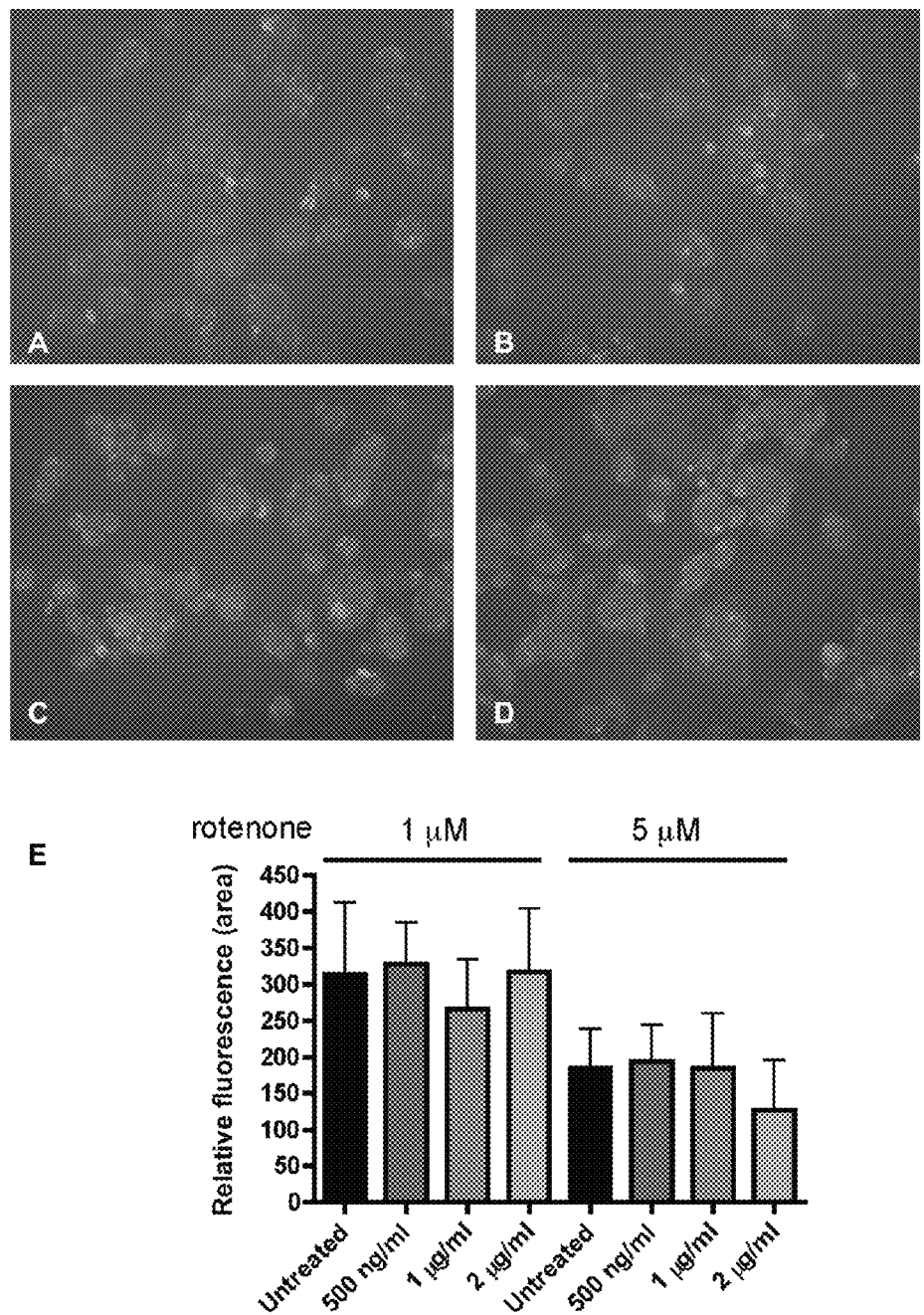
FIGS. 11 A-E are examples of fluorescent photomicrographs demonstrating the effects of compound 1 on the presence of rotenone-induced thioflavin S-positive aggregates (green) in cells in a dose dependent manner.

Addition of from 500 ng/ml up to 2 µg/ml (FIGS. 11B-D) of compound 1 did not reduce the abundance of rotenone-induced aggregates relative to rotenone only-treated cells (FIGS. 11D and E).

Figure 12:
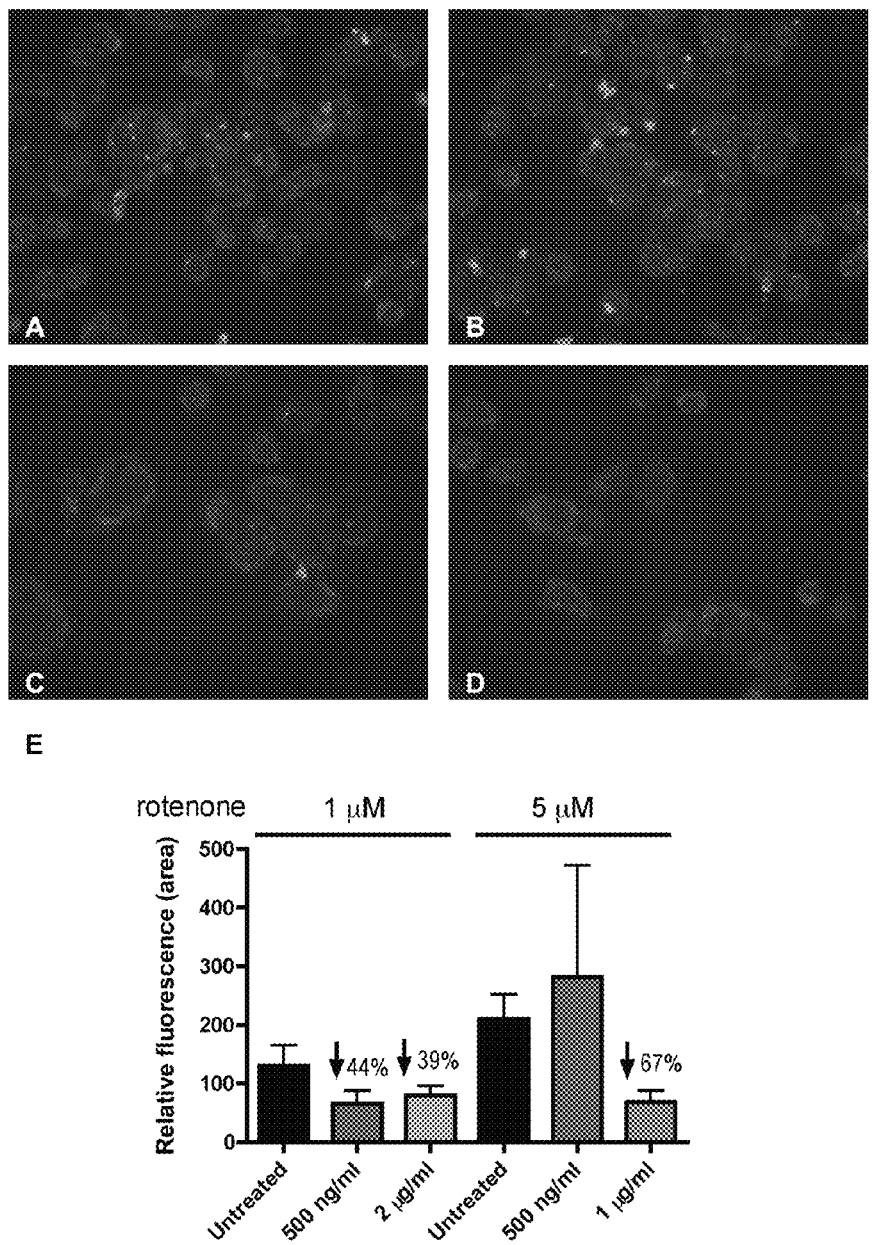
FIGS. 12 A-E are examples of fluorescent photomicrographs demonstrating that compound 2 strongly reduces the presence of rotenone-induced thioflavin S-positive aggregates (green) in cells.

As shown in FIG. 12, in cells treated with 1 µM rotenone the addition of 500 ng/ml and 2 µg/ml of compound 2 reduced the abundance of rotenone-induced aggregates by 39-44%, and in cells treated with 5 µM rotenone the addition of 1 µg/ml of compound 2 markedly reduced the abundance of rotenone-induced aggregates by 67% (FIG. 12E).

Figure 13:
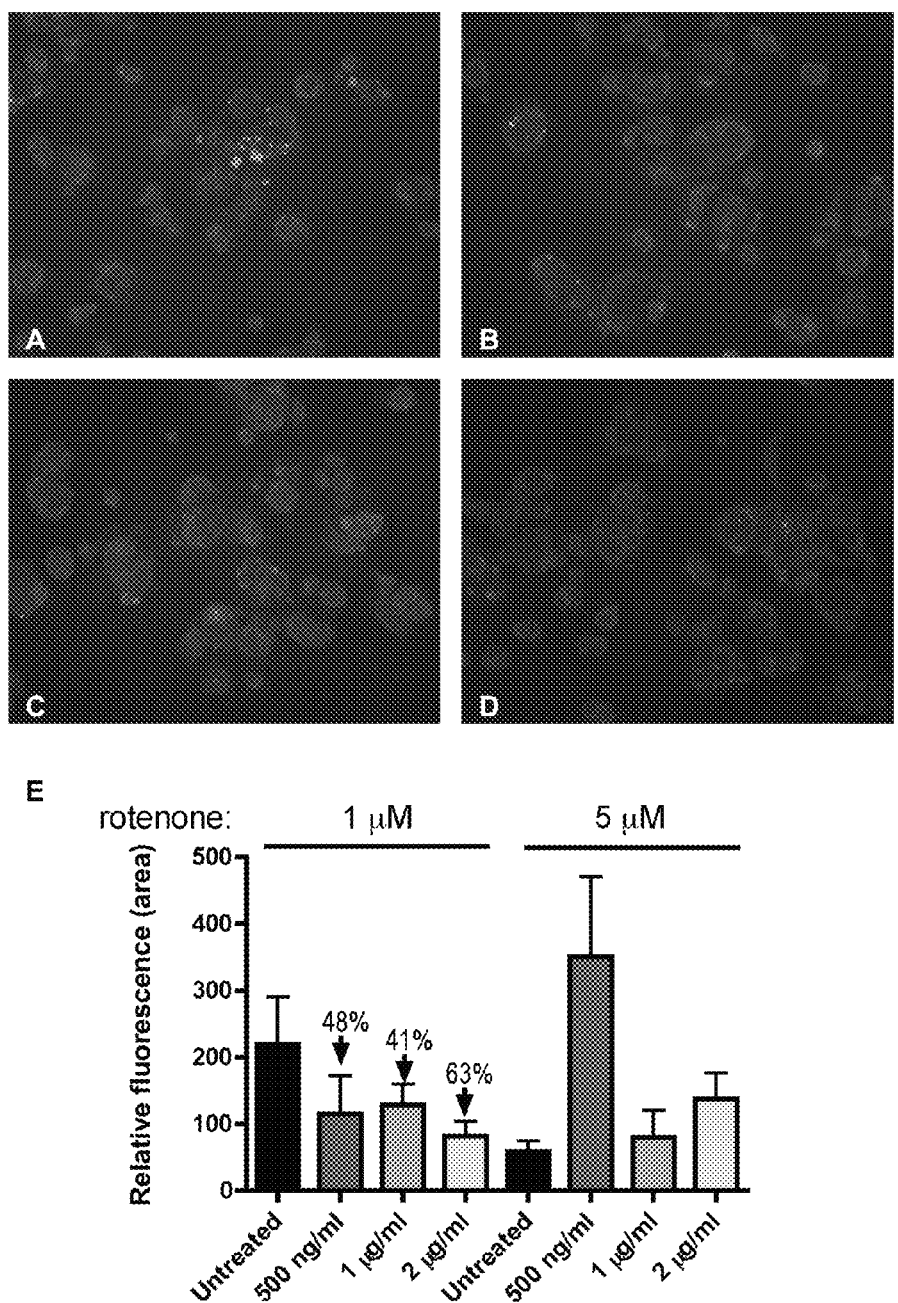
FIGS. 13 A-E are examples of fluorescent photomicrographs demonstrating that compound 3 reduces the presence of rotenone-induced thioflavin S-positive aggregates (green) in cells in a dose dependent manner.
Figure 14:
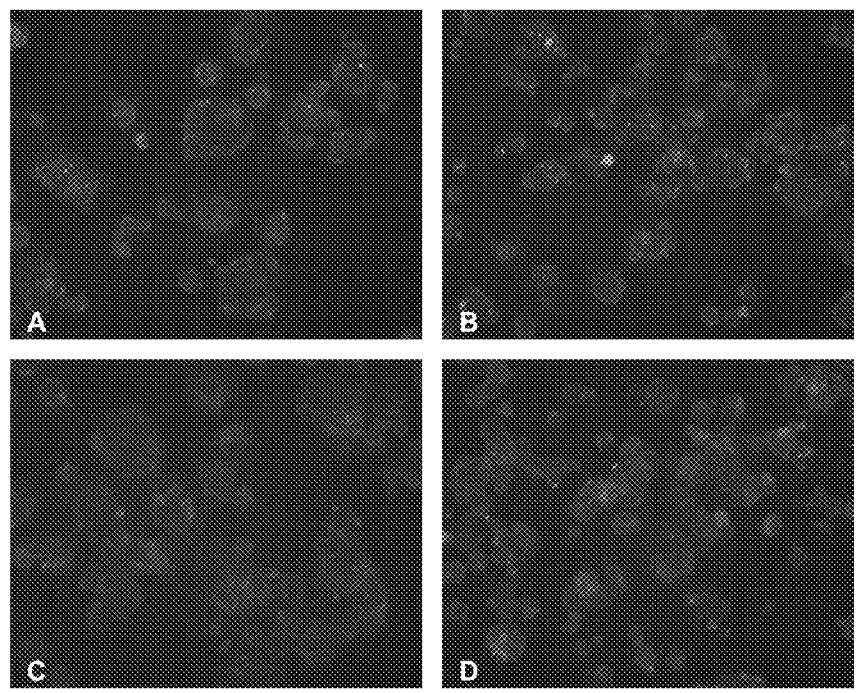
FIGS. 14 A-E are examples of fluorescent photomicrographs demonstrating that compound 4 minimally reduces the presence of rotenone-induced thioflavin S-positive aggregates (green) in cells in a dose dependent manner.
Figure 14:
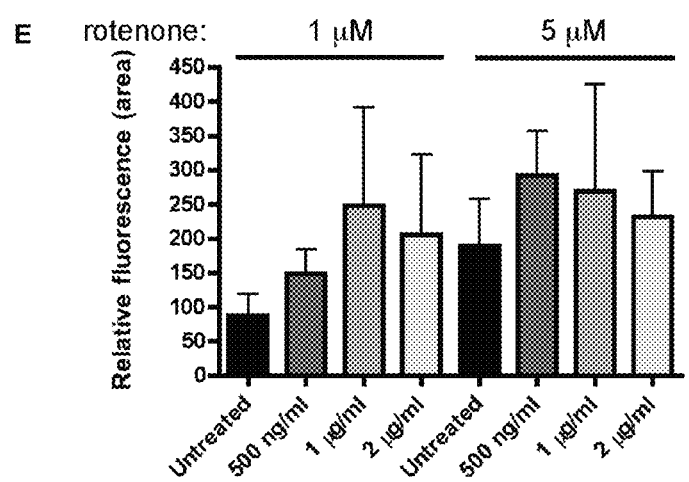

FIGS. 13 A-E show the effects of compound 3. In cells treated with 1 µM rotenone the addition of 500 ng/ml up to 2 µg/ml of compound 3 reduced the abundance of rotenone-induced aggregates by 41 to 63% relative to rotenone only-treated cells.

Addition of 500 ng/ml up to 2 µg/ml of compound 4 did not reduce the abundance of rotenone-induced aggregates relative to rotenone only-treated cells (FIGS. 14A-E).

Figure 15:
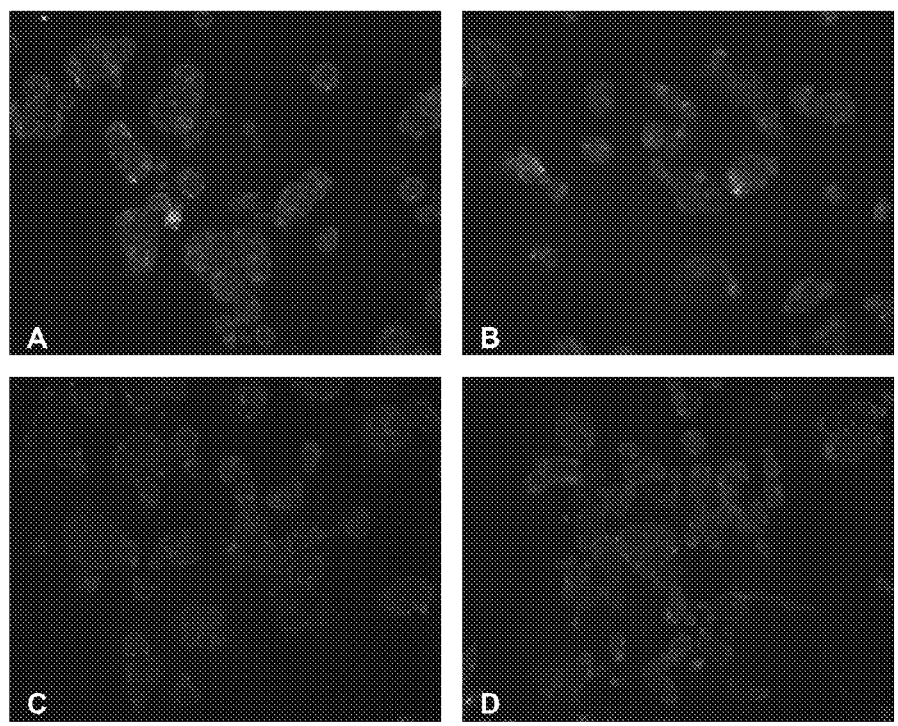
FIGS. 15 A-E are examples of fluorescent photomicrographs demonstrating that compound 5 mildly reduces the presence of rotenone-induced thioflavin S-positive aggregates (green) in cells in a dose dependent manner.
Figure 15:
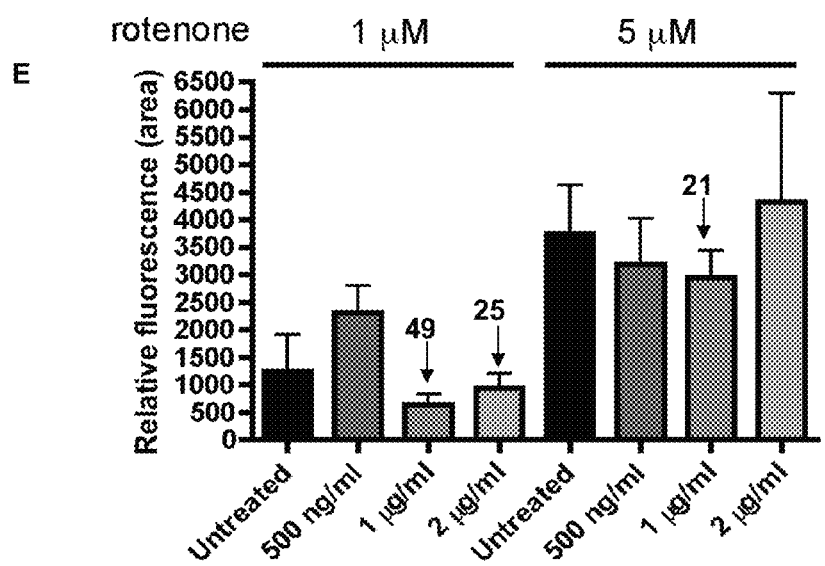
Figure 16:
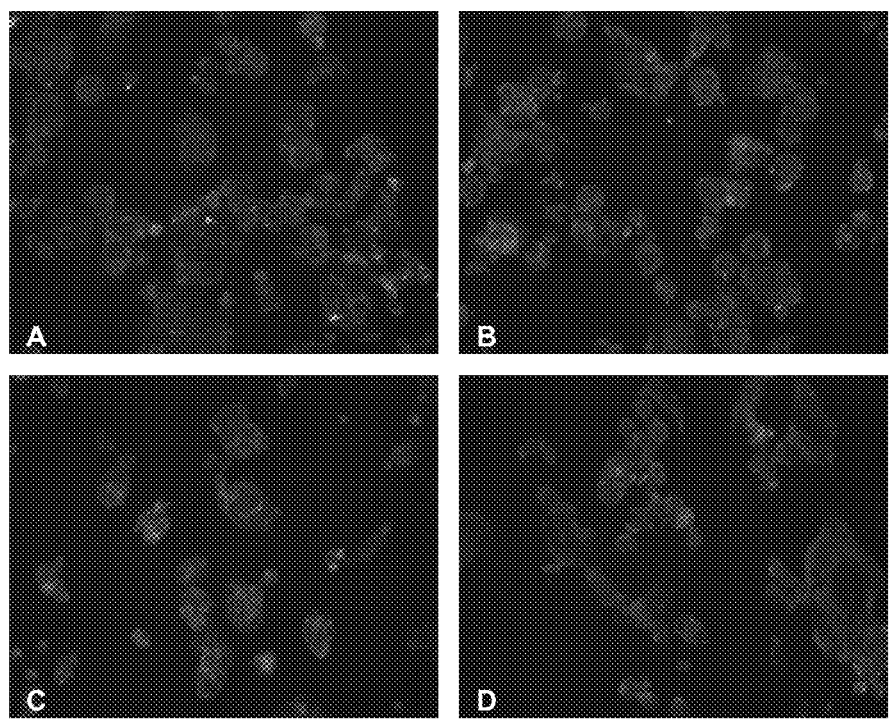
FIGS. 16 A-E are examples of fluorescent photomicrographs demonstrating that compound 6 minimally affects the presence of rotenone-induced thioflavin S-positive aggregates (green) in cells in a dose dependent manner.
Figure 16:
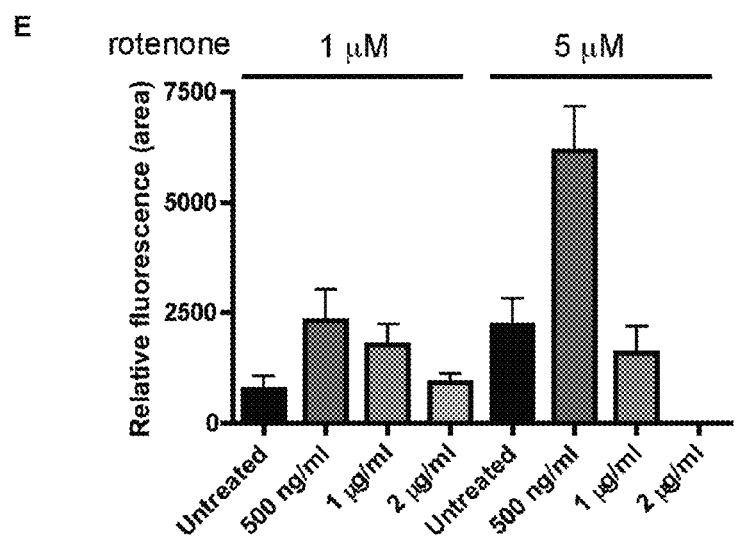
Figure 17:
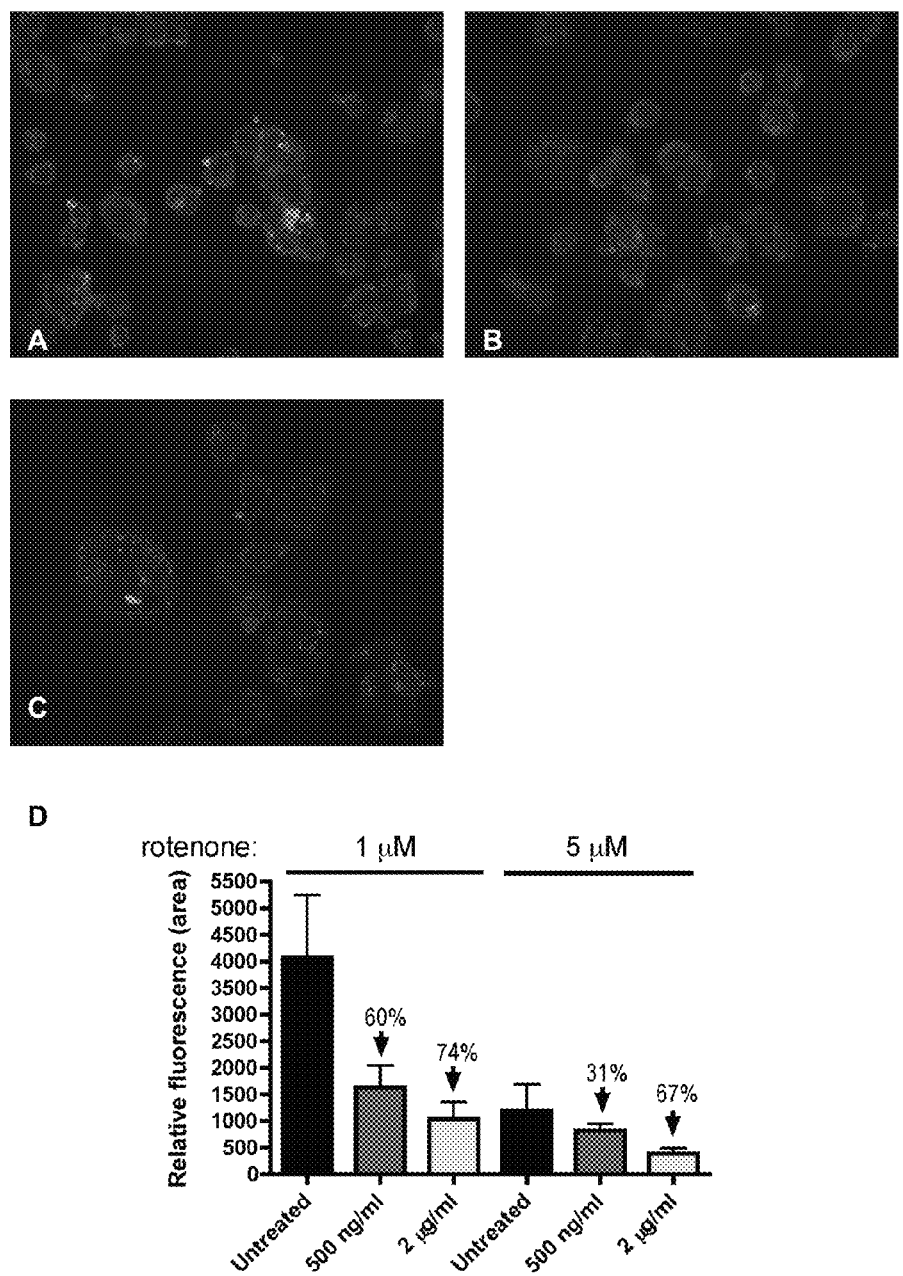
FIGS. 17 A-D are examples of fluorescent photomicrographs demonstrating that compound 7 moderately reduces the presence of rotenone-induced thioflavin S-positive aggregates (green) in cells in a dose dependent manner.

FIGS. 15 A-E show the effects of compound 5. In cells treated with 1 µM rotenone the addition of 1-2 µg/ml of compound 3 reduced the abundance of rotenone-induced aggregates by 25 to 49% relative to rotenone only-treated cells.

The addition of compound 6 did not have significant effects on the abundance of rotenone-induced aggregates relative to rotenone only-treated cells (FIGS. 16A-E).

The addition of 500 ng/ml and 2 µg/ml of compound 7 markedly reduced the abundance of rotenone-induced aggregates by 60 and 74% (respectively) relative to rotenone only-treated cells in cells treated with 1 µM rotenone only. In cells treated with 5 µM rotenone the addition of 500 ng/ml and 2 µg/ml of compound 7 reduced the abundance of rotenone-induced aggregates by 31 and 67% (respectively) (FIGS. 17A-E).

Figure 18:
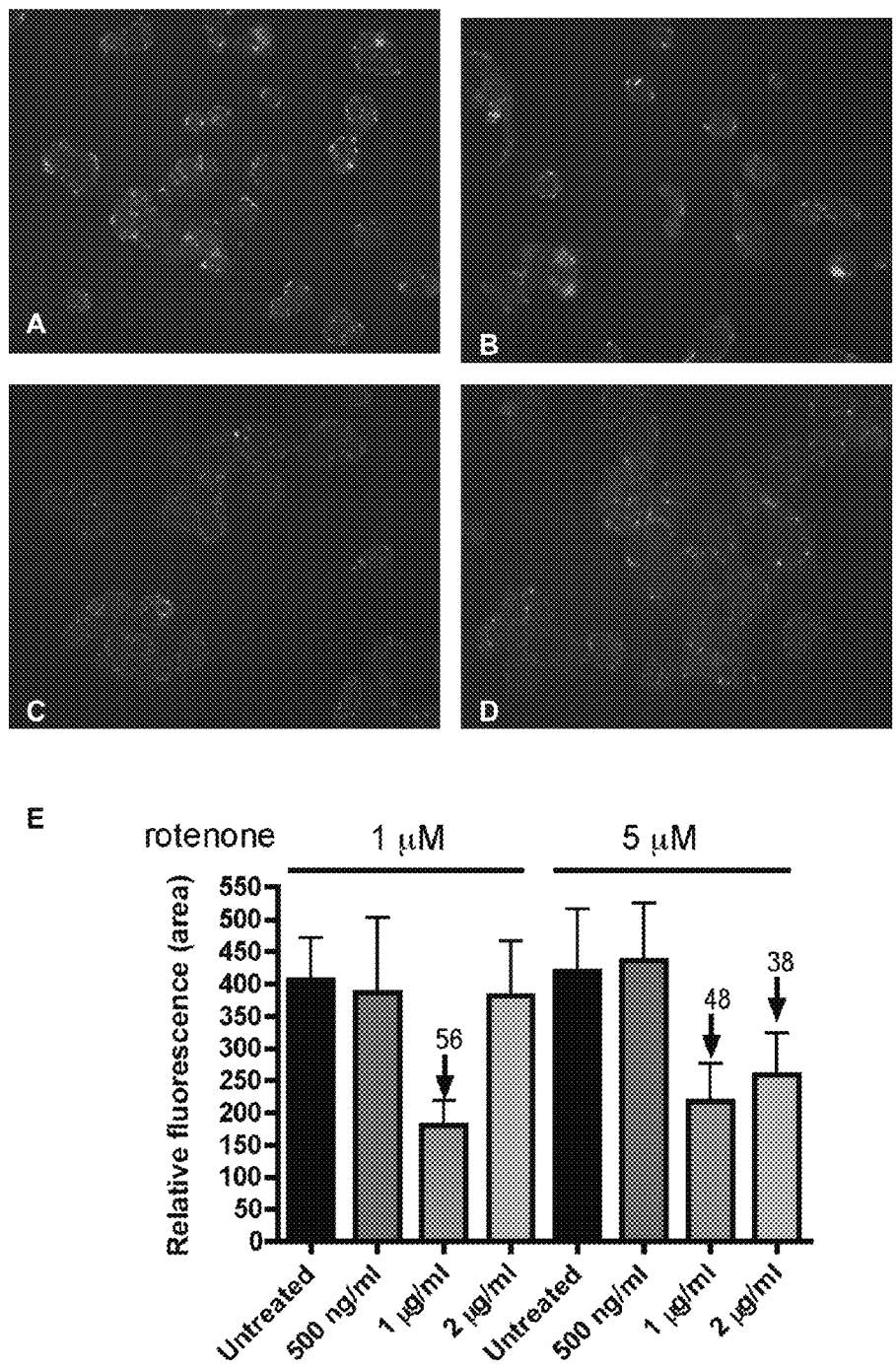
FIGS. 18 A-E are examples of fluorescent photomicrographs demonstrating that compound 8 moderately reduces the presence of rotenone-induced thioflavin S-positive aggregates (green) in cells in a dose dependent manner.
Figure 19:
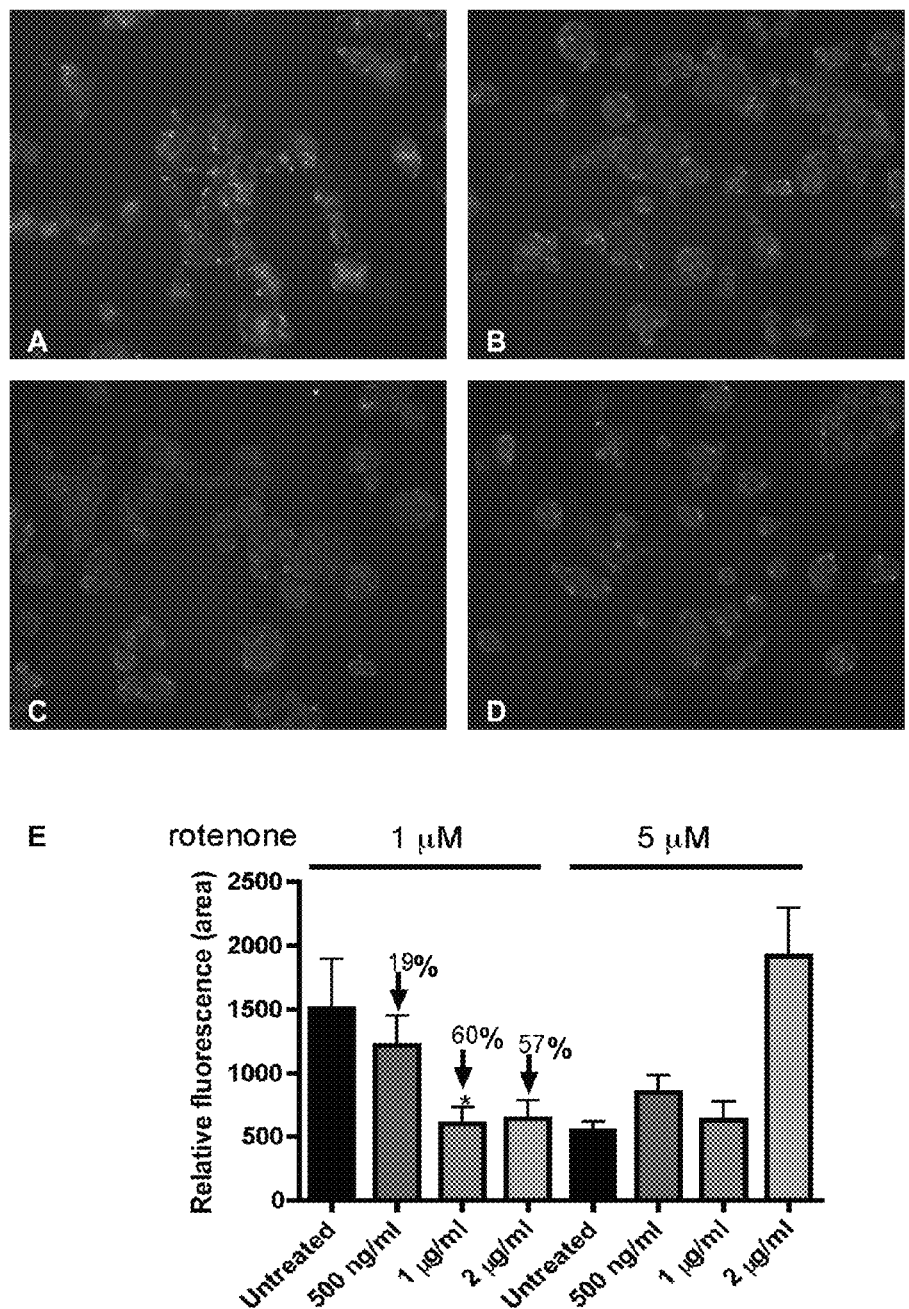
FIGS. 19 A-E are examples of fluorescent photomicrographs demonstrating that compound 9 reduces the presence of rotenone-induced thioflavin S-positive aggregates (green) in cells in a dose dependent manner.

FIGS. 18 A-E show the effects of compound 8. In cells treated with 1 µM rotenone the addition of 1 µg/ml of compound 8 reduced the abundance of rotenone-induced aggregates by 56% relative to rotenone only-treated cells. In cells treated with 5 µM rotenone the addition of 1 or 2 µg/ml of compound 8 reduced the abundance of rotenone-induced aggregates by 48 and 38% (respectively).

The addition of 500 ng/ml up to 2 µg/ml of compound 9 reduced the abundance of rotenone-induced aggregates from 19 to 60% relative to rotenone only-treated cells in cells treated with 1 µM rotenone (FIGS. 19A-E). The addition of compound 9 did not reduce the abundance of rotenone-induced aggregates in cells treated with 5 µM rotenone although baseline staining was lower than expected at this rotenone dose.

In conclusion, many of the compounds tested, especially compounds 2, 3, 5, 7, 8 and 9 effectively and potently reduced, prevented, inhibited and/or eliminated the formation, deposition and/or accumulation of α-synuclein aggregates in A53T α-synuclein-expressing BE-M17 cells.

Example 9

Compounds of this Invention Protect Against Rotenone-Induced Cytotoxicity

Figure 20:
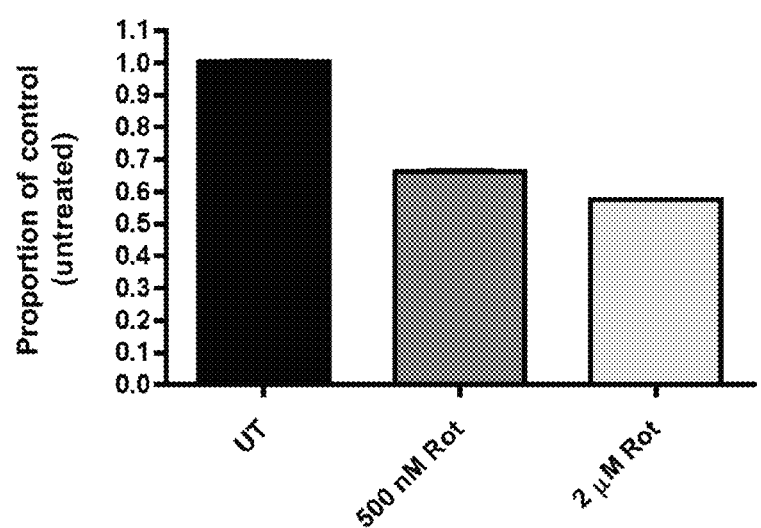
FIG. 20 is a graph showing 35-45% reduction in cell viability after 2 days of treatment with rotenone as measured by the XTT Cytotoxicity assay.

The XTT Cytotoxicity Assay (Roche Diagnostics, Mannheim, Germany) was previously used to demonstrate that A53T α-synuclein potentiates cell death in BE-M17 cells through an oxidative stress-dependent mechanism (Ostrerova-Golts et al., *J. Neurosci.*, 20:6048-6054, 2000). Research has shown that the accumulation of α-synuclein fibrils in Lewy bodies contributes mechanistically to the degradation of neurons in Parkinson's disease and related disorders (Polymeropoulos et al., *Science* 276:2045-2047, 1997; Kruger et al., *Nature Genet.* 18:106-108, 1998). Here, the XTT Cytotoxicity assay (hereafter referred to as the XTT assay) was used to measure the ability of test compounds to protect against rotenone-induced cytotoxicity (neuroprotective ability). The assay is based on the principle that conversion of the yellow tetrazolium salt XTT to form an orange formazan dye (that absorbs light around 490 nm) occurs only in metabolically active, viable cells. Therefore, light absorbance at 490 nm is proportional to cell viability. For this assay, cells were plated in 96 well tissue culture dishes at $10^4$ cells per well. After 24 hours, cells were treated with 500 nM or 2 µM rotenone, or vehicle (0.05% DMSO) as indicated. Immediately after rotenone addition, compounds were added at the indicated concentration. As a control, compounds were added without rotenone (vehicle only, 0.05% DMSO) and resulted in no toxicity at the doses tested. Untreated cells received cell culture media only (no compound, with or without rotenone). After 40-44 hours of treatment, conditioned media was removed and replaced with 100 µl fresh media and 50 µl XTT labeling reaction mixture according to the manufacturer's recommendations. Five to six hours later, the absorbance at 490 nm was measured and corrected for absorbance at the 700 nm reference wavelength. Treatment with 500 nM and 2 µM rotenone usually decreased viability by 35-45% relative to untreated cell without rotenone (FIG. 20). Percent inhibition of cell death was calculated as the proportion of the rotenone-induced absorbance (viability) decrease that was eliminated by test compound treatment.

Figure 21:
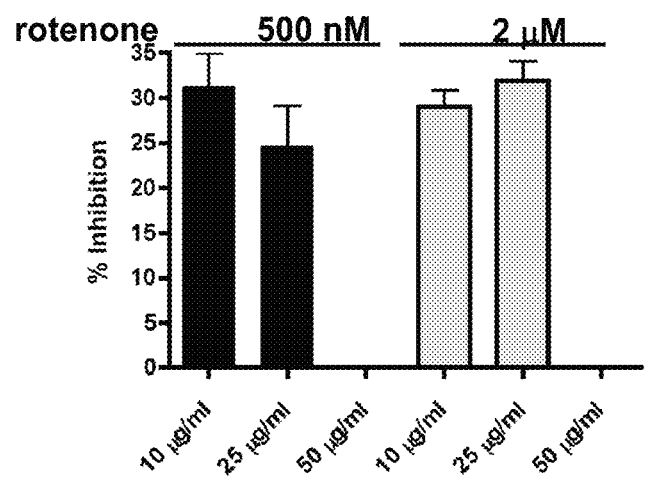
FIG. 21 is a graph showing the ability of the positive control compound to inhibit rotenone-induced toxicity as measured by the XTT Cytotoxicity assay.
Figure 22:
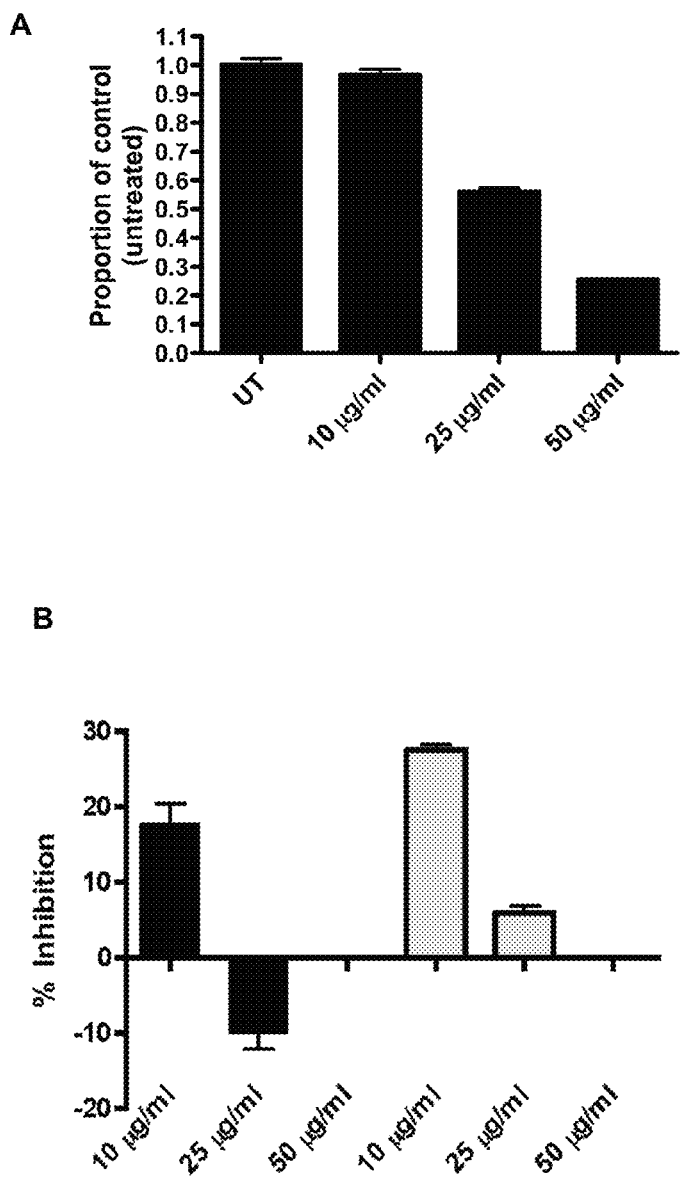
FIG. 22 A is a graph showing that compound 1 is non-toxic up to 10 μg/ml.
Figure 23:
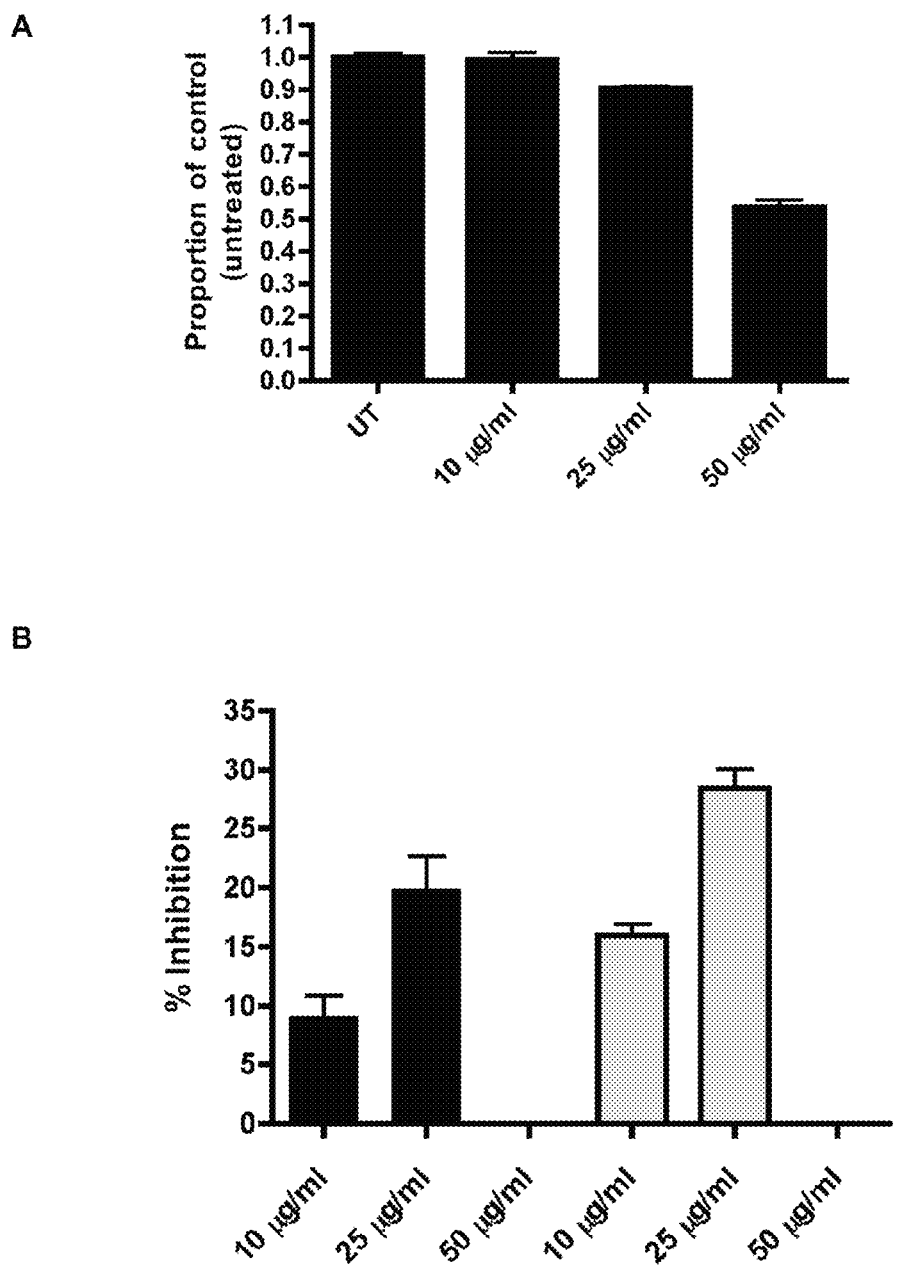
FIG. 23 A is a graph showing that compound 2 is non-toxic up to 25 μg/ml.
Figure 24:
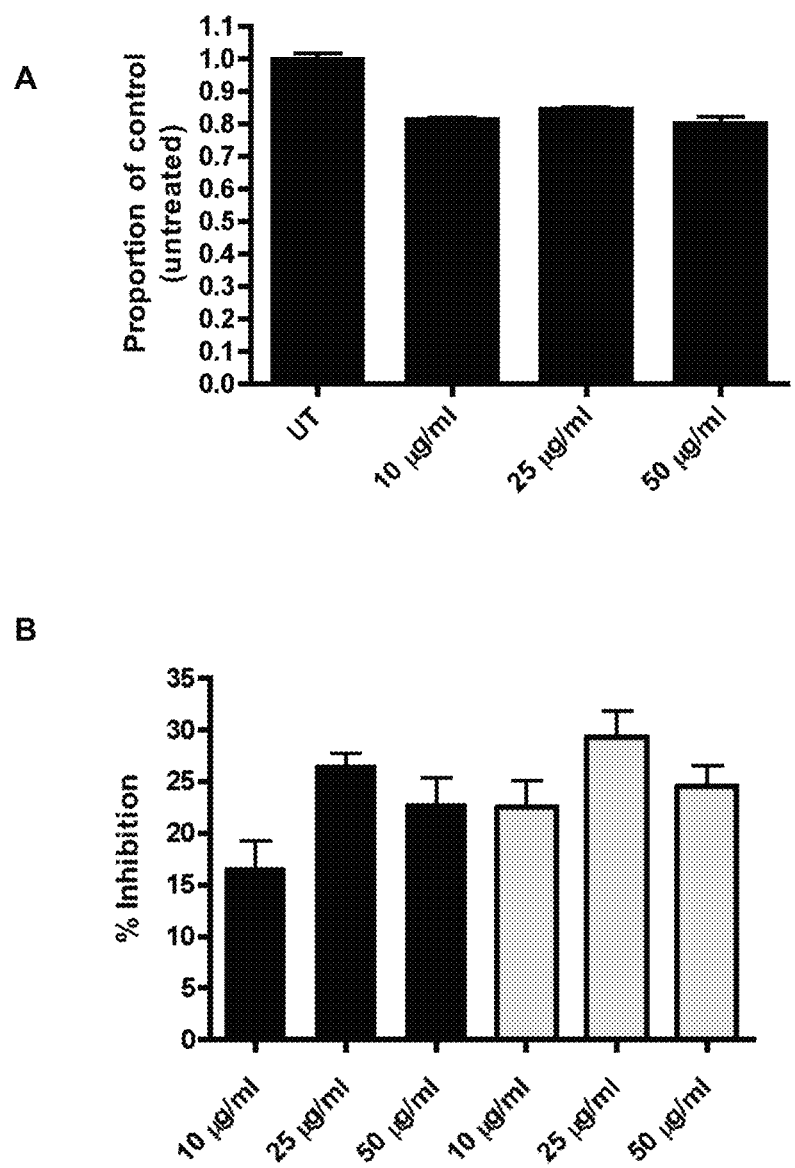
FIG. 24 A is a graph showing that compound 3 is non-toxic up to 50 μg/ml.
Figure 25:
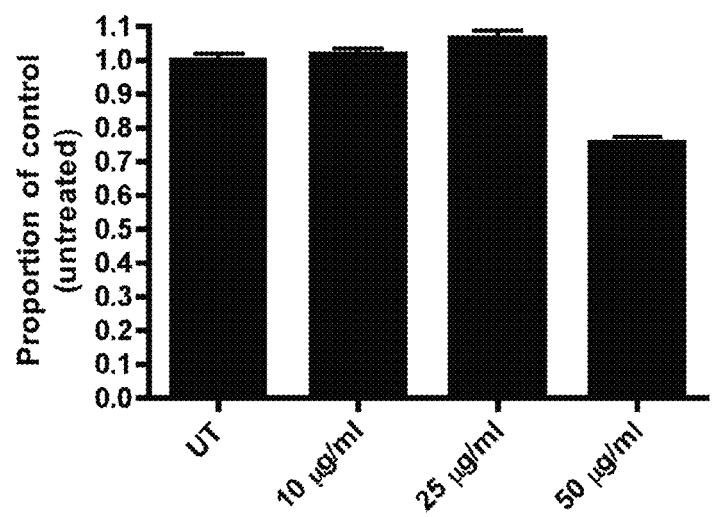
FIG. 25 A is a graph showing that compound 4 is non-toxic up to 25 μg/ml.
Figure 25:
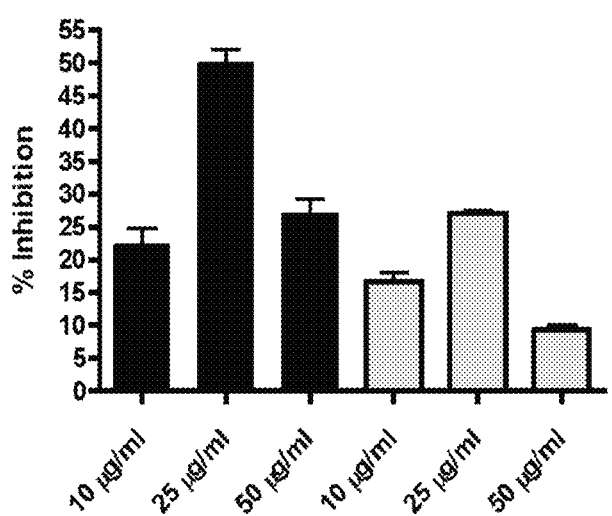
Figure 26:
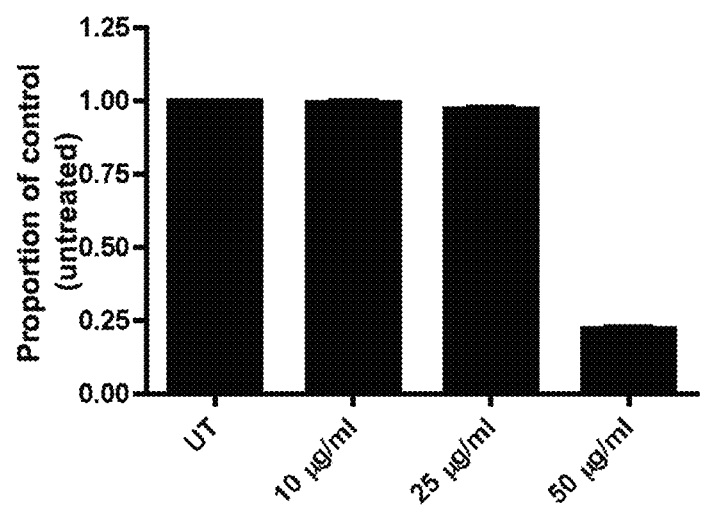
FIG. 26 A is a graph showing that compound 5 is non-toxic up to 25 μg/ml.
Figure 26:
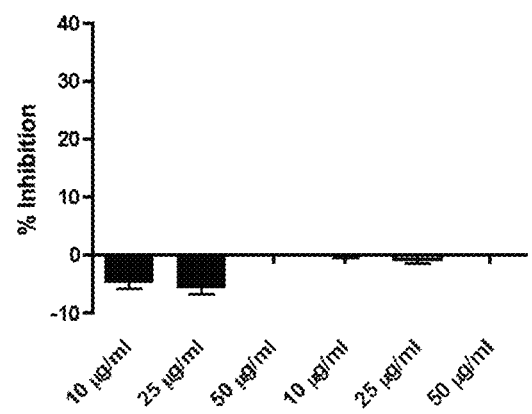
Figure 27:
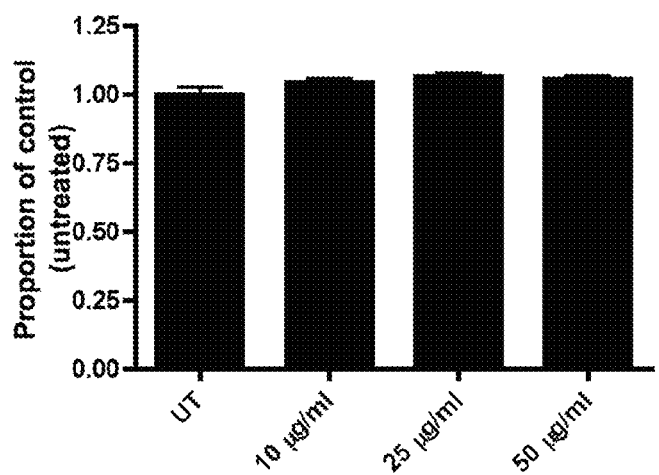
FIG. 27 A is a graph showing that compound 6 is non-toxic up to 50 μg/ml.
Figure 27:
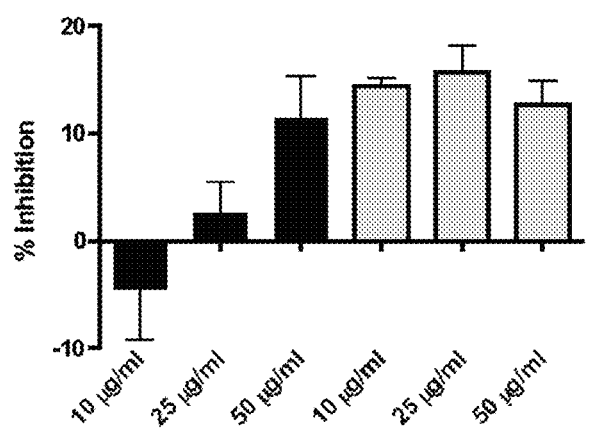
Figure 28:
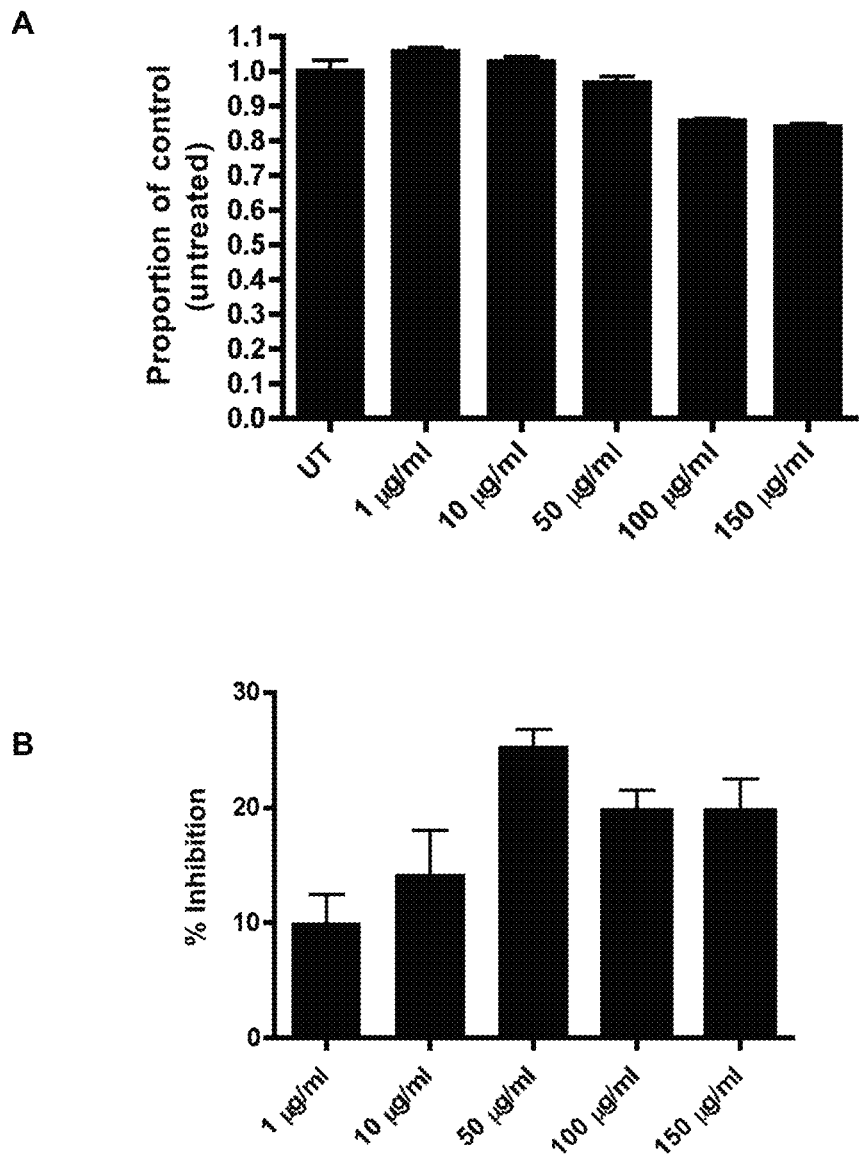
FIG. 28 A is a graph showing that compound 7 is non-toxic up to 50 μg/ml.
Figure 29:
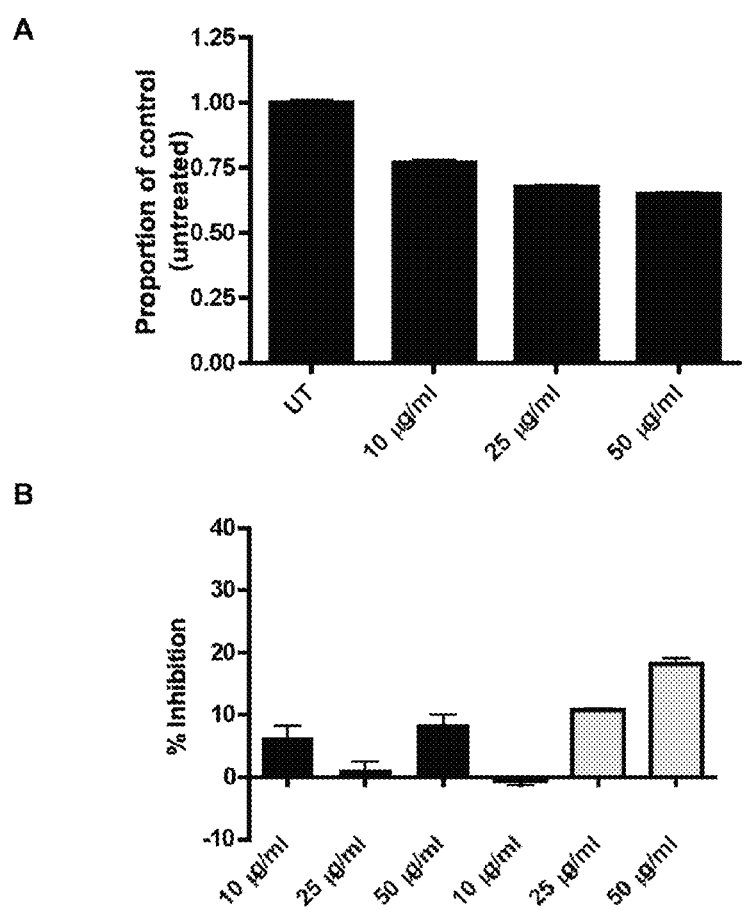
FIG. 29 A is a graph showing that compound 8 is non-toxic up to 25 μg/ml.
Figure 30:
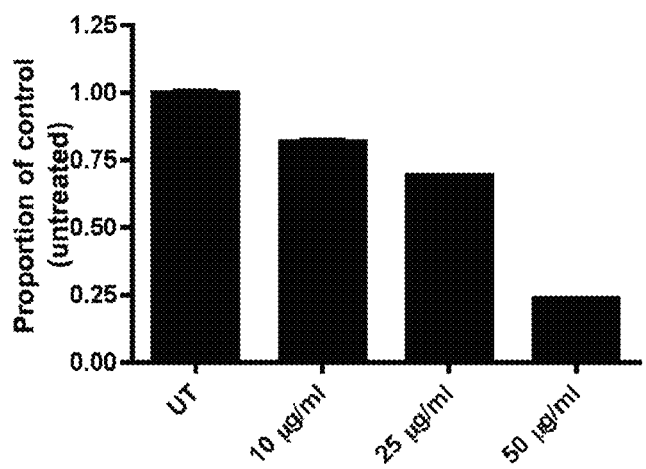
FIG. 30 A is a graph showing that compound 9 is non-toxic up to 25 μg/ml.
Figure 30:
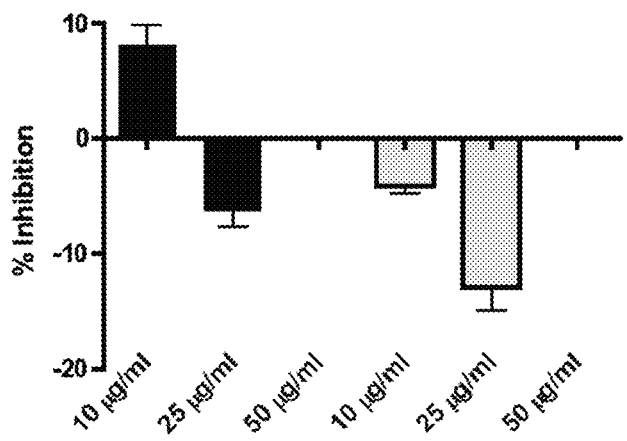

Treatment with positive control compound at 10-25 µg/ml inhibited the rotenone-induced loss of viability by 25-33% at both rotenone doses (FIG. 21).

The experiment was performed with each compound and the results are shown in FIGS. 22-30. FIGS. 22-30, panel A graphically illustrates the toxicity of the compound whereas FIGS. 22-30, panel B show inhibition by the compound of the rotenone-induced loss of viability measured at both rotenone doses.

Treatment with 10 µg/ml of compound 1 indicates that this compound is non-toxic, whereas higher doses displayed some toxicity (FIG. 22A). Treatment with 10 μg/ml of compound 1 inhibited the rotenone-induced loss of viability by approximately 18 to 27% at both rotenone doses (FIG. 22B).

Treatment with 10-25 μg/ml of compound 2 indicates that this compound is non-toxic, whereas a dose of 50 μg/ml displayed some toxicity (FIG. 23A). Treatment with 25 μg/ml of compound 2 inhibited the rotenone-induced loss of viability by approximately 20 to 28% at both rotenone doses (FIG. 23B).

Treatment with 10 to 50 μg/ml of compound 3 indicates that this compound is relatively non-toxic at all the doses tested (FIG. 24A). Treatment with 10 to 50 μg/ml of compound 3 inhibited the rotenone-induced loss of viability by approximately 17 to 28% at both rotenone doses (FIG. 24B).

Treatment with 10 and 25 μg/ml of compound 4 indicates that this compound is non-toxic, whereas a dose of 50 μg/ml displayed minimal toxicity (FIG. 25A). Treatment with 25 μg/ml of compound 4 was particularly effective and inhibited the rotenone-induced loss of viability by approximately 50% at the 500 nM dose of rotenone, whereas at 2 μM the inhibition observed was approximately 26% (FIG. 25B).

Treatment with 10 or 25 μg/ml of compound 5 indicates that this compound is non-toxic, whereas a dose of 50 μg/ml displayed minimal toxicity (FIG. 26A). Treatment with compound 5 did not cause any inhibition of the rotenone-induced loss of viability at either rotenone dose (FIG. 26B).

Treatment with 10 to 50 μg/ml of compound 6 indicates that this compound is non-toxic at all the doses tested (FIG. 27A). Treatment with 50 μg/ml of compound 6 at the 500 nM dose of rotenone inhibited the rotenone-induced loss of viability by approximately 10% whereas at 2 μM rotenone, the inhibition observed was approximately 12-16% for all doses of the compound tested (FIG. 27B).

Treatment with 1 to 50 μg/ml of compound 7 indicates that this compound is non-toxic, and even higher doses (100-150 μg/ml) displayed only very minimal toxicity (FIG. 28A). Treatment with 50 μg/ml of compound 7 showed the highest inhibition of the rotenone-induced loss of viability at approximately 25% at the 500 nM dose of rotenone (FIG. 28B).

Treatment with 10 to 25 μg/ml of compound 8 indicates that this compound is relatively non-toxic (FIG. 29A). Despite some minor toxicity at 50 μg/ml, the compound apparently affords some protection against the strong rotenone toxicity. This conclusion is supported by morphological analysis (not shown). Treatment with 50 μg/ml of compound 1 at 2 μM rotenone showed inhibition of the rotenone-induced loss of viability by approximately 18% (FIG. 29B).

Treatment with 10 to 25 μg/ml of compound 9 indicates that this compound is relatively non-toxic, whereas the higher dose displayed some toxicity (FIG. 30A). Treatment with compound 9 did not cause any appreciable inhibition of the rotenone-induced loss of viability at either rotenone dose (FIG. 30B).

In conclusion, many of the tested compounds were efficacious in inhibiting rotenone-induced cytotoxicity demonstrating neuroprotective activity against α-synuclein toxicity.

Example 10

Improved Motor Performance of α-Synuclein Transgenic Mice Treated with Compounds of this Invention To assess the potential efficacy of compounds in a Parkinson's disease-relevant mouse model, transgenic mice overexpressing wild-type human α-synuclein under the control of the mouse Thy-1 promoter (Rockenstein E, et al., 2002. J Neurosci Res 68:568-578) were used. Human α-synuclein transgenic mice have proven to be useful models for Parkinson's disease, and thus a suitable system for testing potential therapeutic agents, for a number of reasons including the following. (1) The presence of α-synuclein aggregates that are detectable by both immunohistochemical (staining) and biochemical (western blot) methods. These aggregates are similar to the Lewy bodies (intracellular inclusions comprised primarily of α-synuclein) that are the pathological hallmark of Parkinson's disease (Rockenstein E, et al., 2002. J. Neurosci. Res. 68:568-578 and Hashimoto M, et al., 2003 Ann N Y Acad Sci 991:171-188). (2) The mice experience a dopaminergic deficit in the nigrostriatal pathway, as indicated by loss of tyrosine hydroxylase-immunoreactive neuronal projections in the striatum (Hashimoto M, et al., 2003 Ann N Y Acad Sci 991:171-188). This deficit is also seen in human PD patients. (3) The mice show deficits, including slowness of movement, loss of balance and coordination and muscle weakness in a motor function-dependent behavioral test such as the beam traversal test (Fleming S M, et al., 2004 J Neurosci 24:9434-9440 and Fleming S M, et al., 2006 Neuroscience 142:1245-1253).

Similar motor dysfunction is seen in human PD patients. To assess the potential efficacy of compounds to improve motor performance or minimize deficites, the challenging beam traversal test was conducted on compound-treated and vehicle-treated mice assessed prior to treatment at 0 months and again at 3 and 6 months of treatment. If compounds were effective, one would expect that mice administered these compounds would perform better than vehicle-treated mice at the same age, and/or that test compound treatment might ameliorate age-dependent decline in performance within a given group. For example, if test compounds were effective, one might expect compound treated-mice to cross the beam more quickly, relative to vehicle-treated mice. Or one might expect age-dependent impairments within a group to be lessened (for example performance after compound treatment might be similar to performance prior to treatment, or even better, whereas vehicle-treated mice perform progressively worse over the same period of time).

Beam Traversal Test

In the beam traversal test, which is one measure of motor performance, mice are trained over two days, with five trials per day, to cross a narrowing beam (separated into four segments) with support ledges attached along each side, and leading to the animal's home cage. On the third day, the test is made more challenging by placing a mesh grid over the beam surface, leaving a small space of about 1 cm between the grid and the surface of the beam. Animals are then videotaped over a period of five trials, and the time to cross, number of steps taken and number of slips are recorded by an investigator blind to drug treatment (Fleming S M, et al., 2006. Neuroscience 142:1245-1253).

Figure 31:
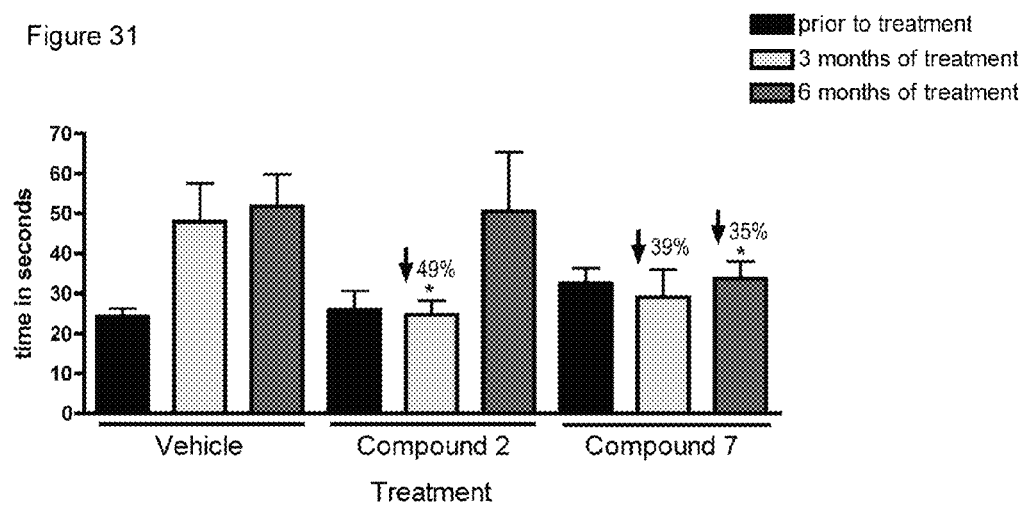
FIG. 31 is a graph showing beam traversal times and the effects of compound treatment. Treatment with compounds 2 and 7 improve the motor performance in the beam traversal test. At three months of treatment, compound 2 improves the motor performance (measured by a reduction in time to cross) in the beam traversal test significantly ($p<0.05$) by 49%, relative to vehicle-treated mice at the same age. At six months of treatment, compound 7 improves the motor performance in the beam traversal test significantly ($p<0.05$) by 35%, relative to vehicle-treated mice at the same age. In addition, compound 7 shows a general trend in improving motor performance by 39% at three months of treatment, relative to vehicle-treated mice at the same age.

Transgenic mice administered compound 2 for three months showed a marked, significant 49% improvement (time to cross the beam) relative to vehicle-treated, age-matched (15 months of age), control mice (FIG. 31). After six months of treatment, however, performance was similar to vehicle-treated mice at this age (FIG. 31). Taken together, these data show that compound 2 delays the onset of behavioral deficits in the beam traversal test.

Transgenic mice administered compound 7 for six months showed a marked, significant 35% improvement (time to cross the beam) relative to vehicle-treated, age-matched (15 months of age), control mice (FIG. 31). In addition, after only three months of compound 7 treatment, performance was 39% improved relative to vehicle-treated controls (FIG. 31).

Taken together, these data show that compound 7 treatment prevents the age-dependent progression of deficits in the beam traversal test.

Example 11

Compositions of Compounds of this Invention

The compounds of this invention, as mentioned previously, are desirably administered in the form of pharmaceutical compositions. Suitable pharmaceutical compositions, and the method of preparing them, are well-known to persons of ordinary skill in the art and are described in such treatises as *Remington: The Science and Practice of Pharmacy*, A. Gennaro, ed., 20th edition, Lippincott, Williams & Wilkins, Philadelphia, Pa.

Representative compositions are as follows:

Oral Tablet Formulation

An oral tablet formulation of a compound of this invention is prepared as follows:

|  | % w/w |
| --- | --- |
| Compound of this invention | 10.0 |
| Magnesium stearate | 0.5 |
| Starch | 2.0 |
| Hydroxypropylmethylcellulose | 1.0 |
| Microcrystalline cellulose | 86.5 |

The ingredients are mixed to homogeneity, then granulated with the aid of water, and the granulates are dried. The dried granulate is then compressed into tablets sized to give a suitable dose of the compound. The tablet is optionally coated by applying a suspension of a film forming agent (e.g. hydroxypropylmethylcellulose), pigment (e.g. titanium dioxide), and plasticizer (e.g. diethyl phthalate), and drying the film by evaporation of the solvent. The film coat may comprise, for example, 2-6% of the tablet weight.

Oral Capsule Formulation

The granulate from the previous section of this Example is filled into hard gelatin capsules of a size suitable to the intended dose. The capsule is banded for sealing, if desired.

Softgel Formulation

A softgel formulation is prepared as follows:

|  | % w/w |
| --- | --- |
| Compound of this invention | 20.0 |
| Polyethylene glycol 400 | 80.0 |

The compound is dissolved or dispersed in the polyethylene glycol, and a thickening agent added if required. A quantity of the formulation sufficient to provide the desired dose of the compound is then filled into softgels.

Parenteral Formulation

A parenteral formulation is prepared as follows:

|  | % w/w |
| --- | --- |
| Compound of this invention | 1.0 |
| Normal saline | 99.0 |

The compound is dissolved in the saline, and the resulting solution is sterilized and filled into vials, ampoules, and pre-filled syringes, as appropriate.

Controlled-Release Oral Formulation

A sustained release formulation may be prepared by the method of U.S. Pat. No. 4,710,384, as follows:

One Kg of a compound of this invention is coated in a modified Uni-Glatt powder coater with Dow Type 10 ethyl cellulose. The spraying solution is an 8% solution of the ethyl cellulose in 90% acetone to 10% ethanol. Castor oil is added as plasticizer in an amount equal to 20% of the ethyl cellulose present. The spraying conditions are as follows: 1) speed, 1 liter/hour; 2) flap, 10-15%; 3) inlet temperature, 50° C., 4) outlet temperature, 30° C., 5) percent of coating, 17%. The coated compound is sieved to particle sizes between 74 and 210 microns. Attention is paid to ensure a good mix of particles of different sizes within that range. Four hundred mg of the coated particles are mixed with 100 mg of starch and the mixture is compressed in a hand press to 1.5 tons to produce a 500 mg controlled release tablet.

The present invention is not limited in scope by the specific embodiments described herein. Indeed, various modifications of the invention in addition to those described will become apparent to those skilled in the art from the foregoing descriptions. Such modifications are intended to fall within the scope of the appended claims. Various publications are cited herein, the disclosures of which are incorporated by reference in their entireties.

We claim:

1. A compound selected from the group consisting of:

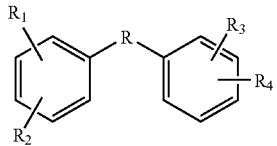

where $R_1$, $R_2$, $R_3$, and $R_4$ are independently positioned hydroxyl groups and R is selected from a sulfonamide, heteroaryl, tricycloalkyl or pharmaceutically acceptable esters or salts thereof and where the heteroaryl is selected from an imidazole or triazole.

2. The compound of claim 1 where R is sulfonamide.

3. The compound of claim 1 where the compound is 3,4-dihydroxybenzenesulfonic acid 3,4-dihydroxyphenylsulfonamide.

4. The compound of claim 1 where the compound is selected from the group consisting of:

2,4-bis(3,4-dihydroxyphenyl)imidazole; and 3,5-bis(3,4-dihydroxyphenyl) 1,2,4 triazole.

5. The compound of claim 1 where R is tricycloalkyl.

6. The compound of claim 1 where the compound is 1,3 bis-(3,4 dihydroxyphenyl) adamantane.

7. A pharmaceutical composition comprising the compound of claim 1 and a pharmaceutically acceptable excipient.

8. A method of treating the formation, deposition, accumulation, or persistence of Aβ amyloid or α-synuclein fibrils, comprising treating the fibrils with an effective amount of the compound of claim 1.

9. The method of claim 8 where the compound is selected from the group consisting of the compounds that are:

3,4-dihydroxybenzenesulfonic acid 3,4-dihydroxyphenyl-sulfonamide, 2,4-bis(3,4 dihydroxyphenyl) imidazole, 3,5-bis(3,4 dihydroxyphenyl) 1,2,4 triazole, and 1,3-bis(3,4 dihydroxyphenyl) adamantane;
and
the pharmaceutically acceptable salts of the compounds.

10. A method of treating a β-amyloid disease or a synucleinopathy in a mammal suffering therefrom, comprising administration of a therapeutically effective amount of the compound of claim 1.

11. The method of claim 10 where the β-amyloid disease is selected from the group of diseases consisting of Alzheimer's disease, Down's syndrome, hereditary cerebral hemorrhage with amyloidosis of the Dutch type, and cerebral β-amyloid angiopathy.

12. The method of claim 10 where the β-amyloid disease is Alzheimer's disease.

13. The method of claim 10 where the synucleinopathy is selected from the group consisting of Parkinson's disease, familial Parkinson's disease, Lewy body disease, the Lewy body variant of Alzheimer's disease, dementia with Lewy bodies, multiple system atrophy, and the Parkinsonism-dementia complex of Guam.

14. The method of claim 10 where the synucleinopathy is Parkinson's disease.

15. The method of claim 10 where the compound is selected from the group consisting of
the compounds that are:
3,4-dihydroxybenzenesulfonic acid 3,4-dihydroxyphenyl-sulfonamide,
2,4-bis(3,4 dihydroxyphenyl)imidazole,
3,5-bis(3,4 dihydroxyphenyl)1,2,4 triazole, and
1,3-bis(3,4 dihydroxyphenyl)adamantane;
and
the pharmaceutically acceptable salts of the compounds of (1) and (2).

* * * * *